(12) United States Patent
Robl et al.

(10) Patent No.: US 6,395,767 B2
(45) Date of Patent: May 28, 2002

(54) CYCLOPROPYL-FUSED PYRROLIDINE-BASED INHIBITORS OF DIPEPTIDYL PEPTIDASE IV AND METHOD

(75) Inventors: Jeffrey A. Robl, Newtown, PA (US); Richard B. Sulsky, West Trenton, NJ (US); David J. Augeri, Princeton, NJ (US); David R. Magnin, Hamilton, NJ (US); Lawrence G. Hamann, Cherry Hill, NJ (US); David A. Betebenner, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/788,173

(22) Filed: Feb. 16, 2001

Related U.S. Application Data
(60) Provisional application No. 60/188,555, filed on Mar. 10, 2000.

(51) Int. Cl.$^7$ .................. C07D 209/07; A61K 31/403
(52) U.S. Cl. .................................. 514/412; 548/452
(58) Field of Search ..................... 548/452; 514/412

(56) References Cited

U.S. PATENT DOCUMENTS

| | | |
|---|---|---|
| 4,254,057 A | 3/1981 | Day et al. |
| 4,379,785 A | 4/1983 | Weyer et al. |
| 5,462,928 A | 10/1995 | Bachovchin et al. |
| 5,939,560 A | 8/1999 | Jenkins et al. |
| 5,998,463 A | 12/1999 | Hulin et al. |
| 6,011,155 A | 1/2000 | Villhauer |
| 6,110,949 A | 8/2000 | Villhauer |

FOREIGN PATENT DOCUMENTS

| | | |
|---|---|---|
| DE | 33 24 263 A1 | 1/1985 |
| DE | 39 26 606 A1 | 2/1991 |
| EP | 0 007 652 A1 | 2/1980 |
| EP | 0 219 782 A2 | 4/1987 |
| EP | 1050540 A2 | 11/2000 |
| WO | WO 99/26659 | 6/1999 |
| WO | WO 99/38501 | 8/1999 |
| WO | WO 99/47545 | 9/1999 |
| WO | WO 99/67279 | 12/1999 |
| WO | WO 00/10549 | 3/2000 |
| WO | WO 034241 A1 | 6/2000 |
| WO | WO 00/53171 | 9/2000 |
| WO | WO 00/56296 | 9/2000 |
| WO | WO 00/56297 | 9/2000 |
| WO | WO 00/69868 | 11/2000 |
| WO | WO 97/40832 | 11/2001 |

OTHER PUBLICATIONS

Lin, J. et al, Proc. Natl. Acad. Sci, USA, vol. 95, pp. 14020–14024, Nov. 1998.
Augustyns, KJL et al, Eur. J. Med. Chem. 32, 301–309, (1997).
Hughes, T.E. et al, Biochemistry, 28, 11597–11603, 19993
Yamada, M. et al, Bioorganic & Medicinal Chemistry Letters 8, 1537–1540 (1998).
Tanaka, S. et al, Immunopharmacology 40, 21–26 (1998).
Li, J. et al, Archives of Biochemistry and Biophysics, vol. 323, No. 1, pp. 148–154, Oct. 20, 1995.
Ashworth, D.M. et al, Bioorganic & Medicinal Chemistry Letter, vol. 6, No. 22, pp. 2745–2748, 1996.
Yamada, M. et al, Bioorganic & Medicinal Chemistry Letter 8, 1537–1540 (1998).
Ashworth, D.M. et al, Bioorganic & Medicinal Chemistry Letter, vol. 6, No. 10, pp. 1163–1166, 1996.
Lambeir, A.–M., et al, Biochimica et Biophysica Acts, 1290, pp. 76–82 (1996).
Yoshimoto, T. et al, Agric. Biol. Chem., 55(4), pp. 1135–1136, 1991.
Belyaev, A. et al, J. Med. Chem., 42, 1041–1052, 1999.
Stockel, A. et al, Peptides: Chemistry, Structure and Biology, pp. 709–710, 1996.
Asai, Y. et al, The Journal of Antibiotics, vol. 50, No. 8, pp. 653–657, Aug. 1997.
Demuth, H.–U. et al, FEBS Letters, vol. 320, No. 1, pp. 23–27, Mar. 1993.
Ohnuki, T. et al, Drugs of the Future, 24(6):665–670, 1999.
Demuth, H.–U. et al, Diabetes, 2000, vol. 49, suppl. 1, A102.
Rotherberg, P. et al, Diabetes, 2000, vol. 49, Suppl. 1, A39.
Hiltmann, Arzneim. –Forsch. 24 (4) 548–600 1974 Abstract only.*
Sagnard, I. et al, Tetrahedron Letters, vol. 36, No. 18, pp. 3149–3152, 1995.
Tverezovsky, V. V. et al., Tetrahedron, vol. 53, No. 43, pp. 14773–14792, 1997.
Hanessian, S. et al, Bioorganic & Medicinal Chem. Letters, vol. 8, No. 16, pp. 2123–2128, Aug. 18, 1998.

* cited by examiner

*Primary Examiner*—Robert Gerstl
(74) *Attorney, Agent, or Firm*—Burton Rodney

(57) ABSTRACT

Dipeptidyl peptidase IV (DP 4) inhibiting compounds are provided having the formula

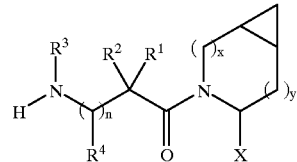

where
  x is 0 or 1 and y is 0 or 1 (provided that
  x=1 when y=0 and x=0 when y=1);
  n is 0 or 1; X is H or CN;
  and wherein $R^1$, $R^2$, $R^3$ and $R^4$ are as described herein.

A method is also provided for treating diabetes and related diseases, especially Type II diabetes, and other diseases as set out herein, employing such DP 4 inhibitor *or a combination of such DP 4 inhibitor and one or more of another antidiabetic agent such as metformin, glyburide, troglitazone, pioglitazone, rosiglitazone and/or insulin and/or one or more of a hypolipidemic agent and/or anti-obesity agent and/or other therapeutic agent.

24 Claims, No Drawings

CYCLOPROPYL-FUSED PYRROLIDINE-BASED INHIBITORS OF DIPEPTIDYL PEPTIDASE IV AND METHOD

This application takes priority from U.S. provisional application No. 60/188,555, filed Mar. 10, 2000.

FIELD OF THE INVENTION

The present invention relates to cyclopropyl-fused pyrrolidine-based inhibitors of dipeptidyl peptidase IV (DP-4), and to a method for treating diabetes, especially Type II diabetes, as well as hyperglycemia, Syndrome X, diabetic complications, hyperinsulinemia, obesity, atherosclerosis and related diseases, as well as various immunomodulatory diseases and chronic inflammatory bowel disease, employing such cyclopropyl-fused pyrrolidines alone or in combination with another type antidiabetic agent and/or other type therapeutic agent.

BACKGROUND OF THE INVENTION

Depeptidyl peptidase IV (DP-4) is a membrane bound non-classical serine aminodipeptidase which is located in a variety of tissues (intestine, liver, lung, kidney) as well as on circulating T-lymphocytes (where the enzyme is known as CD-26). It is responsible for the metabolic cleavage of certain endogenous peptides (GLP-1(7-36), glucagon) in vivo and has demonstrated proteolytic activity against a variety of other peptides (GHRH, NPY, GLP-2, VIP) in vitro.

GLP-1(7-36) is a 29 amino-acid peptide derived by post-translational processing of proglucagon in the small intestine. GLP-1(7-36) has multiple actions in vivo including the stimulation of insulin secretion, inhibition of glucagon secretion, the promotion of satiety, and the slowing of gastric emptying. Based on its physiological profile, the actions of GLP-1(7-36) are expected to be beneficial in the prevention and treatment of type II diabetes and potentially obesity. To support this claim, exogenous administration of GLP-1(7-36) (continuous infusion) in diabetic patients has demonstrated efficacy in this patient population. Unfortunately GLP-1(7-36) is degraded rapidly in vivo and has been shown to have a short half-life in vivo (t1/2≈1.5 min). Based on a study of genetically bred DP-4 KO mice and on in vivo/in vitro studies with selective DP-4 inhibitors, DP-4 has been shown to be the primary degrading enzyme of GLP-1(7-36) in vivo. GLP-1(7-36) is degraded by DP-4 efficiently to GLP-1(9-36), which has been speculated to act as a physiological antagonist to GLP-1(7-36). Thus, inhibition of DP-4 in vivo should potentiate endogenous levels of GLP-1(7-36) and attenuate formation of its antagonist GLP-1(9-36) and thus serve to ameliorate the diabetic condition.

DESCRIPTION OF THE INVENTION

In accordance with the present invention, cyclopropyl-fused pyrrolidine-based compounds are provided which inhibit DP-4 and have the structure

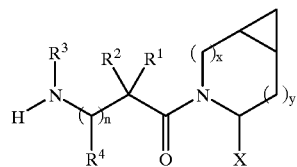

wherein x is 0 or 1 and y is 0 or 1 (provided that
x=1 when y=0 and
x=0 when y=1);

n is 0 or 1;

X is H or CN (that is cyano);

$R^1$, $R^2$, $R^3$ and $R^4$ are the same or different and are independently selected from H, alkyl, alkenyl, alkynyl, cycloalkyl, cycloalkylalkyl, bicycloalkyl, tricycloalkyl, alkylcycloalkyl, hydroxyalkyl, hydroxyalkylcycloalkyl, hydroxycycloalkyl, hydroxybicycloalkyl, hydroxytricycloalkyl, bicycloalkylalkyl, alkylthioalkyl, arylalkylthioalkyl, cycloalkenyl, aryl, aralkyl, heteroaryl, heteroarylalkyl, cycloheteroalkyl and cycloheteroalkylalkyl, all optionally substituted through available carbon atoms with 1, 2, 3, 4 or 5 groups selected from hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido or sulfonyl;

and $R^1$ and $R^3$ may optionally be taken together to form —$(CR^5R^6)_m$— where m is 2 to 6, and $R^5$ and $R^6$ are the same or different and are independently selected from hydroxy, alkoxy, cyano, H, alkyl, alkenyl, alkynyl, cycloalkyl, cycloalkylalkyl, cycloalkenyl, aryl, arylalkyl, heteroaryl, heteroarylalkyl, cycloheteroalkyl, halo, amino, substituted amino, cycloheteroalkylalkyl, alkylcarbonylamino, arylcarbonylamino, alkoxycarbonylamino, aryloxycarbonylamino, alkoxycarbonyl, aryloxycarbonyl, or alkylaminocarbonylamino, or $R^1$ and $R^4$ may optionally be taken together to form —$(CR^7R^8)_p$— where p is 2 to 6, and $R^7$ and $R^8$ are the same or different and are independently selected from hydroxy, alkoxy, cyano, H, alkyl, alkenyl, alkynyl, cycloalkyl, cycloalkylalkyl, cycloalkenyl, aryl, arylalkyl, heteroaryl, heteroarylalkyl, cycloheteroalkyl, halo, amino, substituted amino, cycloheteroalkylalkyl, alkylcarbonylamino, arylcarbonylamino, alkoxycarbonylamino, aryloxycarbonylamino, alkoxycarbonyl, aryloxycarbonyl, or alkylaminocarbonylamino, or optionally $R^1$ and $R^3$ together with

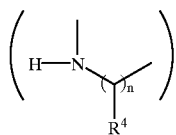

form a 5 to 7 membered ring containing a total of 2 to 4 heteroatoms selected from N, O, S, SO, or SO₂; or optionally R¹ and R³ together with

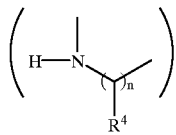

form a 4 to 8 membered cycloheteroalkyl ring wherein the cycloheteroalkyl ring has an optional aryl ring fused thereto or an optional 3 to 7 membered cycloalkyl ring fused thereto;

and including pharmaceutically acceptable salts thereof, and prodrug esters thereof, and all stereoisomers thereof.

Thus, the compounds of formula I of the invention include the following structures

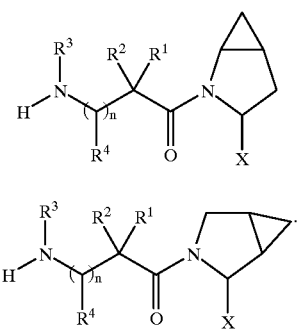

In addition, in accordance with the present invention, a method is provided for treating diabetes, especially Type II diabetes, as well as impaired glucose homeostasis, impaired glucose tolerance, infertility, polycystic ovary syndrome, growth disorders, frailty, arthritis, allograft rejection in transplantation, autoimmune diseases (such as scleroderma and multiple sclerosis), various immunomodulatory diseases (such as lupus erythematosis or psoriasis), AIDS, intestinal diseases (such as necrotizing enteritis, microvillus inclusion disease or celiac disease), inflammatory bowel syndrome, chemotherapy-induced intestinal mucosal atrophy or injury, anorexia nervosa, osteoporosis, Syndrome X, dysmetabolic syndrome, diabetic complications, hyperinsulinemia, obesity, atherosclerosis and related diseases, as well as inflammatory bowel disease (such as Crohn's disease and ulcerative colitis), wherein a therapeutically effective amount of a compound of structure I (which inhibits DP 4) is administered to a human patient in need of treatment.

The conditions, diseases, and maladies collectively referenced to as "Syndrome X" or Metabolic Syndrome are detailed in Johannsson *J. Clin. Endocrinol. Metab.*, 82, 727–734 (1997).

In addition, in accordance with the present invention, a method is provided for treating diabetes and related diseases as defined above and hereinafter as well as any of the other disease states mentioned above, wherein a therapeutically effective amount of a combination of a compound of structure I and one, two, three or more of other types of antidiabetic agent(s) (which may be employed to treat diabetes and related diseases) and/or one, two or three or more other types of therapeutic agent(s) is administered to a human patient in need of treatment.

The term "diabetes and related diseases" refers to Type II diabetes, Type I diabetes, impaired glucose tolerance, obesity, hyperglycemia, Syndrome X, dysmetabolic syndrome, diabetic complications, dysmetabolic syndrome, and hyperinsulinemia.

The conditions, diseases and maladies collectively referred to as "diabetic complications" include retinopathy, neuropathy and nephropathy, and other known complications of diabetes.

The term "other type(s) of therapeutic agents" as employed herein refers to one or more antidiabetic agents (other than DP4 inhibitors of formula I), one or more anti-obesity agents, and/or one or more lipid-modulating agents (including anti-atherosclerosis agents), and/or one or more infertility agents, one or more agents for treating polycystic ovary syndrome, one or more agents for treating growth disorders, one or more agents for treating frailty, one or more agents for treating arthritis, one or more agents for preventing allograft rejection in transplantation, one or more agents for treating autoimmune diseases, one or more anti-AIDS agents, one or more anti-osteoporosis agents, one or more agents for treating immunomodulatory diseases, one or more agents for treating chronic inflammatory bowel disease or syndrome and/or one or more agents for treating anorexia nervosa.

The term "lipid-modulating" agent as employed herein refers to agents which lower LDL and/or raise HDL and/or lower triglycerides and/or lower total cholesterol and/or other known mechanisms for therapeutically treating lipid disorders.

In the above methods of the invention, the compound of structure I will be employed in a weight ratio to the antidiabetic agent or other type therapeutic agent (depending upon its mode of operation) within the range from about 0.01:1 to about 500:1, preferably from about 0.1:1 to about 100:1, more preferably from about 0.2:1 to about 10:1.

Preferred are compounds of formula I wherein R³ is H or alkyl, R¹ is H, alkyl, cycloalkyl, bicycloalkyl, tricycloalkyl, alkylcycloalkyl, hydroxyalkyl, hydroxytricycloalkyl, hydroxycycloalkyl, hydroxybicycloalkyl, or hydroxyalkylcycloalkyl, R² is H or alkyl, n is 0, X is CN, x is 0 or 1 and y is 0 or 1.

Most preferred are preferred compounds of formula I as described above where X is

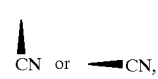

and/or wherein the fused cyclopropyl group is identified as

Thus, preferred compounds of formula I of the invention will include the moiety:

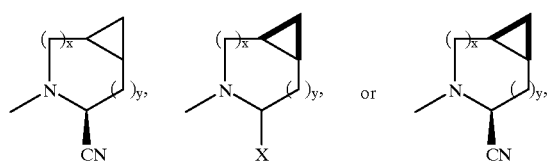

Particularly preferred are the following compounds:

A)

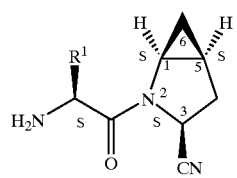

[1S, 2(2S), 3S, 5S]

wherein $R^1$ is alkyl, cycloalkyl, bicycloalkyl, tricycloalkyl, alkylcycloalkyl, hydroxyalkyl, hydroxycycloalkyl, hydroxyalkylcycloalkyl, hydroxybicycloalkyl or hydroxytricycloalkyl;

B)

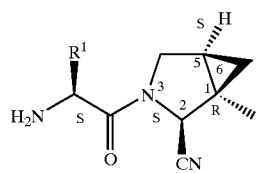

[1R, 2S, 3(2S), 5S]

wherein $R^1$ is alkyl, cycloalkyl, bicycloalkyl, tricycloalkyl, hydroxybicycloalkyl, hydroxytricycloalkyl, alkylcycloalkyl, hydroxyalkyl, hydroxycycloalkyl or hydroxyalkylcycloalkyl as well as the following:

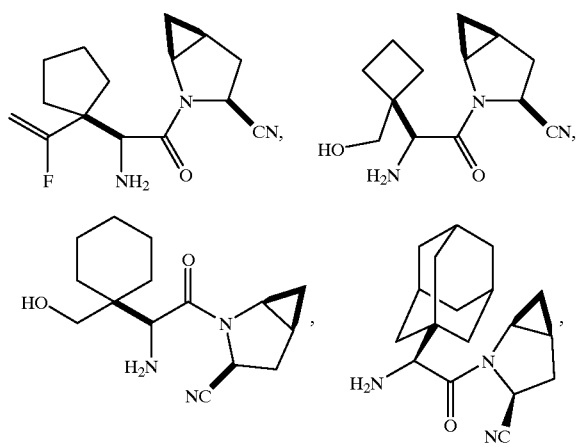

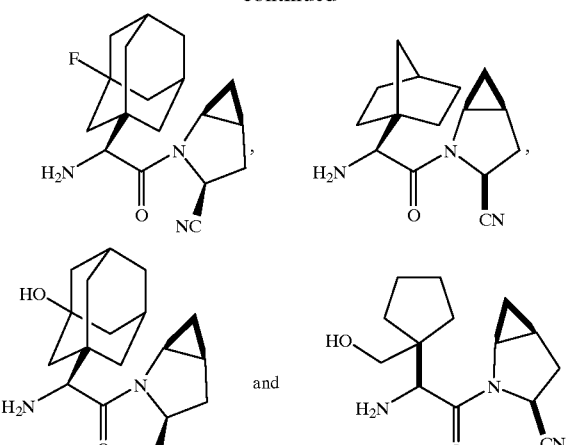

and

DETAILED DESCRIPTION OF THE INVENTION

Compounds of the structure I may be generated by the methods as shown in the following reaction schemes and the description thereof.

Referring to Reaction Scheme 1, compound 1, where $PG_1$ is a common amine protecting group such as Boc, Cbz, or FMOC and $X^1$ is H or $CO_2R^9$ as set out below, may be generated by methods as described herein or in the literature (for example see Sagnard et al, Tet-Lett., 1995, 36, pp. 3148–3152, Tverezovsky et al, Tetrahedron, 1997, 53, pp. 14773–14792, Hanessian et al, Bioorg. Med. Chem. Lett., 1998, 8, p. 2123–2128). Removal of the $PG_1$ group by conventional methods (e.g. (1) TFA or HCl when $PG_1$ is Boc, or (2) $H_2$/Pd/C, TMSI when $PG_1$ is Cbz, or (3) $Et_2NH$ when $PG_1$ is (FMOC) affords the free amine 2. Amine 2 may be coupled to various protected amino acids such as 3 (where $PG_2$ can be any of the $PG_1$ protecting groups) using standard peptide coupling conditions (e.g. EDAC/HOAT, i-BuCOCOCl/TEA, PyBop/NMM) to afford the corresponding dipeptide 4. Removal of the amine protecting group $PG_2$ provides compound Ia of the invention where X=H.

In the case where $X^1=CO_2R^9$ (where $R^9$ is alkyl or aralkyl groups such as methyl, ethyl, t-butyl, or benzyl), the ester may be hydrolyzed under a variety of conditions, for example with aqueous NaOH in a suitable solvent such as methanol, THF, or dioxane, to provide the acid 5. Conversion of the acid group to the primary carboxamide, affording 6, may be effected by activation of the acid group (e.g. employing i-BuOCOCl/TEA or EDAC) followed by treatment with $NH_3$ or an ammonia equivalent in a solvent such as dioxane, ether, or methanol. The amide functionality may be converted to the nitrile group by a variety of standard conditions (e.g. $POCl_3$/pyridine/imidazole or cyanuric chloride/DMF or trifluoroacetic anhydride, THF, pyridine) to give 7. Finally, removal of the $PG_2$ protecting group similar to above provides compound of the invention Ib.

In a different sequence (Scheme 2), compound 1 where $X^1$ is $CO_2R^9$ may be saponified to the acid and subsequently amidated as described above to give amide 8. Removal of the PG$_1$ group followed by peptide coupling to 3 affords compound 6, an intermediate in the synthesis of Ib.

Alternately, the carboxamide group in 8 may be converted to the nitrile as described above to give compound 9. Deprotection of PGI affords 10 which may be subject to standard peptide coupling conditions to afford 7, an intermediate in the synthesis of Ib. Compound 10 may also be generated by oxidation of the amine 2 (e.g. NCS) followed by hydrolysis and subsequent cyanide treatment. Compound 10 may be obtained as a mixture of stereoisomers or a single isomer/diastereomer which may be epimerized (employing conventional procedures) to afford a mixture of stereoisomers.

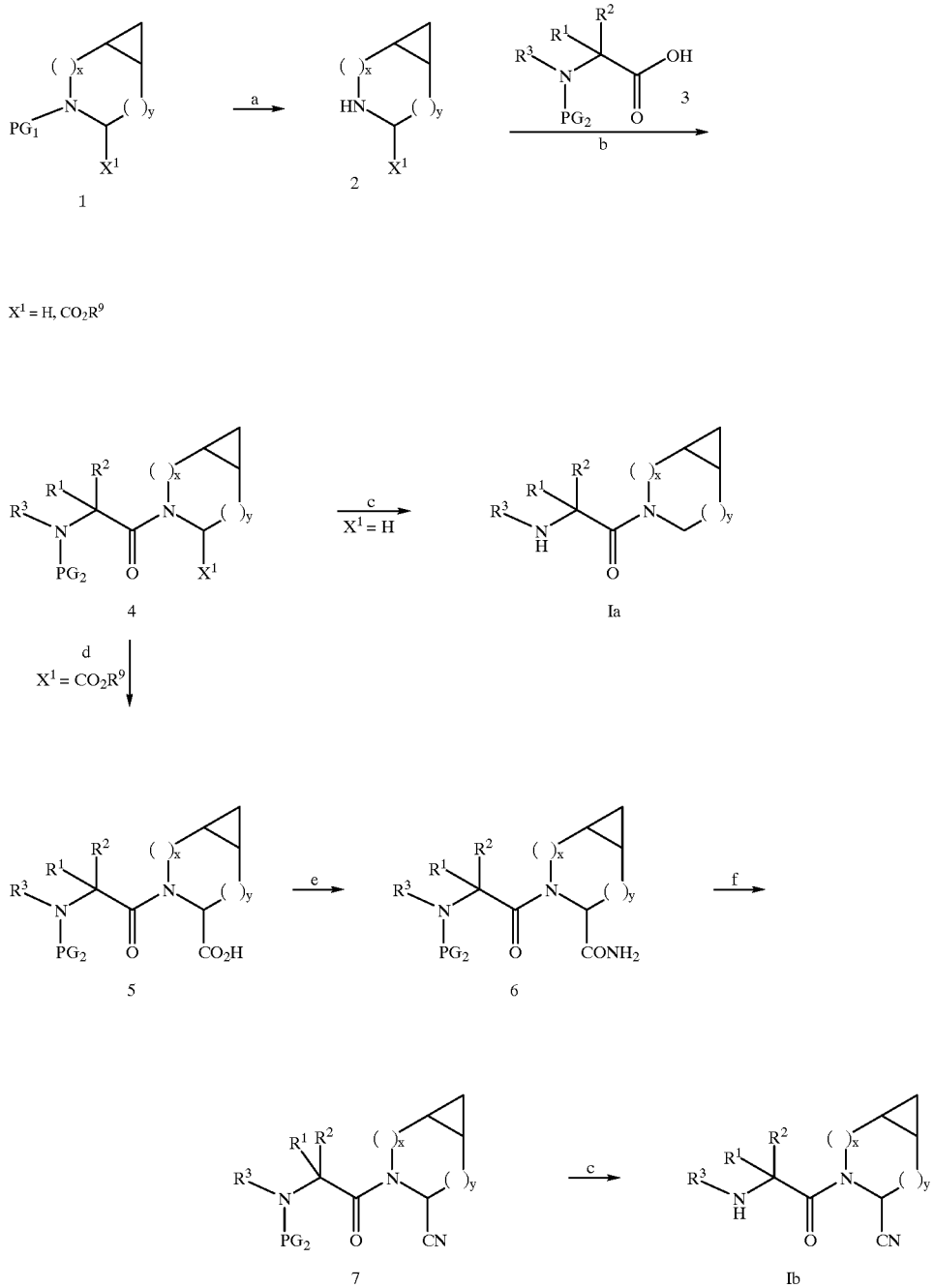

Scheme 1 a. PG$_1$ = Boc, TFA or HCl; PG$_1$ = Cbz, H$_2$/Pd/C or TMSI; PG$_1$ = FMOC, Et$_2$NH b. EDAC, HOBT, DMF or i-BuOCOCl/TEA or PyBop, NMM c. PG$_2$ = PG$_1$, (see conditions for a) d. LiOH or NaOH MeOH or THF/H$_2$O or dioxane e. i-BuOCOCl/NMM or i-BuOCOCl/TEA or EDAC, then NH$_3$ in dioxane or Et$_2$O f. POCl$_3$, pyridine, imidazole or cyanuric chloride, DMF or TFAA, THF, pyridine.

Scheme 2

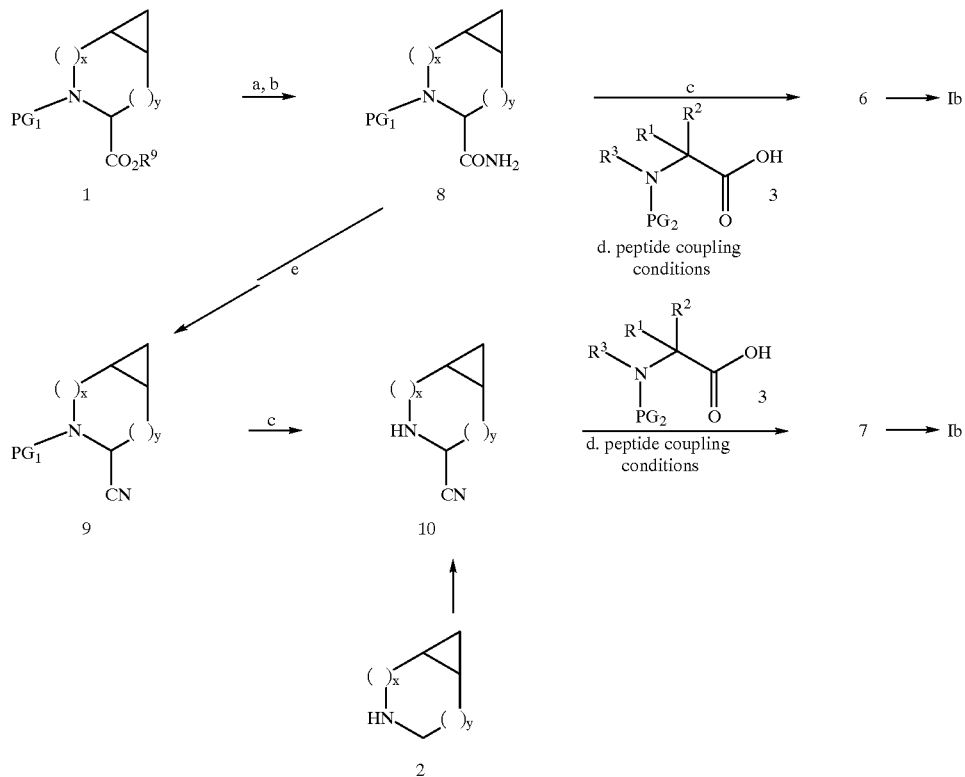

a. LiOH or NaOH in MeOH or THF/H$_2$O or dioxane b. i-BuOCOCl/NMM or i-BuOCOCl/TEA or EDAC, then NH$_3$ in dioxane or Et$_2$O c. PG$_1$ = Boc, TFA or HCl; PG$_1$ = Cbz, H$_2$/Pd/C or TMSI; PG$_1$ = FMOC, Et$_2$NH d. EDAC, HOBT, DMF or i-BuOCOCl/TEA or PyBop, NMM e. POCl$_3$, pyridine, imidazole or cyanuric chloride, DMF.

In a like manner, β-amino acids such as

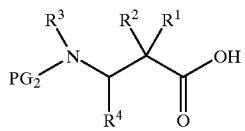

may be coupled with 2, the free amine of 8, or 10 to give the corresponding amides which may be converted to the β-amino acid derivatives of compound Ia or Ib following the same chemistry.

Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups including 1 to 4 substituents such as halo, for example F, Br, Cl or I or CF$_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl (tricycloalkyl), containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl, adamantyl,

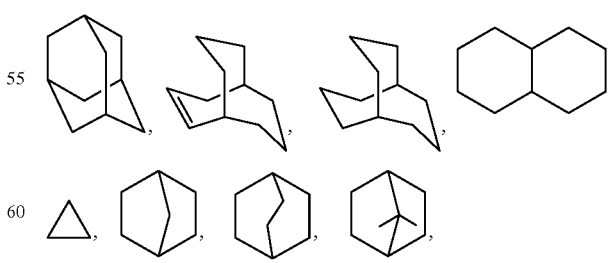

any of which groups may be optionally substituted with 1 to 4 substituents such as halogen, alkyl, alkoxy, hydroxy, aryl, aryloxy, arylalkyl, cycloalkyl, hydroxyalkyl, alkylamido, alkanoylamino, oxo, acyl, arylcarbonylamino, amino, nitro, cyano, thiol and/or alkylthio and/or any of the substituents for alkyl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "cycloalkylene" as employed herein refers to a "cycloalkyl" group which includes free bonds and thus is a linking group such as

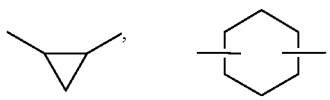

and the like, and may optionally be substituted as defined above for "cycloalkyl".

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio and/or any of the alkyl substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonenyl, 4-decenyl,3-undecenyl, 4-dodecenyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

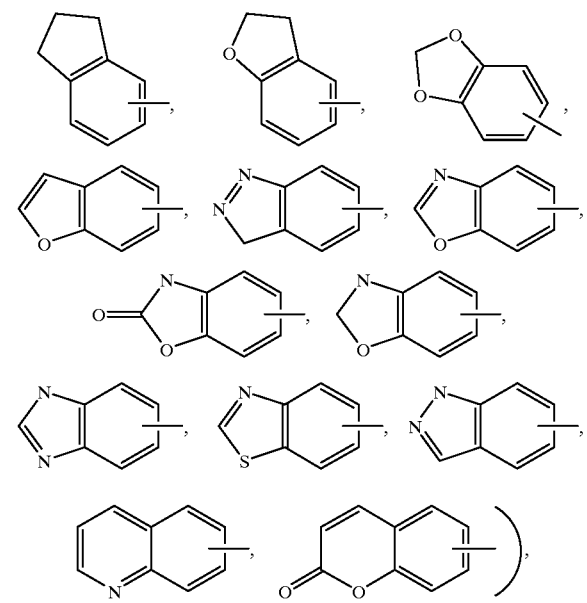

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfon-aminocarbonyl and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl haloalkyl, hydroxyalkyl, alkoxyalkyl or thioalkyl. These substituents may be further substituted with any of the $R^1$ groups or substituents for $R^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", "alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a carbonyl

group; examples of acyl groups include any of the $R^1$ groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_r$ (where r is 1, 2 or 3), such as:

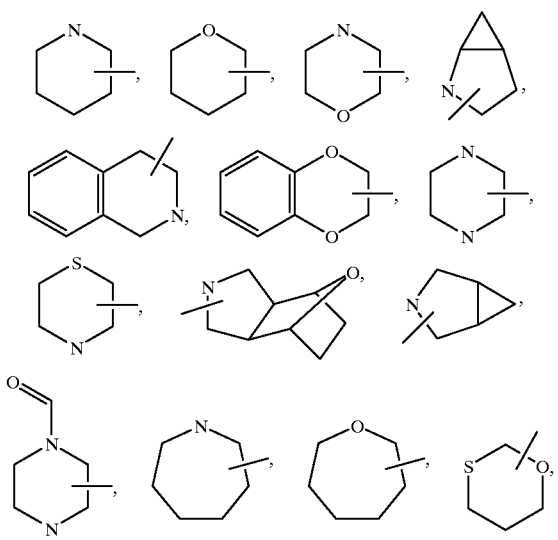

and the like. The above groups may include 1 to 4 substituents such as alkyl, halo, oxo and/or any of the alkyl substituents set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the substituents set out above for alkyl. Examples of heteroaryl groups include the following:

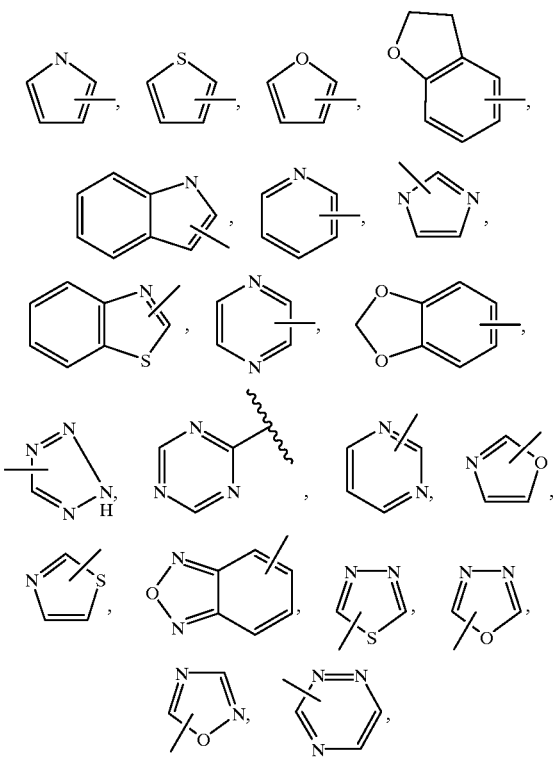

and the like.

The term "cycloheteroalkylalkyl" as used herein alone or as part of another group refers cycloheteroalkyl groups as defined above linked through a atom or heteroatom to a $(CH_2)_r$ chain.

The term "heteroarylalkyl" or "heteroarylalkenyl" as used herein alone or as part of another group refers to a heteroaryl group as defined above linked through a C atom or heteroatom to a —$(CH_2)_r$— chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkoxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

Where desired, the compounds of structure I may be used in combination with one or more other types of antidiabetic agents (employed to treat diabetes and related diseases) and/or one or more other types of therapeutic agents which may be administered orally in the same dosage form, in a separate oral dosage form or by injection.

The other type of antidiabetic agent which may be optionally employed in combination with the DP4 inhibitor of formula I may be 1,2,3 or more antidiabetic agents or antihyperglycemic agents including insulin secretagogues or insulin sensitizers, or other antidiabetic agents preferably having a mechanism of action different from DP4 inhibition and may include biguanides, sulfonyl ureas, glucosidase inhibitors, PPAR γ agonists, such as thiazolidinediones, SGLT2 inhibitors, PPAR α/γ dual agonists, aP2 inhibitors, glycogen phosphorylase inhibitors, advanced glycosylation end (AGE) products inhibitors, and/or meglitinides, as well as insulin, and/or glucagon-like peptide-1 (GLP-1) or mimetics thereof.

It is believed that the use of the compounds of structure I in combination with 1, 2, 3 or more other antidiabetic agents produces antihyperglycemic results greater than that possible from each of these medicaments alone and greater than the combined additive antihyperglycemic effects produced by these medicaments.

The other antidiabetic agent may be an oral antihyperglycemic agent preferably a biguanide such as metformin or phenformin or salts thereof, preferably metformin HCl.

Where the other antidiabetic agent is a biguanide, the compounds of structure I will be employed in a weight ratio to biguanide within the range from about 0.01:1 to about 100:1, preferably from about 0.1:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the γ-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.05:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.2:1 to about 50:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (en), pioglitazone (Takeda), Mitsubishi MCC-555 (disclosed in U.S. Pat. No. 5,594,016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/ NN), or YM-440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.1:1 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1(1-36) amide, GLP-1(7-36) amide, GLP-1(7-36) (as disclosed in U.S. Pat. No. 5,614,492 to Habener, disclosure of which is incorporated herein by reference), or a GLP-1 mimic such as AC2993 or Exendin-4 (Amylin) and LY-315902 or LY-307167 (Lilly) and NN2211 (Novo-Nordisk), which may be administered via injection, intranasal, or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration (for example inhalation spray) or parenterally as described in U.S. Pat. Nos. 5,346,701 (TheraTech), 5,614,492 and 5,631,224 which are incorporated herein by reference.

The other antidiabetic agent may also be a PPAR α/γ dual agonist such as AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998), and in U.S. application Ser. No. 09/664,598, filed Sep. 18, 2000, (attorney file LA29NP) the disclosure of which is incorporated herein by reference, employing dosages as set out therein, which compounds designated as preferred are preferred for use herein.

The other antidiabetic agent may be an SGLT2 inhibitor such as disclosed in U.S. application Ser. No. 09/679,027, filed Oct. 4, 2000 (attorney file LA49NP), which is incorporated herein by reference, employing dosages as set out herein. Preferred are the compounds designated as preferred in the above application.

The other antidiabetic agent which may be optionally employed in combination with the DP4 inhibitor of formula I may be an aP2 inhibitor such as disclosed in U.S. application Ser. No. 09/391,053, filed Sep. 7, 1999, and U.S. application Ser. No. 09/519,079, filed Mar. 6, 2000 (attorney file LA27NP), which is incorporated herein by reference, employing dosages as set out herein. Preferred are the compounds designated as preferred in the above application.

The other antidiabetic agent which may be optionally employed in combination with the DP4 inhibitor of formula I may be a glycogen phosphorylase inhibitor such as disclosed in WO 96/39384, WO 96/39385, EP 978279, WO 2000/47206, WO 99/43663, and U.S. Pat. Nos. 5,952,322 and 5,998,463, WO 99/26659 and EP 1041068.

The meglitinide which may optionally be employed in combination with the compound of formula I of the invention may be repaglinide, nateglinide (Novartis) or KAD1229 (PF/Kissei), with repaglinide being preferred.

The DP4 inhibitor of formula I will be employed in a weight ratio to the meglitinide, PPAR γ agonist, PPAR α/γ dual agonist, SGLT2 inhibitor, aP2 inhibitor, or glycogen phosphorylase inhibitor within the range from about 0.01:1 to about 100:1, preferably from about 0.1:1 to about 10:1.

The hypolipidemic agent or lipid-modulating agent which may be optionally employed in combination with the compounds of formula I of the invention may include 1,2,3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na$^+$/bile acid cotransporter inhibitors, upregulators of LDL receptor activity, ATP citrate lyase inhibitors, cholesteryl ester transfer protein inhibitors, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. Patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246 as well as implitapide (Bayer).

The most preferred MTP inhibitor is 9-[4-[4-[[2-(2,2,2-Trifluoroethoxy)benzoyl]amino]-1-piperidinyl] butyl]-N-(2,2,2-trifluoroethyl)-9H-fluorene-9-carboxamide

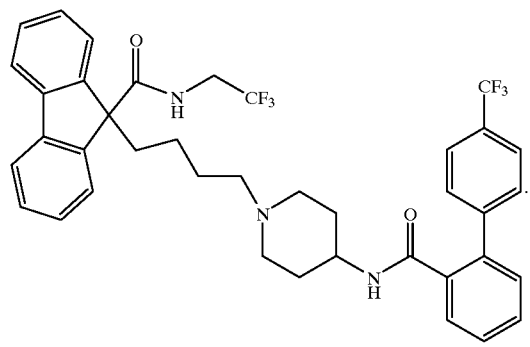

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, atavastatin (Nissan/Sankyo nisvastatin (NK-104)) disclosed in U.S. Pat. No. 5,011,930, Shionogi-Astra/Zeneca visastatin (ZD-4522) disclosed in U.S. Pat. No. 5,260,440.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 11, No. 10, pp 1869–1871, including isoprenoid (phosphinyl-methyl) phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 10, 5544 and cyclopropanes reported by Capson, T. L., PhD dissertation, June, 1987, Dept. Med. Chem. U of Utah, Abstracts Table of Contents, pp 16, 17, 40–43, 48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly (diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor such as disclosed in, Drugs of the Future 24, 9–15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd).

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's SCH48461 as well as those disclosed in Atherosclerosis 115, 45–63 (1995) and J. Med. Chem. 41, 973 (1998).

The hypolipidemic agent may be an ileal Na$^+$/bile acid cotransporter inhibitor such as disclosed in Drugs of the Future, 24, 425–430 (1999).

The lipid-modulating agent may be a cholesteryl ester transfer protein (CETP) inhibitor such as Pfizer's CP 529, 414 (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, atavastatin and ZD-4522.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg/kg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

A preferred oral dosage form, such as tablets or capsules will contain the squalene synthetase inhibitor in an amount of from about 10 to about 500 mg, preferably from about 25 to about 200 mg.

The other hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin.

The other type of therapeutic agent which may be optionally employed with the DP4 inhibitor of formula I may be 1, 2, 1 or more of an anti-obesity agent including a beta 3 adrenergic agonist, a lipase inhibitor, a serotonin (and dopamine) reuptake inhibitor, a thyroid receptor beta drug, an anorectic agent and/or a fatty acid oxidation upregulator.

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may be optionally employed in combination with a compound of formula I may be orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor beta compound which may be optionally employed in combination with a compound of formula I may be a thyroid receptor ligand as disclosed in WO97/21993 (U. Cal SF), WO099/00353 (KaroBio) and GB98/284425 (KaroBio), with compounds of the KaroBio applications being preferred.

The anorectic agent which may be optionally employed in combination with a compound of formula I may be dexamphetamine, phentermine, phenylpropanolamine or mazindol, with dexamphetamine being preferred.

The fatty acid oxidation upregulator which may be optionally employed in combination with the compound of formula I can be famoxin (Genset).

The various anti-obesity agents described above may be employed in the same dosage form with the compound of formula I or in different dosage forms, in dosages and regimens as generally known in the art or in the PDR.

The infertility agent which may be optionally employed in combination with the DP4 inhibitor of the invention may be 1, 2, or more of clomiphene citrate (Clomid®, Aventis), bromocriptine mesylate (Parlodel®, Novartis),LHRH analogs, Lupron (TAP Pharm.), danazol, Danocrine (Sanofi), progestogens or glucocorticoids, which may be employed in amounts specified in the PDR.

The agent for polycystic ovary syndrome which may be optionally employed in combination with the DP4 inhibitor of the invention may be 1, 2, or more of gonadotropin releasing hormone (GnRH), leuprolide (Lupron®), Clomid®, Parlodel®, oral contraceptives or insulin sensitizers such as PPAR agonists, or other conventional agents for such use which may be employed in amounts specified in the PDR.

The agent for treating growth disorders and/or frailty which may be optionally employed in combination with the DP4 inhibitor of the invention may be 1, 2, or more of a growth hormone or growth hormone secretagogue such as MK-677 (Merck), CP-424,391 (Pfizer), and compounds disclosed in U.S. Ser. No. 09/506,749 filed Feb. 18, 2000 (attorney docket LA26), as well as selective androgen receptor modulators (SARMs), which is incorporated herein by reference, which may be employed in amounts specified in the PDR, where applicable.

The agent for treating arthritis which may be optionally employed in combination with the DP4 inhibitor of the invention may be 1, 2, or more of aspirin, indomethacin, ibuprofen, diclofenac sodium, naproxen, nabumetone (Relafen®, SmithKline Beecham), tolmetin sodium (Tolectin®, Ortho-McNeil), piroxicam (Feldene®, Pfizer), ketorolac tromethamine (Toradol®, Roche), celecoxib (Celebrex®, Searle), rofecoxib (Vioxx®, Merck) and the like, which may be employed in amounts specified in the PDR.

Conventional agents for preventing allograft rejection in transplantation such as cyclosporin, Sandimmune (Novartis), azathioprine, Immuran (Faro) or methotrexate may be optionally employed in combination with the DP4 inhibitor of the invention, which may be employed in amounts specified in the PDR.

Conventional agents for treating autoimmune diseases such as multiple sclerosis and immunomodulatory diseases such as lupus erythematosis, psoriasis, for example, azathioprine, Immuran, cyclophosphamide, NSAIDS such as ibuprofen, cox 2 inhibitors such as Vioxx and Celebrex, glucocorticoids and hydroxychloroquine, may be optionally employed in combination with the DP4 inhibitor of the invention, which may be employed in amounts specified in the PDR.

The AIDS agent which may be optionally employed in combination with the DP4 inhibitor of the invention may be a non-nucleoside reverse transcriptase inhibitor, a nucleoside reverse transcriptase inhibitor, a protease inhibitor and/or an AIDS adjunct anti-infective and may be 1, 2, or more of dronabinol (Marinol®, Roxane Labs), didanosine (Videx®, Bristol-Myers Squibb), megestrol acetate (Megace®, Bristol-Myers Squibb), stavudine (Zerit®, Bristol-Myers Squibb), delavirdine mesylate (Rescriptor®, Pharmacia), lamivudine/zidovudine (Combivir™, Glaxo), lamivudine (Epivir™, Glaxo), zalcitabine (Hivid®, Roche), zidovudine (Retrovir®, Glaxo), indinavir sulfate (Crixivan®, Merck), saquinavir (Fortovase™, Roche), saquinovir mesylate (Invirase®, Roche), ritonavir (Norvir®, Abbott), nelfinavir (Viracept®, Agouron).

The above anti-AIDS agents may be employed in amounts specified in the PDR.

The agent for treating inflammatory bowel disease or syndrome which may be optionally employed in combination with the DP4 inhibitor of the invention may be 1, 2, or more of sulfasalazine, salicylates, mesalamine (Asacol®, P&G) or Zelmac®, (Bristol-Myers Squibb), which may be employed in amounts specified in the PDR or otherwise known in the art.

The agent for treating osteoporosis which may be optionally employed in combination with the DP4 inhibitor of the invention may be 1, 2, or more of alendronate sodium (Fosamax®, Merck, tiludronate (Skelid®, Sanofi), etidronate disodium (Didronel®, P&G), raloxifene HCl (Evista®, Lilly), which may be employed in amounts specified in the PDR.

In carrying our the method of the invention, a pharmaceutical composition will be employed containing the compounds of structure I, with or without another antidiabetic agent and/or other type therapeutic agent, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 10 and 1,000 mg per day, which can be administered in a single dose or in the form of individual doses from 1–4 times per day.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

DP4 inhibitor activity of the compounds of the invention may be determined by use of an in vitro assay system which measures the potentiation of inhibition of DP4. Inhibition constants (Ki values) for the DP4 inhibitors of the invention may be determined by the method described below.

Purification of Porcine Dipeptidyl Peptidase IV

Porcine enzyme was purified as previously described (1), with several modifications. Kidneys from 15–20 animals were obtained, and the cortex was dissected away and frozen at −80° C. Frozen tissue (2000 –2500 g) was homogenized in 12 L of 0.25 M sucrose in a Waring blender. The homogenate then was left at 37° C. for 18 hours to facilitate cleavage of DP-4 from cell membranes. After the cleavage step, the homogenate was clarified by centrifugation at 7000×g for 20 min at 4° C., and the supernatant was collected. Solid ammonium sulfate was added to 60% saturation, and the precipitate was collected by centrifugation at 10,000×g and was discarded. Additional ammonium sulfate was added to the supernatant to 80% saturation, and the 80% pellet was collected and dissolved in 20 mM $Na_2HPO_4$, pH 7.4.

After dialysis against 20 mM $Na_2HPO_4$, pH 7.4, the preparation was clarified by centrifugation at 10,000×g. The clarified preparation then was applied to 300 mL of ConA Sepharose that had been equilibrated in the same buffer. After washing with buffer to a constant $A_{280}$, the column was eluted with 5% (w/v) methyl α-D-mannopyranoside. Active fractions were pooled, concentrated, and dialyzed against 5 mM sodium acetate, pH 5.0. Dialyzed material then was flowed through a 100 mL Pharmacia Resource S column equilibrated in the same buffer. The flow through material was collected and contained most of the enzyme activity. Active material again was concentrated and dialyzed into 20 mM $Na_2HPO_4$, pH 7.4. Lastly, the concentrated enzyme was chromatographed on a Pharmacia S-200 gel filtration column to removed low molecular weight contaminants. Purity of column fractions was analyzed by reducing SDS-PAGE, and the purest fractions were pooled and concentrated. Purified enzyme was stored in 20% glycerol at −80° C.

Assay of Porcine Dipeptidyl Peptidase IV

Enzyme was assayed under steady-state conditions as previously described (2) with gly-pro-p-nitroanilide as substrate, with the following modifications. Reactions contained, in a final volume of 100 μl, 100 mM Aces, 52 mM TRIS, 52 mM ethanolamine, 500 μM gly-pro-p-nitroanilide, 0.2 % DMSO, and 4.5 nM enzyme at 25° C., pH 7.4. For single assays at 10 μM test compound, buffer, compound, and enzyme were added to wells of a 96 well microtiter plate, and were incubated at room temperature for 5 min. Reactions were started by addition of substrate, The continuous production of p-nitroaniline was measured at 405 nM for 15 min using a Molecular Devices Tmax plate reader, with a read every 9 seconds. The linear rate of p-nitroaniline production was obtained over the linear portion of each progress curve. A standard curve for p-nitroaniline absorbance was obtained at the beginning of each experiment, and enzyme catalyzed p-nitroaniline production was quantitated from the standard curve. Compounds giving greater than 50% inhibition were selected for further analysis.

For analysis of positive compounds, steady-state kinetic inhibition constants were determined as a function of both substrate and inhibitor concentration. Substrate saturation curves were obtained at gly-pro-p-nitroanilide concentrations from 60 μM to 3600 μM. Additional saturation curves also were obtained in the presence of inhibitor. Complete inhibition experiments contained 11 substrate and 7 inhibitor concentrations, with triplicate determinations across plates. For tight binding inhibitors with $K_i$s less than 20 nM, the enzyme concentration was reduced to 0.5 nM and reaction times were increased to 120 min. Pooled datasets from the three plates were fitted to the appropriate equation for either competitive, noncompetitive or uncompetitive inhibition.

(1) Rahfeld, J. Schutkowski, M., Faust, J., Neubert., Barth, A., and Heins, J. (1991) Biol. Chem. Hoppe-Seyler, 372, 313–318.

(2) Nagatsu, T., Hino, M., Fuyamada, H., Hayakawa, T., Sakakibara, S., Nakagawa, Y., and Takemoto, T. (1976) Anal. Biochem., 74, 466–476.

The following abbreviations are employed in the Examples and elsewhere herein:

Ph=phenyl
Bn=benzyl
i-Bu=iso-butyl
Me=methyl
Et=ethyl
Pr=propyl
Bu=butyl
TMS=trimethylsilyl
FMOC=fluorenylmethoxycarbonyl
Boc or BOC=tert-butoxycarbonyl
Cbz=carbobenzyloxy or carbobenzoxy or benzyloxycarbonyl
HOAc or AcOH=acetic acid
DMF=N,N-dimethylformamide
EtOAc=ethyl acetate
THF=tetrahydrofuran
TFA=trifluoroacetic acid
$Et_2NH$=diethylamine
NMM=N-methyl morpholine
n-BuLi=n-butyllithium
Pd/C=palladium on carbon
$PtO_2$=platinum oxide
TEA=triethylamine
EDAC=3-ethyl-3'-(dimethylamino)propyl-carbodiimide hydrochloride (or 1-[(3-(dimethyl)amino)propyl])-3-ethylcarbodiimide hydrochloride)
HOBT or $HOBT.H_2O$=1-hydroxybenzotriazole hydrate
HOAT=1-hydroxy-7-azabenzotriazole
PyBOP reagent=benzotriazol-1-yloxy-tripyrrolidino phosphonium hexafluorophosphate
min=minute(s)
h or hr=hour(s)
L=liter
mL=milliliter
μL=microliter
g=gram(s)
mg=milligram(s)
mol=mole(s)
mmol=millimole(s)
meq=milliequivalent
rt=room temperature
sat or sat'd=saturated
aq.=aqueous TLC=thin layer chromatography
HPLC=high performance liquid chromatography
LC/MS=high performance liquid chromatography/mass spectrometry
MS or Mass Spec=mass spectrometry
NMR=nuclear magnetic resonance
mp=melting point The following Examples represent preferred embodiments of the invention.

EXAMPLE 1

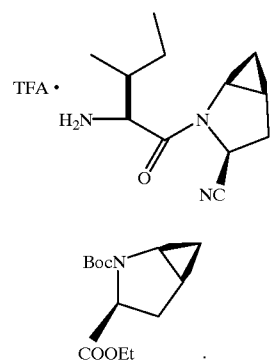

Step 1

Step 1 title compound was synthesized by following the literature procedure [Stephen Hanessian, Ulrich Reinhold, Michel Saulnier, and Stephen Claridge; Bioorganic & Medicinal Chemistry Letters 8 (1998) 2123–2128] or with the following modifications. L-pyroglutamic acid ethyl ester was N-protected as the t-butylcarbamate (Boc$_{2}$O, DMAP or NaH) and then dehydrated to the 4,5-dehydroproline ethyl ester in one pot by carbonyl reduction (triethylborohydride, toluene, −78° C.) followed by dehydration (TFAA, lutidine). The title compound was obtained by cyclopropanation of the 4,5-dehydroproline ethyl ester (Et$_2$Zn, ClCH$_2$I, 1,2-dichloroethane, −15° C.). A more detailed protocol is as follows;

Synthesis of 4,5-dehydro-L-proline ethyl ester: L-pyroglutamic acid ethyl ester (200 g, 1.27 mol) was dissolved in 1.2 liters of methylene chloride and treated sequentially with di-tert-butyldicarbonate (297 g, 1.36 mol) and a catalytic DMAP (1.55 g, 0.013 mol) at ambient temperature. After 6 h, the mixture was quenched with saturated brine and the organic phase was dried (Na$_2$SO$_4$) and filtered through a short silica gel column to give 323 g (100%) of N-Boc- L-pyroglutamic acid ethyl ester. N-Boc-L-pyroglutamic acid ethyl ester (160 g, 0.62 mol) was dissolved in 1 liter of toluene, cooled to −78° C. and treated with lithium triethylborohydride (666 mL of a 1.0 M soln in THF) and added dropwise over 90 minutes. After 3 h, 2,6-lutidine (423 mL, 3.73 mol) was added dropwise followed by DMAP (0.2 g, 0.0016 mol). To this mixture was added TFAA (157 g, 0.74 mol) and the reaction was allowed to come to ambient temperature over 2 h. The mixture was diluted with EtOAc and water and the organics were washed with 3 N HCl, water, aqueous bicarbonate and brine and dried (Na$_2$SO$_4$) and filtered through a silica gel plug to give 165 g of the crude 4,5-dehydroproline ethyl ester that was purified by flash column chromatography on silica gel with 1:5 ethyl acetate:hexanes to give 120 g, 75% of the olefin.

Cyclopropanation of 4,5-dehydro-L-proline ethyl ester: 4,5-Dehydro-L-proline ethyl ester (35.0 g, 0.145 mol) was added to a solution of neat Et$_2$Zn (35.8 g, 0.209 mol) in 1 liter of 1,2-dichloroethane at −15° C. To this mixture was added a dropwise addition of ClCH$_2$I (102 g, 0.58 mol) over 1 h and the mixture stirred at −15° C. for 18 h. The reaction was quenched with saturated aqueous bicarbonate and the solvent was evaporated and the reaction was taken up in EtOAc, washed with brine and purified by silica gel chromatography using a stepwise gradient of from 20% EtOAc/hexanes to 50% EtOAc/hexanes to give 17.5 g (50%) of diastereomerically pure step 1 title compound.

Step 2

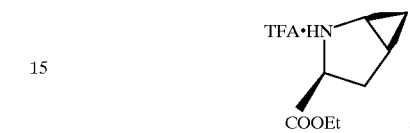

To a stirred solution of Step 1 compound (411 mg, 1.61 mmol) in CH$_2$Cl$_2$ (1.5 mL) at rt was added TFA (1.5 mL). The reaction mixture was stirred at rt for 2 h and evaporated. The residue was diluted with CH$_2$Cl$_2$ and then evaporated and re-evaporated three times to give the title compound as a colorless oil, 433 mg, 100% yield, Step 3

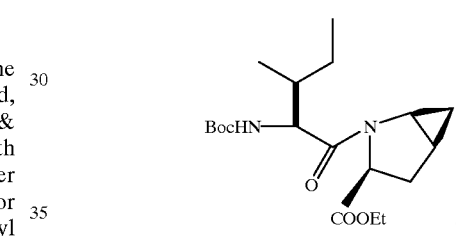

To a stirred solution of (S)-N-tert-butoxycarbonyl-isoleucine (372.6 mg, 1.61 mmol) and benzotriazol-1-yloxytripyrrolidinophosphonium hexafluorophosphate (1.25 g, 2.42 mmol) in CH$_2$Cl$_2$ (6 mL) under nitrogen at rt was added 4-methylmorpholine (NMM) (0.36 mL, 3.2 mmol). After 5 min, a solution of Step 2 compound (433 mg, 1.61 mmol) and NMM (0.27 mL, 2.4 mmol) in CH$_2$Cl$_2$ (1 mL) was added. After addition, the reaction mixture was stirred under nitrogen at room temperature overnight. The reaction mixture was diluted with CH$_2$Cl$_2$ (40 mL) and washed with 4% KHSO$_4$(10 mL), aqueous NaHCO$_3$(10 mL) and brine (10 mL), dried (Na$_2$SO$_4$) and evaporated. Purification by flash chromatography (1:4 EtOAc/hexane) gave the title compound as a colorless oil, 530 mg, 89% yield.

Step 4

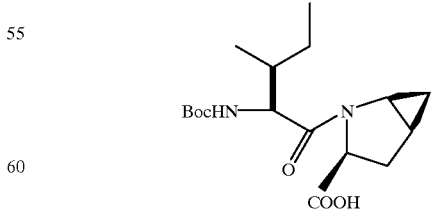

To a stirred solution of Step 3 compound (530 mg, 1.44 mmol) in MeOH (4 mL) and H$_2$O (4 mL) at rt was added LiOH—H$_2$O (91 mg, 2.16 mmol). The reaction mixture was stirred at rt overnight and evaporated. Water (10 mL) was added to the residue and extracted with Et$_2$O (2×10 mL). The aqueous layer was acidified to ~pH 4 by adding 4% KHSO$_4$ dropwise. The milky solution was extracted with EtOAc (15 mL×3). Combined EtOAc layers were washed with brine, dried over Na$_2$SO$_4$ and evaporated to give the title compound as a white solid, 440 mg, 90% yield.

Step 5

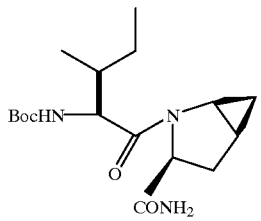

To a stirred solution of Step 4 compound (300 mg, 0.88 mmol) in THF (6 mL) at −15° C. under nitrogen, was added 4-methylmorpholine (0.12 mL, 1.06 mmol) and then isobutyl chloroformate (0.13 mL, 0.97 mmol) over 2 min. White precipitate was formed. The reaction mixture was stirred at −15° C. under nitrogen for 25 min and a solution of NH$_3$ in dioxane (8.8 mL, 4.4 mmol) was added. The reaction mixture was stirred at −15° C. for 30 min, warmed to rt and stirred at rt overnight. The reaction mixture was quenched by 4% KHSO$_4$ to ~pH 4 and extracted with EtOAc (20 mL×3). The extracts were combined, washed with brine (10 mL) dried (Na$_2$SO$_4$) and evaporated. Purification by flash column chromatography (1:1 EtOAc/hexane) gave the title compound as a white foam, 268 mg, 90% yield.

Step 6

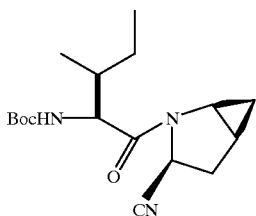

To a stirred solution of Step 5 compound (248 mg, 1.38 mmol) and imidazole (94 mg, 1.38 mmol) in dry pyridine (12 mL) at −35° C. under nitrogen was added POCl$_3$ (0.26 mL, 2.76 mmol) dropwise. The reaction mixture was stirred between −35° C. to −20° C. for 1 h and evaporated. CH$_2$Cl$_2$ (10 mL) was added and white precipitates were formed. After filtration, the filtrate was concentrated and purified by flash chromatography (2:5 EtOAc/hexane) to give the title compound as a colorless oil, 196 mg, 88% yield.

Step 7

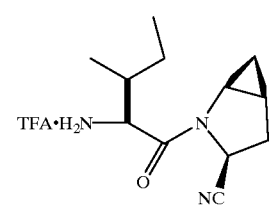

To a stirred solution of Step 6 compound (130 mg, 0.4 mmol) in CH$_2$Cl$_2$ (2 mL) at rt was added TFA (2 mL). The reaction mixture was stirred at rt for 2 h. The reaction mixture was added slowly to a pre-cooled slurry of NaHCO$_3$ (3.8 g) in H$_2$O (3 mL). The mixture was extracted with CH$_2$Cl$_2$ (6 mL×5), and the. combined CH$_2$Cl$_2$ layers were evaporated and purified by preparative HPLC to give the title compound as a white powder, 77 mg. 57% yield, mp=141–143° C. LC/MS gave the correct molecular ion [(M+H)$^+$=222] for the desired compound.

EXAMPLE 2

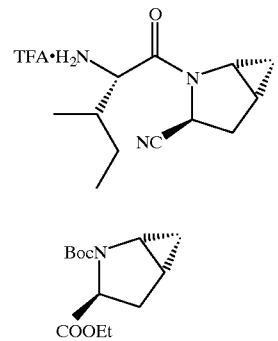

Step 1

Step 1 title compound was synthesized by following the literature procedure. [Stephen Hanessian, Ulrich Reinhold, Michel Saulnier, and Stephen Claridge; Bioorganic & Medicinal Chemistry Letters 8 (1998) 2123–2128.]

Step 2

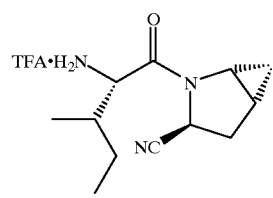

The title compound was prepared from Step 1 compound, employing the same procedure as that described for Example 1, Steps 2–6. LC/MS gave the correct molecular ion [(M+H)$^+$=222] for the desired compound.

EXAMPLE 3

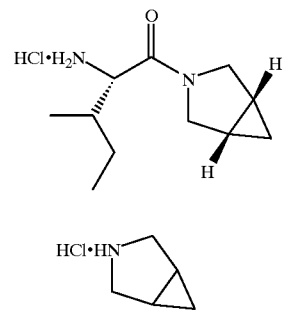

Step 1

Step 1 title compound was prepared by following the literature procedure. [Willy D. Kollmeyer, U.S. Pat. No. 4,183,857.].

Step 2

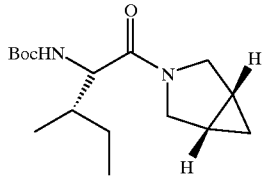

To a stirred solution of (S)-N-tert-butoxycarbonyl-isoleucine (231 mg, 1 mmol) and benzotriazol-1-yloxytripyrrolidinophosphonium hexafluorophosphate (780 mg, 1.5 mmol) in $CH_2Cl_2$ (6 mL) under nitrogen at rt was added 4-methylmorpholine (0.33 mL, 3 mmol). After 5 min, Step 1 compound (120 mg, 1 mmol) was added in one portion. The reaction mixture was stirred under nitrogen at rt overnight and then diluted with $CH_2Cl_2$ (30 mL), washed with 4.1w $KHSO_4$ (10 mL)), aqueous $NaHCO_3$ (10 mL), brine (10 mL), dried ($Na_2SO_4$) and evaporated. Purification by flash chromatography on silica gel (2.4×20 cm column, 1:3 EtOAc/hexane) gave the title compound as a colorless oil, 290 mg, 90% yield. LC/MS gave the correct molecular ion $[(M+H)^+=297]$ for the desired compound.

Step 3

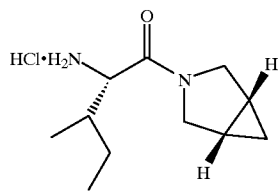

The reaction mixture of Step 2 compound (220 mg, 0.74 mmol) and 4 M HCl in dioxane (1.5 mL, 6 mmol) was stirred at rt for 2 h and evaporated under reduced pressure. $Et_2O$ was added to the residue and a precipitate was formed. $Et_2O$ was decanted and this was done three times. The precipitate was dried in vacuo to give the title compound as a white powder, 130 mg (76% yield), mp 205–206° C. LC/MS gave the correct molecular ion $[(M+H)^+197]$ for the desired compound.

EXAMPLES 4–4A

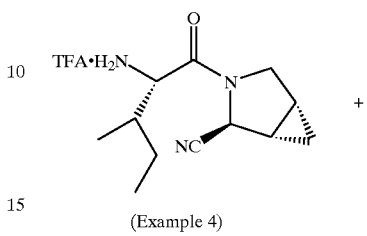

(Example 4)

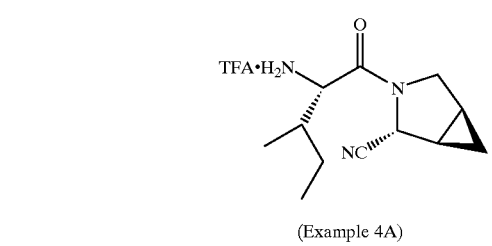

(Example 4A)

Step 1

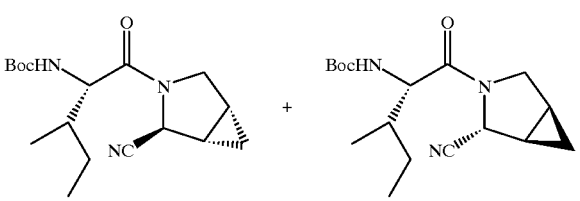

Step 1 title compound, as a 1:1 ratio of enantiomers, was prepared by following the literature procedure. [Willy D. Kollmeyer, U.S. Pat. No. 4,183,857.]

Step 2

A slurry of (S)-N-tert-butoxycarbonyl-isoleucine (92.5 mg, 0.4 mmol), 1-[(3-(dimethyl)amino)propyl]-3-ethylcarbodiimide (77 mg, 0.4 mmol) and HOAT (54.4 mg, 0.4 mmol) in $ClCH_2CH_2Cl$ (0.3 mL) was stirred under nitrogen at rt for 1 h, then Step 1 compound (22 mg, 0.2 mmol) was added, followed by $Et_3N$ (0.015 mL, 0.1 mmol). The reaction mixture was stirred under nitrogen at rt over night and then diluted with $CH_2Cl_2$ (3 mL), washed with $H_2O$ (1 mL), aqueous $NaHCO_3$(1 mL) and brine (1 mL), dried ($Na_2SO_4$) and evaporated. Purification by flash chromatography on silica gel (2.4×12 cm column, 2:7 EtOAc/hexane) gave the title compound as a colorless oil, 33 mg, 51% yield. LC/MS gave the correct molecular ion [(M+H)$^+$ 322] for the desired compound.

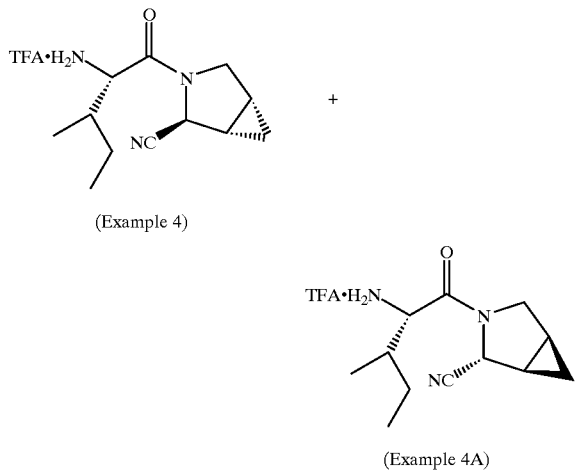

(Example 4)

(Example 4A)

To a stirred solution of Step 2 compound (30 mg, 0.4 mmol) in $CH_2Cl_2$ (0.5 mL) at rt was added TFA (0.5 mL). The reaction mixture was stirred at rt for 2 h. The reaction mixture was added slowly to a precooled slurry of $NaHCO_3$ (0.8 g) in $H_2O$ (1 mL). The mixture was extracted with $CH_2Cl_2$ (2 mL×5), and combined $CH_2Cl_2$ layers were evaporated and purified by preparative HPLC to give the title compounds as a 1:1 ratio of diastereomers, 22 mg, 73% yield. LC/MS gave the correct molecular ion [(M+H)$^+$=222] for the desired compounds.

EXAMPLES 5–5A

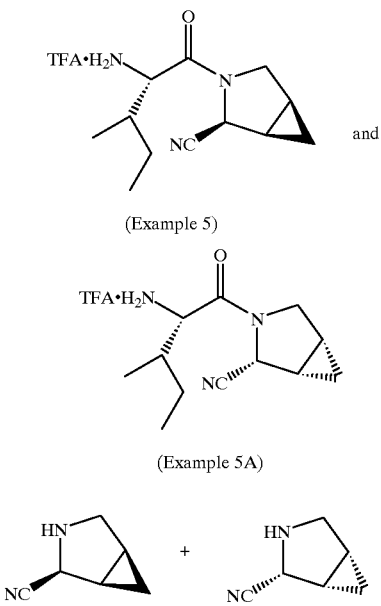

(Example 5)

(Example 5A)

Step 1

To a solution of Example 4, Step 1 compound (150 mg, 1.39 mmol) in 2-propanol (0.8 mL), was added NaCN (40 mg, 1.0 mmol). The reaction mixture was heated to reflux for 3 h. After cooling to rt, the reaction mixture was evaporated and then slurried in $Et_2O$ (5 mL). After filtration, the filtrate was evaporated to give Example 4 Step 1 compounds and Example 5 Step 1 compounds (140 mg, 93%) as a 2:1 mixture of diastereomers, each as a racemic mixture.

Step 2

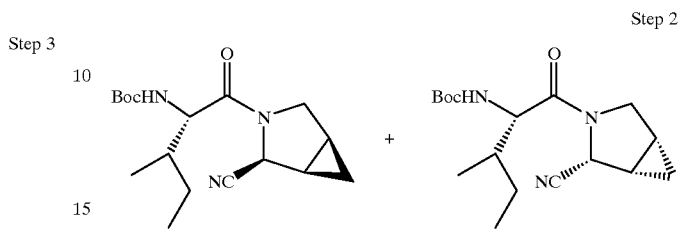

A slurry of (S)-N-tert-butoxycarbonyl-isoleucine (595 mg, 2.57 mmol), 1-[(3-(dimethyl)amino)propyl]-3-ethylcarbodiimide (493 mg, 2.57 mmol) and 1-hydroxy-7-azabenzotriazole (350 mg, 2.57 mmol) in $ClCH_2CH_2Cl$ (2 mL) was stirred under nitrogen at rt for 1 h, then Step 1 compound mixture (139 mg, 1.28 mmol) was added. The reaction mixture was stirred under nitrogen at rt overnight and then diluted with $CH_2Cl_2$ (30 mL), washed with $H_2O$ (10 mL), saturated aqueous $NaHCO_3$ (10 mL) and brine (10 mL), dried ($Na_2SO_4$) and evaporated. Purification by flash chromatography on silica gel (2.4×20 cm column, 1:3 EtOAc/hexane) gave the Example 4, Step 2 compound (260 mg), and the title compounds (105 mg) as a ratio of 1:1 diastereomers. LC/MS gave the correct molecular ion [(M+H)$^+$=322] for the desired compounds.

Step 3

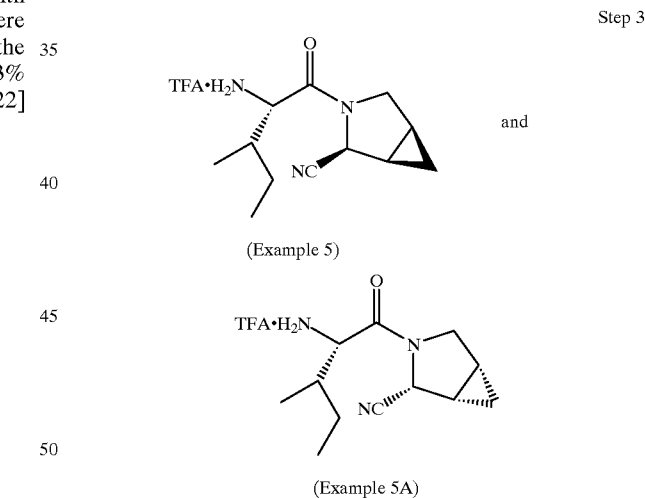

(Example 5)

(Example 5A)

To a stirred solution of Step 2 compounds (104 mg, 0.32 mmol) in $CH_2Cl_2$ (1 mL) at rt was added TFA (1 mL). The reaction mixture was stirred at rt for 2 h. The reaction mixture was added slowly to a precooled slurry of $NaHCO_3$ (2 g) in $H_2O$ (2 mL). The mixture was extracted with $CH_2Cl_2$ (4 mL×4), and combined $CH_2Cl_2$ layers were evaporated and purified by preparative HPLC to give the title compound Example 5 (36 mg) and Example 5A (36 mg). LC/MS gave the correct molecular ion [(M+H)$^+$222] for the desired compounds.

EXAMPLE 6

General Method A: Parallel array synthesis methods for preparation of inhibitors from commercially available amino acids. As shown in Scheme 3, the ester 11, described in Example 1 Step 1, was saponified to the acid with LiOH in THF/HO and converted to the amide 12 by treatment with isobutyl chloroformate/NMM followed by ammonia in dioxane. The Boc protecting group was removed under acidic conditions using TFA in methylene chloride to give 13. The TFA salt was coupled to Boc-t-butylglycine using either EDAC/HOBT/DMF or EDAC/DMAP/CH2cl₂ to give 14. The amide was dehydrated to the nitrile 15 using POCl₃/imidazole in pyridine at −20° C. and finally deprotected with TFA in CH₂Cl₂ at ambient temperature to afford the target 16. SCHEME 3, GENERAL METHOD (EXAMPLES 6–27)

Scheme 3
General Method A (Examples 6–27)

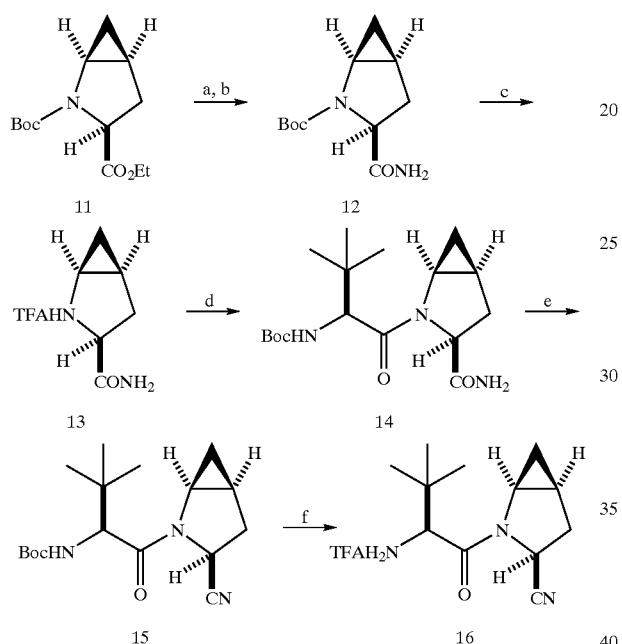

a. LiOH in THF/H₂O or MeOH/H₂O b. i-BuOCOCl/NMM or i-BuOCOCl/TEA at -30 C or EDAC, then NH₃ in dioxane or Et₂O at RT c. TFA, CH₂Cl₂, RT d. Boc-t-butylglycine and PyBop/NMM or EDAC, DMAP, CH₂Cl₂ e. POCl₃, pyridine, imidazol, -20 C f. TFA, CH₂Cl₂, RT

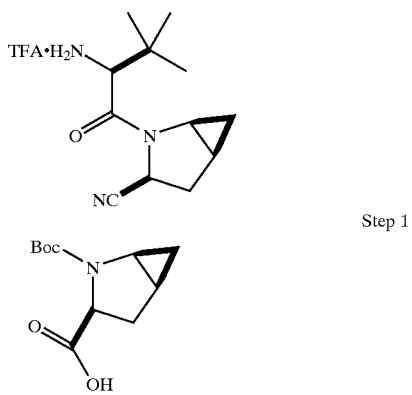

Step 1

To a stirred solution of Example 1 Step 1 compound (1.40 g, 5.49 mmol) in 40 mL of a 1:1 methanol:water solution at rt was added lithium hydroxide (0.20 g, 8.30 mmol). The reaction mixture was stirred at rt for 18 h and then heated to 50° C. for 2 h. The mixture was diluted with equal volumes of ether and water (50 mL) and then acidified with KHSO₄ to pH 3. The milky solution was extracted with ether (3×20 mL). The combined ether layers were dried over Na₂SO₄ and evaporated. The residue was stripped from toluene (2×10 mL) and dried under reduced pressure to give the title compound as a thick syrup, 1.20 g, 96%.

Step 2

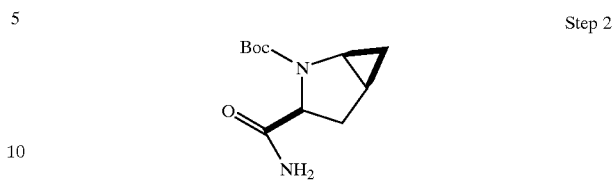

To a stirred solution of Step 1 compound (1.20 g, 5.28 mmol) in THF (20 mL) at −15° C. under nitrogen was added 4-methylmorpholine (0.71 mL, 6.50 mmol) and then isobutyl chloroformate (0.78 mL, 6.00 mmol) over 5 min. The reaction was stirred at −15° C. for 30 min, cooled to −30° C. and treated with a solution of NH₃ in dioxane (50 mL, 25 mmol). The reaction mixture was stirred at −30° C. for 30 min, warmed to rt and stirred overnight. The reaction mixture was quenched with citric acid solution (pH 4) and extracted with ether (3×50 mL). The combined organic fractions were washed with brine, dried over Na₂SO₄ and concentrated. Purification by flash column chromatography on silica gel with EtOAc gave the Step 2 compound, 1.00 g, 84%.

Step 3

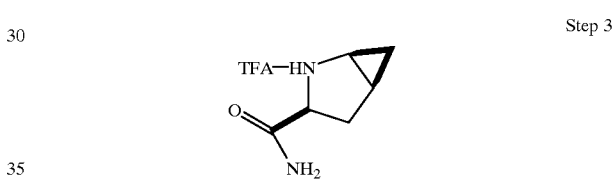

To a stirred solution of Step 2 compound (0.90 g, 4.00 mmol) in CH₂Cl₂ (3 mL) at 0° C. was added TFA (3 mL). The reaction mixture was stirred at 0° C. for 18 h. The reaction mixture was concentrated under reduced pressure to produce title compound in the form of a thick oil, 0.98 g, 100%. The oil gradually solidified upon prolonged standing.

Step 4

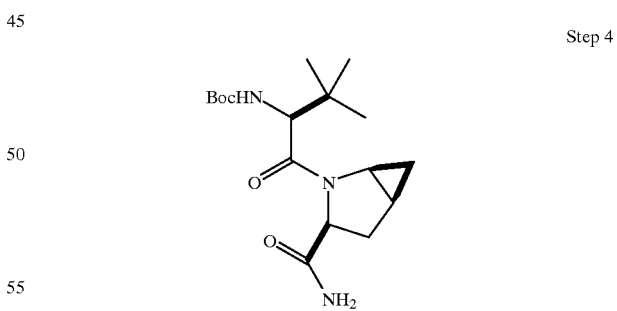

An oven-dried 15-mL test tube was charged with Step 3 compound (56 mg, 0.22 mmol), N-tert-butoxycarbonyl-(L)-tert-leucine (53 mg, 0.23 mmol), dimethylaminopyridine (0.11 g, 0.88 mmol), and CH₂Cl₂ (4 mL). The tube was sealed under nitrogen atmosphere and treated with 1-[(3-(dimethyl)amino)propyl]-3-ethylcarbodiimide (84 mg, 0.44 mmol). The mixture was placed in a shaker and vortexed overnight. The product was purified by solid phase extraction using a United Technology SCX column (2 g of sorbent in a 6 mL column) by loading the material on a SCX ion exchange column and successively washing with $CH_2Cl_2$ (5 mL), 30% methanol in $CH_2Cl_2$ (5 mL), 50% methanol in $CH_2Cl_2$ (5 mL) and methanol (10 mL). The product containing fractions were concentrated under reduced pressure to give the desired amide. Further purification by reverse phase preparative column chromatography on a YMC S5 ODS 20×250 mm column gave the title compound, 50 mg (68% yield). Purification conditions: Gradient elution from 30% methanol/water/0.1 TFA to 90% methanol/water/0.1 TFA over 15 min. 5 min. hold at 90% methanol/water/0.1 TFA. Flow rate: 20 mL/min. Detection wavelength: 220. Retention Time: 14 min.

Step 5

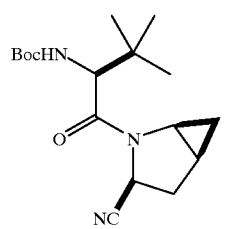

An oven-dried 15-mL test tube was charged with Step 4 compound (50 mg, 0.15 mmol), imidazole (31 mg, 0.46 mmol), and pyridine (1 mL). The tube was sealed under nitrogen atmosphere and cooled to −30° C. Slow addition of $POCl_3$ (141 mg, 88 uL, 0.92 mmol) gave after mixing a thick slurry. The tube was mixed at −30° C. for 3 h and the volatiles evaporated. The product was purified by solid phase extraction using a United Technology silica extraction column (2 g of sorbent in a 6 mL column) by loading the material on a silica column and successively washing with $CH_2Cl_2$ (5 mL), 5% methanol in $CH_2Cl_2$ (5 mL), 7% methanol in $CH_2Cl_2$ (5 mL) and 12% methanol in $CH_2Cl_2$ (10 mL). The product containing fractions were pooled and concentrated under reduced pressure to give the title compound, 46 mg, 96%.

Step 6

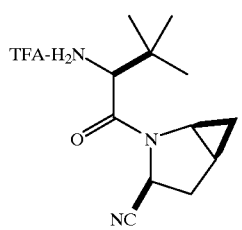

An oven-dried 15-mL test tube was charged with Step 5 compound (0.45 mg, 0.14 mmol), $CH_2Cl_2$ (1 mL), and TFA (1 mL). The reaction mixture was vortexed for 40 min at rt, diluted with toluene (4 mL) and concentrated under reduced pressure to a thick oil. The product was purified by reverse phase preparative column chromatography on a YMC S5 ODS 20×250 mm column to give the Example 6 compound, 14 mg, 35%. Purification conditions: gradient elution from 10% methanol/water/0.1 TFA to 90% methanol/water/0.1 TFA over 18 min; 5 min hold at 90% methanol/water/0.1 TFA. Flow rate: 20 mL/min. Detection wavelength: 220. Retention Time: 10 min.

Examples 7–27 were prepared from amino acids available from commercial sources according to the procedure in Example 6.

TABLE 1

| Example | R | [M + H] |
|---|---|---|
| 7 | | 302 |
| 8 | | 295 |
| 9 | | 240 |
| 10 | | 222 |
| 11 | | 222 |
| 12 | | 222 |
| 13 | | 208 |
| 14 | | 270 |

TABLE 1-continued

| Example | R | [M + H] |
|---|---|---|
| 15 | (2-amino-3-methylpentanoyl) | 222 |
| 16 | (prolyl) | 206 |
| 17 | (phenylalanyl) | 256 |
| 18 | (S-tert-butylcysteinyl) | 268 |
| 19 | (pipecolinyl) | 220 |
| 20 | (3-methylprolyl) | 220 |
| 21 | (isoleucyl isomer) | 210 |
| 22 | (2-amino-3-cyclohexylpropanoyl) | 262 |
| 23 | (2-amino-2-phenylacetyl) | 242 |
| 24 | (isoleucyl) | 210 |
| 25 | (2-amino-3-(3-cyanophenyl)propanoyl) | 281 |
| 26 | (2-amino-3-(4-cyanophenyl)propanoyl) | 281 |
| 27 | (tyrosyl) | 272 |

EXAMPLE 27

-continued

Step 1

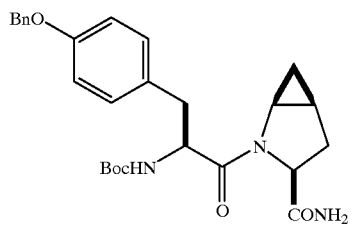

(2S,4S,5S)-4,5-methano-L-proline carboxylamide, TFA salt (53 mg, 0.22 mmol) was coupled to N-Boc-L-Tyrosine-benzyl ether (82 mg, 0.22 mmol) using PyBop (172 mg, 0.33 mmol) and N-methylmorpholine (67 mg, 0.66 mmol) in 4 mL $CH_2Cl_2$. The reaction stirred for 16 h, was taken up in EtOAc, washed with $H_2O$, 1N aqueous HCl, brine, then evaporated and purified by silica gel flash chromatography to give the coupled product (FAB MH+480).

Step 2

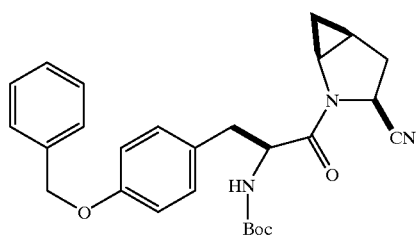

The Step 1 amide was dehydrated to the nitrile using the general method C (which follows Example 29) (FAB MH+462).

Step 3

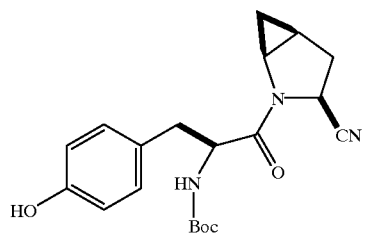

The Step 2 benzyl ether was cleaved by catalytic hydrogenolysis using 10% palladium on carbon and 1 atmosphere hydrogen gas in MeOH at rt for 1.5 h. The reaction was filtered through celite and concentrated to an oil and taken on without further purification (FAB MH+372).

Step 4

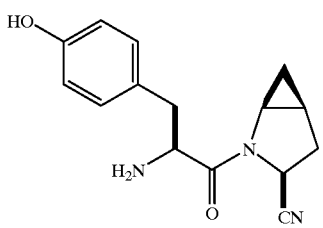

Step 3 N-[N-Boc-L-Tyrosine-]-(2S,4S,5S)-2-cyano-4,5-methano-L-prolylamide was dissolved in $CH_2Cl_2$ and TFA was added at rt. The reaction stirred for 1 h and was evaporated and purified by preparative HPLC as described in general method B (set out following Example 29) to afford the title compound (FAB MH+272).

EXAMPLE 28

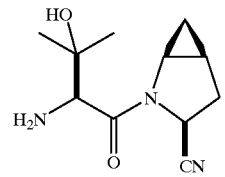

The title compound was prepared by coupling (2S,4S, 5S)-4,5-methano-L-proline carboxylamide, TFA salt described in Example 6 Step 3 compound with N-(tert-butyloxy-carbonylhydroxyvaline. After hydroxyl protection with triethylsilyl chloride and dehydration of the amide with $POCl_3$/imidazole in pyridine and deprotection (N-terminal nitrogen and valine hydroxyl) with TFA using general method C (FAB MH+224), the title compound was obtained.

EXAMPLE 29

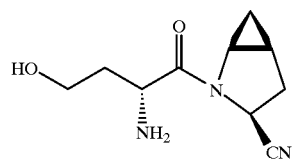

Step 1

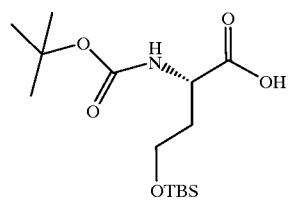

N-Boc-L-homoserine (1.20 g, 5.47 mmol) upon treatment with tert-butyldimethylsilyl chloride (1.67 g, 11.04 mmol) and imidazole (938 mg, 13.8 mmol) in THF (17 mL) was stirred as thick slurry for 48 h under $N_2$. The solvent was evaporated, and the crude material was dissolved in MeOH (10 mL). The resulting solution was stirred at rt for 2 h. The solvent was evaporated, and the crude material was diluted with $CH_2Cl_2$ (50 mL) and treated with 0.1N HCl (2×10 mL). The $CH_2Cl_2$ layer was washed with brine and dried over $MgSO_4$. Removal of the volatiles gave title compound as an oil (1.8 g), which was used without further purification (LC/Mass, + ion): 334 (M+H).

Step 2

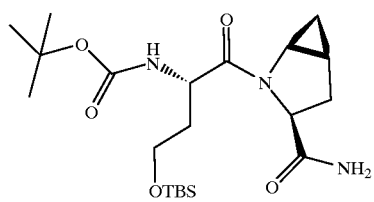

To a stirred solution of Step 1 compound (333 mg, 1.0 mmol) in 6 mL of CH$_2$Cl$_2$ was added 1-[3-(dimethylamino)-propyl]-3-ethylcarbodiimide hydrochloride (256 mg, 1.32 mmol). The solution was then stirred at rt for 30 min, followed by addition with Example 6 Step 3 amine TFA salt (160 mg, 0.66 mmol) and 4-(dimethylamino)pyridine (244 mg, 2.0 mmol). The solution was then stirred at rt overnight. The mixture was diluted with CH$_2$Cl$_2$ (5 mL) and washed sequentially with H$_2$O, 10% citric acid, brine, then dried over Na$_2$SO$_4$ and evaporated to give the title compound (350 mg) which was used without further purification (LC/Mass, + ion): 442 (M+H).

Step 3

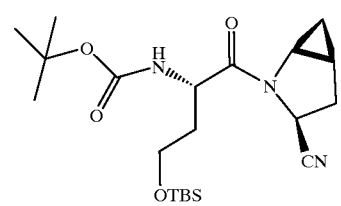

An oven-dried 10-mL round bottomed flask was charged with Step 2 compound (350 mg, 0.79 mmol), imidazole (108 mg, 1.58 mmol), pyridine (3 mL). The flask under argon was cooled to −30° C. Slow addition of POCl$_3$ (0.30 mL, 3.16 mmol) gave after mixing a thick slurry. The slurry was mixed at −30° C. for 3 h and the volatiles evaporated. Dichloromethane (5 mL) was then added and the insoluble solid was removed by filtration. The organic layer was a washed with H$_2$O, 10% citric acid, brine and dried over a Na$_2$SO$_4$. Removal of solvent gave crude desired nitrile (330 mg) (LC/Mass, + ion): 424 (M+H).

Step 4

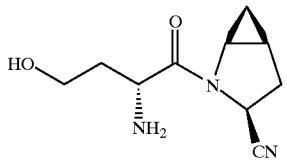

Trifluoroacetic acid (3.3 mL) was added to a stirred solution of Step 3 compound (330 mg, 0.58 mmol) in 3.3 mL CH$_2$Cl$_2$. The solution was then stirred at rt for 30 min, a few drops of water were added and the mixture mixture stirred for 0.5 h. The mixture was diluted with CH$_2$Cl$_2$ (5 mL) and concentrated under reduced pressure to a thick oil. The product was purified by reverse phase preparative column chromatography on a YMC S5 ODS 20×100 mm column to give the title compound, 59 mg, 17%. Purification conditions: gradient elution from 10% methanol/water/0.1 TFA to 90% methanol/water/ 0.1 TFA over 15 min; 5 min hold at 90% methanol/water/0.1 TFA. Flow rate: 20 mL/min. Detection wavelength: 220. Retention Time 10 Min. (LC/Mass, + ion): 210 (M+H).

General Method B: Claisen rearrangement sequence to Boc-protected amino acids.

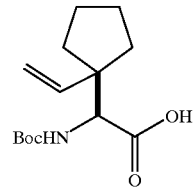

General method B affords the quaternary Boc-protected amino acids. Examples 30–47 contain the vinyl sidechain by coupling amino acids of which Scheme 4, compound 20 is representative. Cyclopentanone was olefinated under Horner-Emmons conditions to afford 17 which was reduced to the allylic alcohol 18 using DIBAL-H in toluene −78° C. to rt. Allylic alcohol 18 was esterified with N-Boc glycine using DCC/DMAP in CH$_2$Cl$_2$ to give 19. Glycine ester 19 was subjected to a Lewis acid mediated Claisen rearrangement by complexation with anhydrous zinc chloride and deprotonation at −78° C. with lithium diisopropylamide followed by warming to ambient temperature to afford 20.

Scheme 4
General Method B, Examples 30–47

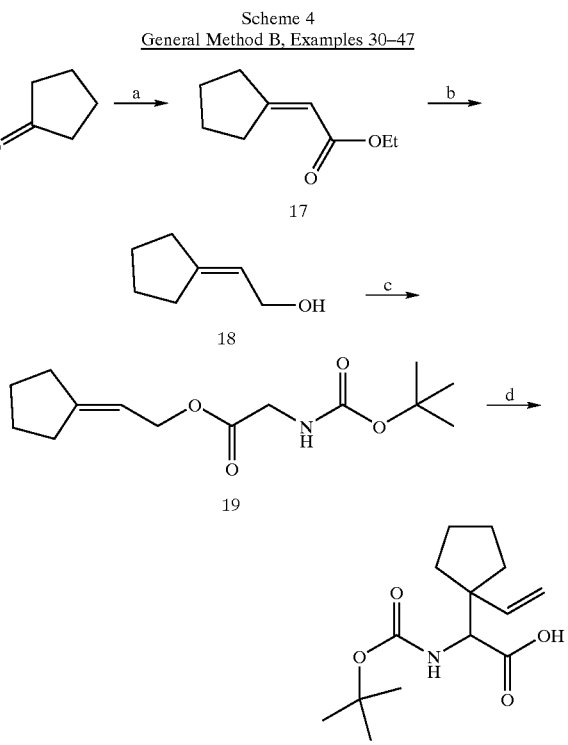

a. Triethylphosphonoacetate, NaH, THF 0 C to RT b. DIBAL-H, toluene, −78 C. to RT c. N-Boc glycine, DCC, DMAP, CH$_2$Cl$_2$, RT
d. ZnCl$_2$, THF, LDA, -78 C. to RT Step 1

Cyclopentylideneacetic Acid Ethyl Ester

To a flame-dried 500-mL round-bottomed flask containing NaH (5.10 g of a 60% dispersion in mineral oil, 128 mmol, 1.10 equiv) in 120 mL anhydrous THF at 0° C. under argon was added triethylphosphonoacetate (25.6 mL, 128 mmol, 1.10 equiv) dropwise through an addition funnel. The mixture was allowed to warm to rt, stirring for an additional 1 h. A solution of cyclopentanone (10.3 mL, 116 mmol) in 10 mL anhydrous THF was added dropwise over 20 min through an addition funnel, and the mixture was allowed to stir at rt for 2.5 h. Ether (200 mL) and water (100 mL) were then added, and the layers were separated. The organic phase was washed successively with water (100 mL) and brine (100 mL), dried ($Na_2SO_4$), and concentrated under reduced pressure, giving 17.5 g (98%) of the desired ester as a colorless oil.

Step 2

2-Cyclopentylideneethanol

To a flame-dried 500-mL round-bottomed flask containing cyclopentylideneacetic acid ethyl ester (17.5 g, 113 mmol) in 100 mL anhydrous toluene at –78° C. under argon was added DIBAL-H (189 mL of a 1.5 M solution in toluene, 284 mmol, 2.50 equiv) dropwise over a 30 min period through an addition funnel, and the mixture was then allowed to warm to rt, stirring for 18 h. The reaction mixture was then recooled to –78° C., and quenched by the careful addition of 30 mL anhydrous MeOH. Upon warming to rt, 1 N Rochelle's salt (100 mL) was added, and the mixture was stirred 90 min. The biphasic reaction mixture was then diluted with $Et_2O$ (200 mL) in a separatory funnel, and the layers were separated. The organic layer was then washed with brine (100 mL), dried ($Na_2SO_4$), and concentrated under reduced pressure. Purification by flash column E chromatography (silica gel, $CH_2Cl_2$/EtOAc, 10:1) gave 11.6 g (92%) of the desired allylic alcohol as a colorless oil.

Step 3

(2-Cyclopentylideneethyl)-N-(tert-Butyloxycarbonyl) glycinate

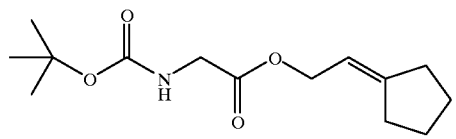

To a flame-dried 500-mL round-bottomed flask containing N-(tert-butyloxycarbonyl)glycine (13.45 g, 76.75 mmol) in 100 mL $CH_2Cl_2$ at rt was added Step 2 compound 48.61 g, 76.75 mmol, 1.00 equiv) in 20 mL $CH_2Cl_2$, followed by dicyclohexylcarbodiimide (16.63 g, mmol, 1.05 equiv) in 80 mL $CH_2Cl_2$. To this reaction mixture was then added 4-dimethylaminopyridine (0.94 mg, mmol, 0.10 equiv), and the mixture was allowed to stir overnight. The reaction mixture was then filtered through a medium sintered-glass funnel, rinsing with 100 mL $CH_2Cl_2$, and concentrated under reduced pressure. The crude product was then purified by flash chromatography (silica gel, hexanes/EtOAc, 20:1 to 1:1 gradient) to give 19.43 g (94%) of the desired glycinyl ester as a colorless oil.

Step 4

N-(tert-Butyloxycarbonyl)(1'vinylcyclopentyl)-glycine

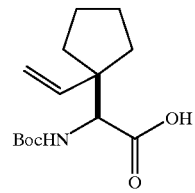

A flame-dried 500-mL round-bottomed flask under argon was charged with $ZnCl_2$ (11.8 g, mmol, 1.20 equiv) and 20 mL toluene. The mixture was heated under vacuum with vigorous stirring to azeotrope off any traces of moisture with the distilling toluene, repeating this process (2 ×). The flask was then cooled to rt under argon, (2-cyclopentylideneethyl) N-(tert-butyloxycarbonyl)glycinate (19.36 g, 71.88 mmol) was added via cannula as a solution in 180 mL THF, and the mixture was then cooled to –78° C. In a separate flame-dried 200-mL round-bottomed flask containing diisopropylamine (26.3 mL, mmol, 2.60 equiv) in 90 mL THF at –78° C. was added n-butyllithium (71.89 mL of a 2.5 M solution in hexanes, mmol, 2.5 equiv), and the mixture was allowed to warm to 0° C. for 30 min before recooling to –78° C. The lithium diisopropylamine thus generated was then added via cannula to the $ZnCl_2$ ester mixture dropwise at a steady rate over 40 min, and the resultant reaction mixture was allowed to slowly warm to rt and stir overnight. The yellow reaction mixture was then poured into a separatory funnel, diluted with 300 mL $Et_2O$, and the resultant organic solution was washed successively with 200 mL 1N HCl and 300 mL brine, dried ($Na_2SO_4$), and concentrated under reduced pressure. Purification by flash chromatography (silica gel, 3% MeOH in $CH_2Cl_2$ with 0.5% HOAc) gave 17.8 g (92%) of the desired amino acid product as a white solid. (FAB MH+270).

EXAMPLE 30

General Method C: Peptide coupling to 4,5-methanoprolinamide, amide dehydration and final deprotection.

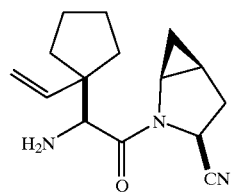

The TFA salt of amide 13 was coupled to a variety of racemic quaternary protected amino acids using HOBT/

EDC in DMF at rt to give a D/L mixture of diastereomers at the N-terminal amino acid. The desired L diastereomer was chromatographically isolated either as the amide 21 or as the nitrile 22. Nitrile 22 was obtained by treatment of the amide with POCl$_3$/imidazole in pyridine at −20° C. The final target 23 was obtained by deprotection under acidic conditions using TFA in CH$_2$Cl$_2$.

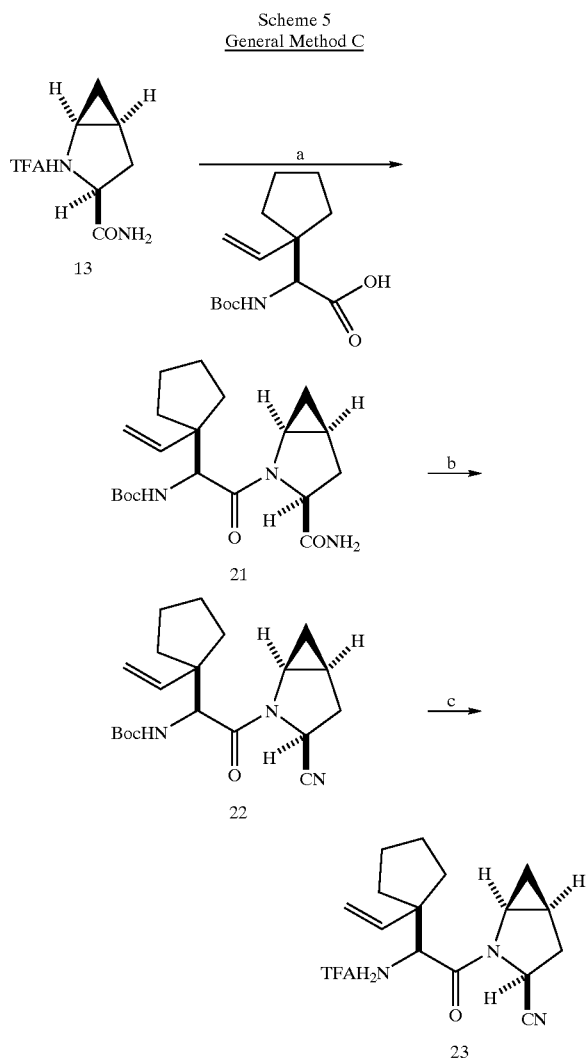

a. EDAC, HOBT, DMF b. POCl$_3$, pyridine, imidazole, -20 C c. TFA, CH$_2$Cl$_2$, RT Step 1

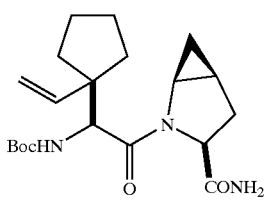

Example 6 Step 3 compound (877 mg, 3.65 mmol) and N-Boc cyclopentylvinylamino acid, described in Step 4 of general method B (1.13 g, 4.20 mmol) were dissolved in 20 mL anhydrous DMF, cooled to 0° C. and to this mixture was added EDAC (1.62 g, 8.4 mmol), HOBT hydrate (2.54 g, 12.6 mmol, and TEA (1.27 g, 12.6 mmol) and the reaction was allowed to warm to rt and stirred for 24 h. The reaction mixture was taken up in EtOAc (100 mL), washed with H$_2$O (3×20 mL), dried (Na$_2$SO$_4$), and purified by silica gel flash column chromatography (100% EtOAc) to give 1.38 g (86%) of Step 1 compound (MH+, 378).

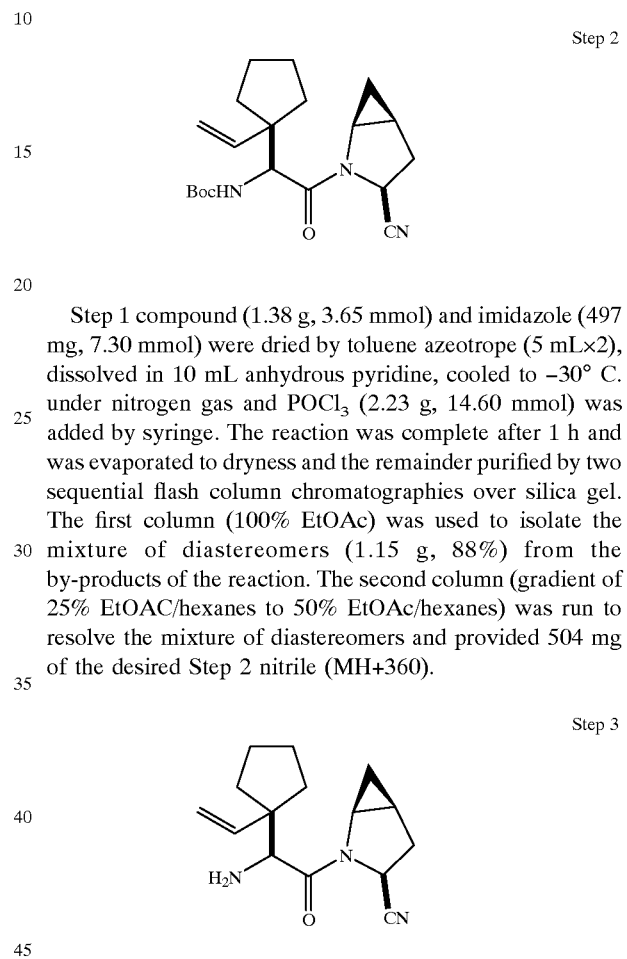

Step 1 compound (1.38 g, 3.65 mmol) and imidazole (497 mg, 7.30 mmol) were dried by toluene azeotrope (5 mL×2), dissolved in 10 mL anhydrous pyridine, cooled to −30° C. under nitrogen gas and POCl$_3$ (2.23 g, 14.60 mmol) was added by syringe. The reaction was complete after 1 h and was evaporated to dryness and the remainder purified by two sequential flash column chromatographies over silica gel. The first column (100% EtOAc) was used to isolate the mixture of diastereomers (1.15 g, 88%) from the by-products of the reaction. The second column (gradient of 25% EtOAC/hexanes to 50% EtOAc/hexanes) was run to resolve the mixture of diastereomers and provided 504 mg of the desired Step 2 nitrile (MH+360).

Step 2 compound (32 mg, 0.09 mmol) was dissolved in 1 mL of CH$_2$Cl$_2$ and 1 mL of TFA was added and the reaction stirred for 30 min at rt and was evaporated to dryness. The product was purified by reverse phase preparative column chromatography on a YMC S5 ODS 20×250 mm column to give 12 mg of the TFA salt (lyophilized from water or isolated after evaporation of eluent and trituration with ether) the title compound. Purification conditions: gradient elution from 10% methanol/water/0.1 TFA to 90% methanol/water/0.1 TFA over 18 min; 5 min. hold at 90% ter/0.1 trifluoroacetic acid. Flow rate: 20 Detection wavelength: 220.

Examples 30–39 were prepared by the methods outlined in General Method B and General Method C starting from cyclopentanone, cyclobutanone, cyclohexanone, cycloheptanone, cyclooctanone, cis-3,4-dimethylcylopentanone, and 4-pyranone, cyclopropaneethylhemiacetal, acetone, and 3-pentanone respectively.

TABLE 2

| Example | R | MS [M + H] |
|---|---|---|
| 30 | 1-vinylcyclopentyl | 260 |
| 31 | 1-vinylcyclobutyl | 246 |
| 32 | 1-vinylcyclohexyl | 274 |
| 33 | 1-vinylcycloheptyl | 288 |
| 34 | 1-vinylcyclooctyl | 302 |
| 35 | 3,4-dimethyl-1-vinylcyclopentyl | 288 |
| 36 | 4-vinyltetrahydropyran-4-yl | 276 |
| 37* | 1-vinylcyclopropyl | 232 |

TABLE 2-continued

| Example | R | MS [M + H] |
|---|---|---|
| 38 | 2-methyl-3-buten-2-yl (dimethylvinyl) | 234 |
| 39 | 3-ethyl-1-penten-3-yl | 262 |

*Step 3 compound was prepared by the method described in Tetrahedron Letters 1986, 1281–1284.

EXAMPLE 40

Step 1

Step 1 compound was prepared employing general method B starting from cyclopentanone and 2-fluoro-triethylphos-phonoacetate instead of triethylphosphonoacetate.

Step 2

Title compound was prepared by the peptide coupling of Step 1 acid followed by dehydration and final deprotection as described in general method C [MS (M+H) 278].

EXAMPLE 41

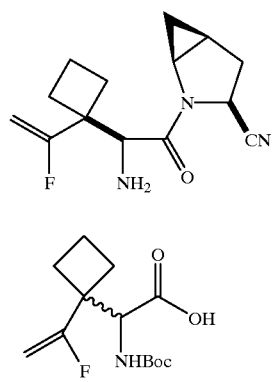

Step 1

Step 1 compound was prepared employing general method B starting from cyclobutanone and 2-fluoro-triethylphos-phonoacetate instead of triethylphosphonoacetate.

Step 2

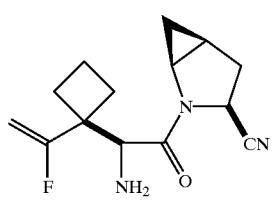

Title compound was prepared by the peptide coupling of Step 1 acid followed by dehydration and final deprotection as described in general method C. MS (M+H) 264.

EXAMPLE 42

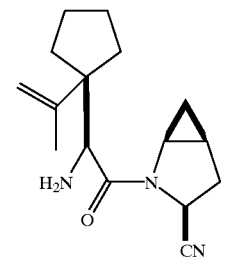

Step 1

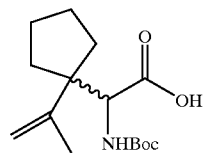

Step 1 compound was prepared employing general method B starting from cyclopentanone and triethylphosphono propionate instead of triethylphosphonoacetate.

Step 2

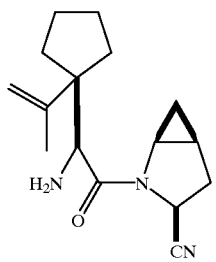

Title compound was prepared by the peptide coupling of Step 1 acid followed by dehydration and final deprotection as described in general method C. MS (M+H) 274

EXAMPLE 43

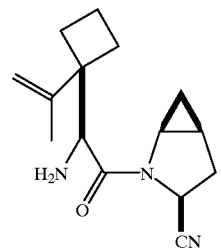

Step 1

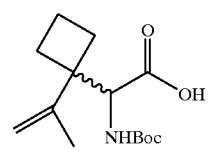

Step 1 compound was prepared employing general method B starting from cyclobutanone and triethylphosphono propionate instead of triethylphosphonoacetate.

Step 2

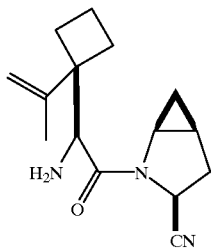

Title compound was prepared by the peptide coupling of Step 1 acid followed by dehydration and final deprotection as described in general method C. MS (M+H) 260.

EXAMPLE 44

General Method D: Oxidative cleavage of vinyl substituent by ozonolysis. The protected cyclopentylvinyl nitrile 22 was treated with ozone for 6–8 min and subjected to a reductive quench with sodium borohydride to furnish the hydroxymethyl analog 24 directly. This compound was deprotected under acidic conditions with TFA in $CH_2Cl_2$ at 0° C. to give the target compound 25.

Scheme 6
General Method D, Examples 44, 46, 48

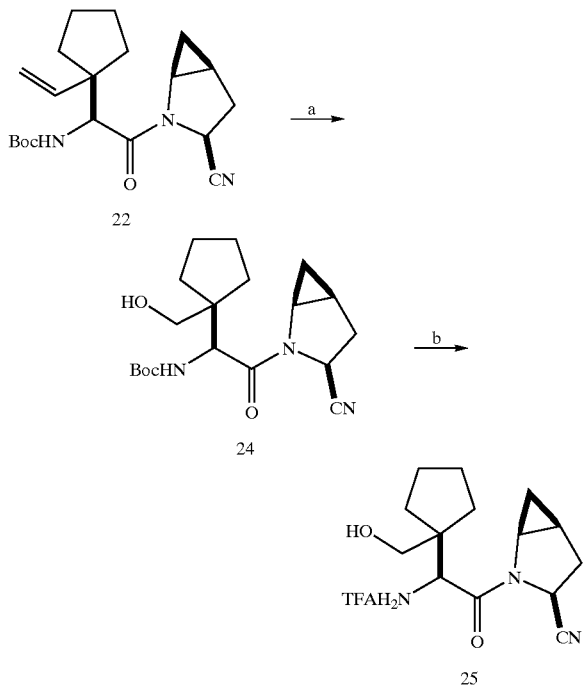

a. $O_3$, MeOH:$CH_2Cl_2$, 10:4, -78 C; then $NaBH_4$, -78 C to 0 C, 79%
b. TFA:$CH_2Cl_2$, 1:2, 0 degrees C.

Step 1

Cyclopentylvinyl compound prepared in Step 2 of general method C (1.28 g, 3.60 mmol) was dissolved in 56 mL of a 2:5 mixture of $CH_2Cl_2$:methanol, cooled to −78° C. and was treated with a stream of ozone until the reaction mixture took on a blue color, at which time, $NaBH_4$ (566 mg, 15.0 mmol, 4.2 equiv) was added and the reaction was warmed to 0° C. After 30 min, the reaction was quenched with 2 mL saturated aqueous $NaHCO_3$ and then warmed to rt. The reaction mixture was evaporated to dryness and taken up in EtOAc. A small amount of water was added to dissolve the inorganics and the layers separated. The EtOAc layer was dried ($Na_2SO_4$), filtered and evaporated to an oil that was purified by flash column chromatography on silica gel with EtOAc to give 922 mg (71%) of Step 1 compound. MS(M+H)364.

Step 2

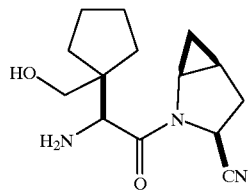

Step 1 compound (900 mg, 2.48 mmol) was dissolved in 60 mL of $CH_2Cl_2$, cooled to 0° C. and treated with 20 mL of freshly distilled TFA. The reaction was complete in 80 min and the mixture was evaporated to dryness and purified by preparative HPLC (YMC S5 ODS 30×100 mm, 18 minute gradient 80% Solv A:Solv B to 100% Solv B, Solvent A=10% MeOH-90%$H_2O$-0.1% TFA, Solvent B=90% MeOH-10% $H_2O$ -0.1% TFA, collected product from 5.1–6.5 min) to give, after lyophillization from water, 660 mg (71%) of title compound, TFA salt as a white lyophillate. (MH+264).

EXAMPLE 45

General Method E: Oxidative cleavage of vinyl substituent by osmium tetroxide-sodium periodate followed by sodium borohydride reduction to alcohol. The cyclobutylolefin 26 was treated with osmium tetroxide and sodium periodate in THF:water, 1:1, and the intermediate aldehyde was isolated crude and immediately reduced with sodium borohydride to give 27 in 56% yield. Standard deprotection conditions using TFA afforded the target compound 28.

Scheme 7
General Method E, Examples 45, 47

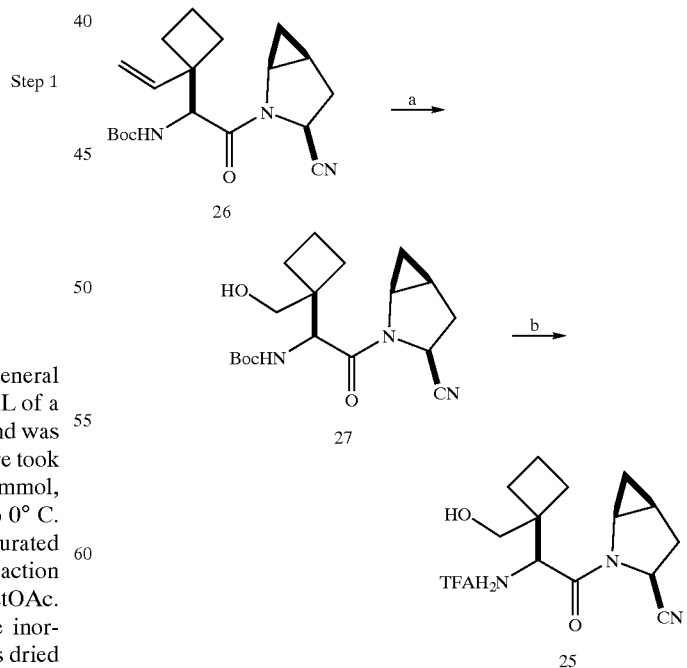

a. $OsO_4$, THF:$H_2O$; 1:1; $NaIO_4$; workup, then $NaBH_4$, MeOH, RT. 56%
b. TFA:$CH_2Cl_2$, 1:2, 0 degrees C to RT.

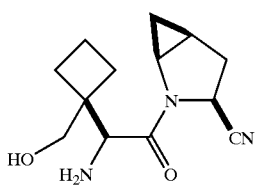

Step 1

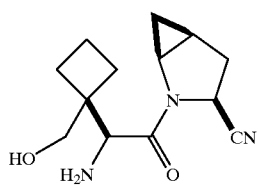

N-Boc protected cyclobutylvinyl compound (Example 31, prepared by general method C) (0.16 g, 0.46 mmol) was dissolved in 10 mL of a 1:1 mixture of THF:water and treated with OSO$_4$ (12 mg, catalyst) and NaIO$_4$ (0.59 g, 2.76 mmol, 6 equiv). After 2 h, the reaction mixture was diluted with 50 mL of ether and 10 mL of water. The layers were equilibrated and the organic fraction was washed one time with NaHCO$_3$ solution, dried over MgSO$_4$ and concentrated to give a dark oil. The oil was diluted with 10 mL of methanol and treated with NaBH$_4$ (0.08 g, 2.0 mmol). The mixture turned very dark and after 30 min was diluted with ether and the reaction was quenched with aqueous NaHCO$_3$ solution. The mixture was equilibrated and layers separated. The organic fraction was washed with solutions of NaHCO$_3$ and 0.1 M HCl. The organics were dried (MgSO$_4$) and concentrated to give 90 mg (56%) of the Step 1 compound as a dark oil.

Step 2

Step 1 compound (90 mg, 0.26 mmol) was dissolved in 3 mL of CH$_2$Cl$_2$, cooled to 0° C. and treated with 3 mL of freshly distilled TFA. The reaction was complete in 80 min and evaporated to dryness and purified by preparative HPLC (YMC S5 ODS 30×100 mm, 10 minute gradient 100%A to 100% Solvent A=10% MeOH-90%H20O-0.1% TFA, Solvent B=MeOH-10% H$_2$O-0.1% TFA, to give, after removal of water, 50 mg (60%) of title compound. (MH+250).

TABLE 3

| Example | R | Method of Preparation | [M + H] |
|---|---|---|---|
| 44 | cyclopentyl-CH$_2$OH | Ozonolysis/ borohydride | 264 |
| 45 | cyclobutyl-CH$_2$OH | Osmium/periodate/ borohydride | 250 |
| 46 | cyclohexyl-CH$_2$OH | Ozonolysis/ borohydride | 278 |
| 47 | cycloheptyl-CH$_2$OH | Osmium/periodate/ borohydride | 292 |
| 48 | dimethylcyclopentyl-CH$_2$OH | Ozonolysis/ borohydride | 292 |

EXAMPLE 49

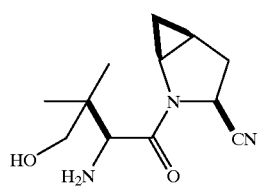

Step 1

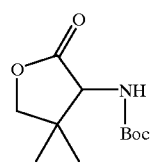

Part A. A 50-mL flask was charged with dihydro-4,4-dimethyl-2,3-furandione (5.0 g, 39.0 mmol), acetic acid (10 mL), sodium acetate (3.82 g, 39.0 mmol) and hydroxylamine hydrochloride (2.71 g, 39.0 mmol). The reaction mixture was stirred for 2 h at rt and concentrated under reduced pressure to remove most of the acetic acid. The remainder was poured into water (100 mL) and the aqueous phase extracted with EtOAc (3×40 mL). The organics were dried over $Na_2SO_4$ and concentrated to a colorless oil which solidified on standing.

Part B. A 200-mL round bottomed flask was charged with Part A solid (@ 39 mmol) and diluted with 80 mL of ethanol and 39 mL of 2N HCl (78 mmol). The mixture was treated with 1.0 g of 5% Pd/carbon and the mixture degassed. The flask was placed under an atmosphere of $H_2$ for 8 h. The mixture was filtered through celite and the filtrate concentrated to an off white solid.

Part C. A 250-mL round bottomed flask was charged with Part B solid and diluted with THF (50 mL) and water (15 mL). The mixture was treated with di-tert-butyldicarbonate (12.7 g, 117 mmol) and sodium bicarbonate (10.0 g, 117 mmol). After 4 h of stirring the mixture was diluted with 50 mL of ether and 50 mL of water. The layers were separated and the organic fraction dried over $MgSO_4$ and concentrated. The residue was purified by flash column chromatography on silica gel with 30% EtOAc in hexanes to give 2.00 g (22% overall) of Step 1 compound as a white solid.

Step 2

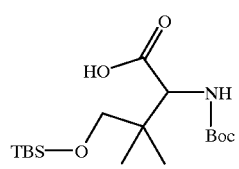

To a stirred solution of Step 1 compound (1.00 g, 3.80 mmol) in THF (20 mL) at rt under nitrogen was added LiOH hydrate (0.16 g, 3.80 mmol) and then water (5 mL). The reaction was stirred at 40° C. for 0.5 h and then cooled to rt. The mixture was concentrated to dryness and the remainder was stripped from THF (2×), toluene (2×) and THF (1×). The remaining glass was diluted with 5 mL of THF and treated with imidazole (0.63 g, 9.19 mmol) followed by t-butyl-dimethylsilyl chloride (1.26 g, 8.36 mmol). The reaction was stirred overnight and quenched with 10 mL of methanol. After 1 h of stirring the mixture was concentrated. An additional portion of methanol was added and the mixture concentrated. The oil was diluted with ether and 0.1 N HCl (pH 2). The layers were equilibrated and aqueous drawn off. The organic fraction was dried over $MgSO_4$ and concentrated to give 1.25 g (83%) of Step 2 compound as a colorless glass.

Step 3

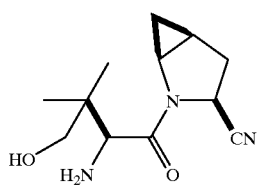

The Title compound was prepared by the peptide coupling of Step 2 carboxylic acid with Example 6 Step 3 amine, followed by dehydration and deprotection as outlined in General Method C. MS (M+H) 238.

General Method F: Catalytic Hydrogenation of vinyl substituent. As shown in Scheme 8, the protected vinyl substituted amino acid 20 was transformed to the corresponding saturated analog 29 by catalytic hydrogenation using 10% Pd/C and hydrogen at atmospheric pressure.

Scheme 8
General Method F, Examples 50–56

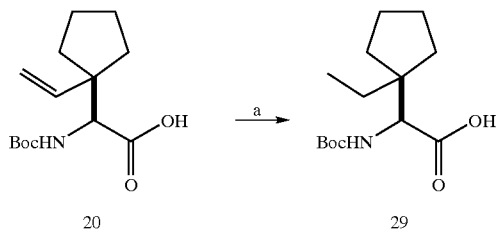

a. 10% Pd/C, 1atm $H_2$, MeOH, 12h, 100%

Step 1.

The N-(tert-Butyloxycarbonyl)(1'vinylcyclopentyl) glycine (2.23 g, 8.30 mmol) was dissolved in 50 mL MeOH and placed in a hydrogenation vessel purged with argon. To this mixture was added 10% Pd-C (224 mg, 10% w/w) and the reaction stirred under 1 atm $H_2$ at rt for 12 h. The reaction was filtered through celite and concentrated and purified by flash column chromatography on silica gel with 1:9 methanol:$CH_2Cl_2$ to give the Step 1 compound as a glass. (FAB MH+272)

Examples 50–56 were prepared by the peptide coupling of amino acids (where the vinyl substituent has been hydrogenated according to general method F) followed by dehydration and deprotection as described in general method C.

TABLE 4

| Example | R1, R2 | MS [M + H] |
|---------|--------|------------|
| 50 | Cyclopentyl | 262 |
| 51 | cyclobutyl | 248 |
| 52 | cycloheptyl | 290 |
| 53 | 4-pyranyl | 278 |
| 54 | methyl, methyl | 236 |
| 55 | ethyl, ethyl | 264 |
| 56 | methyl, ethyl | 250 |

EXAMPLE 57

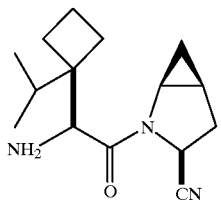

The title compound in Example 57 was prepared by the peptide coupling of the isopropyl cyclobutane amino acid (where the olefin substituent has been hydrogenated according to general method F) followed by dehydration and deprotection as described in general method C.

EXAMPLE 58

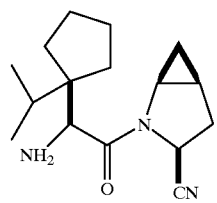

The title compound in Example 58 was prepared by the peptide coupling of the isopropyl cyclopentane amino acid (where the olefin substituent has been hydrogenated according to general method F) followed by dehydration and deprotection as described in general method C. MS (M+H) 276

General Method G: L-Amino acids synthesized by Asymmetric Strecker Reaction. Commercially available adamantyl carboxylic acid was esterified either in MeOH with HCl at reflux or using trimethylsilyldiazomethane in Et₂O/methanol to give 30. The ester was reduced to the alcohol 31 with LAH in THF and then subjected to a Swern oxidation to give aldehyde 32. Aldehyde 32 was transformed to 33 under asymmetric Strecker conditions with KCN, NaHSO₃ and R-(−)-2-phenylglycinol. The nitrile of 33 was hydrolyzed under strongly acidic conditions using 12M HCl in HOAc to give 34. The chiral auxiliary was removed by catalytic reduction using Pearlman's catalyst in acidic methanol under 50 psi hydrogen to give 35 and the resulting amino group was protected as the t-butylcarbamate to give 36.

Scheme 9
General Method G, Examples 59–64

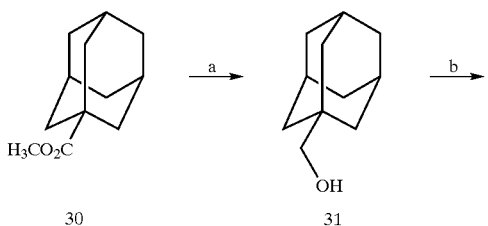

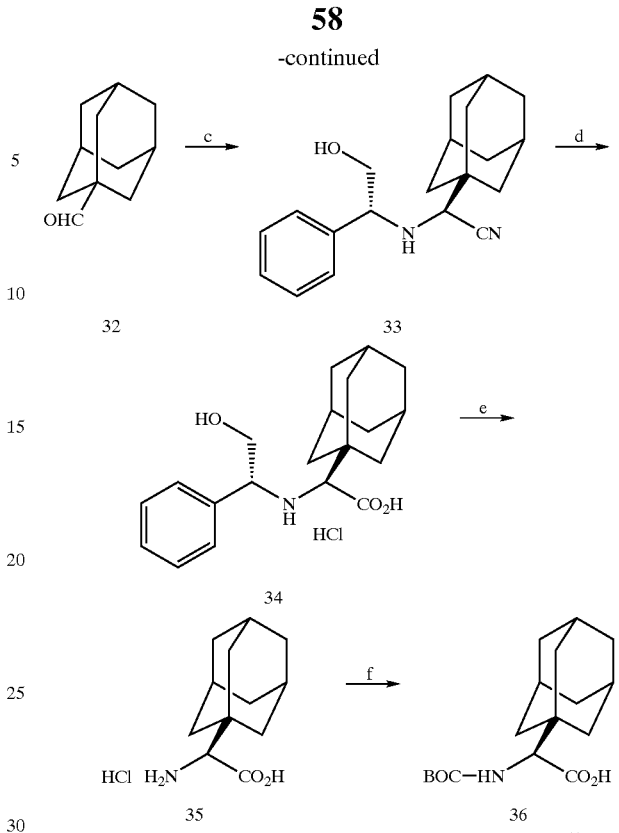

a. LAH, THF, 0 C TO RT, 96% b. ClCOCOCl, DMSO, CH₂Cl₂, -78 C, 98% c. R-(-)-2-Phenylglycinol, NaHSO₃, KCN d. 12M HCl, HOAc, 80 C, 16h, 78% e. 20% Pd(OH)₂, 50 psi H₂, MeOH:HOAc, 5:1 f. (Boc)₂O, K₂CO₃, DMF, 92%, 2 steps Step 1

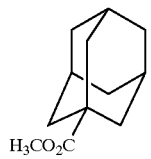

Adamantane-1-carboxylic acid (10.0 g, 55 mmol, 1 equiv) was dissolved in a mixture of Et₂O (160 mL) and MeOH (40 mL), and was treated with trimethylsilyl diazomethane (2.0 M in hexane, 30 mL, 60 mmol, 1.1 equiv) and stirred at rt for 3 h. The volatiles were then removed by rotary evaporation and the product purified by flash column chromatography on silica gel (5×15 cm) with 40% CH₂Cl₂/hexanes to give the product as a white crystalline solid (10.7 g, 100%).

Step 2

Step 1 compound (10.7 g, 0.055 mmol, 1 equiv) was dissolved in anhydrous THF (150 mL) under argon and was treated with a solution of LiAlH₄ (1 M in THF, 69 mL, 69 mmol, 1.25 equiv). After stirring at rt for 1.5 h, the reaction was cooled to 0° C. and quenched sequentially with H₂O (5.1 mL), 15% aq NaOH (5.1 mL), and H₂O (10.2 mL). After stirring at rt for 15 min, the slurry was vacuum filtered, and the solids washed with EtOAc (2×100 mL). The filtrate was concentrated by rotary evaporation and the resulting solid purified by flash column chromatography on silica gel (5×15 cm) with 10% EtOAc/CH$_2$Cl$_2$. This afforded the Step 2 product as a white solid (8.74 g, 96%).

Step 3

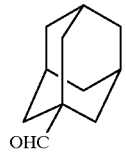

An oven-dried 3-neck flask equipped with 125-mL addition funnel was charged with anhydrous CH$_2$Cl$_2$ (150 mL) and anhydrous DMSO (10.3 mL, 0.145 mol, 2.5 equiv) under argon atmosphere and cooled to −78° C. Slow dropwise addition of oxalyl chloride (6.7 mL, 0.0768 mol, 1.32 equiv) followed by stirring for 15 min provided an activated DMSO adduct. This was treated with a solution of Step 2 compound (9.67 g, 58.2 mmol, 1 equiv) in dry CH$_2$Cl$_2$ (75 mL) and the reaction allowed to stir for 1 h. The resulting white mixture was then treated dropwise with triethylamine (40.5 mL, 0.291 mol, 5 equiv). After 30 min, the cooling bath was removed, and the reaction quenched sequentially with cold 20% aq KH$_2$PO$_4$ (25 mL) and cold H$_2$O (150 mL). After stirring at rt for 15 min the mixture was diluted with Et$_2$O (400 mL) and the layers were separated. The organics were washed organic with cold 10% aq KH$_2$PO$_4$ (3×150 mL) and satd aq NaCl (100 mL). The organics were dried (Na$_2$SO$_4$), filtered and concentrated. The residue was purified by flash column chromatography on silica gel (5×10 cm) with CH$_2$Cl$_2$ to give the Step 3 compound as a white solid (9.40 g, 98%).

Step 4

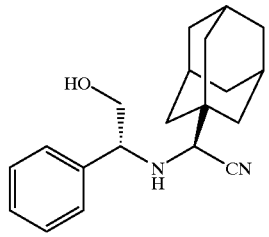

Step 3 compound (9.40 g, 57 mmol, 1 equiv) was suspended in H$_2$O (145 mL) and cooled to 0° C. The mixture was treated with NaHSO$_3$ (5.95 g, 57 mmol, 1 equiv), KCN (4.0 g, 59 mmol, 1.04 equiv), and a solution of (R)-(−)-phenylglycinol (8.01 g, 57 mmol, 1 equiv) in MeOH (55 mL). The resulting mixture was stirred at rt for 2 h, then refluxed for 16 h. The mixture was cooled to rt, and 200 mL of EtOAc added. After mixing for 15 min the layers were separated. The aqueous fraction was extracted with EtOAc. The combined EtOAc extracts were washed with brine (50 mL), dried over anhydrous Na$_2$SO$_4$, filtered and the filtrate concentrated. The product was purified by flash column chromatography on silica gel (6.4×20 cm) with 20% EtOAc/hexanes to give the desired (R,S) product as a white solid (11.6 g, 37.4 mmol, 65%): MS m/e 311 (M+H)$^+$.

Step 5

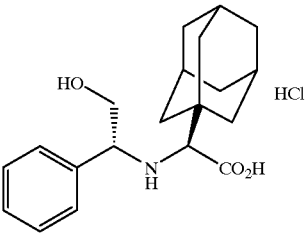

The Step 4 nitrile (5.65 g, 18 mmol) was heated in conc. HCl (120 mL) and HOAc (30 mL) at 80° C. for 18 h, at which time the reaction was cooled in an ice bath. Vacuum filtration of the resulting precipitate afforded the desired product as a white solid (5.21 g, 14 mmol, 78%). MS m/e 330 (m+H)$^+$.

Step 6

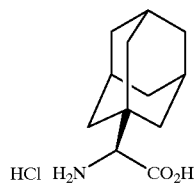

The Step 6 compound (5.21 g, 14 mmol) was dissolved in MeOH (50 mL) and HOAc (10 mL), and hydrogenated with H$_2$ (50 psi) and Pearlman's catalyst (20% Pd(OH)$_2$, 1.04 g, 20% w/w) for 18 h. The reaction was filtered through a PTFE membrane filter and the catalyst washed with MeOH (3×25 mL). The filtrate was concentrated by rotary evaporation to afford a white solid. The product was used in Step 7 without further purification.

Step 7

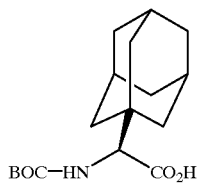

The crude Step 6 compound (@ 14 mmol) was dissolved in anhydrous DMF (50 mL) under argon and treated with K$_2$CO$_3$ (5.90 g, 42 mmol, 3 equiv) and di-tert-butyldicarbonate (3.14 g, 14 mmol, 1 equiv) under argon at rt. After 19 h, the DMF was removed by rotary evaporation (pump) and the residue dried further under reduced pressure. The residue was mixed with H$_2$O (100 mL) and Et$_2$O (100 mL), the layers separated, and the alkaline aqueous with Et$_2$O (2×100 mL) to remove the by-product from the hydrogenolysis step. The aqueous was cooled to 0° C., diluted with EtOAc (200 mL), and stirred vigorously while care fully acidifying the aqueous to pH 3 with 1N aq HCl. The layers separated and the aqueous extracted with EtOAc (100 mL). The combined EtOAc extracts were washed with brine (50 mL), dried (Na$_2$SO$_4$), filtered and the filtrate concentrated by rotary evaporation. The residue was purified by SiO$_2$ flash column (5×12 cm) with 5% MeOH/CH$_2$Cl$_2$+ 0.5% HOAc. The product was chased with hexanes to afford the product as a white foam (4.07 g, 13 mmol, 92%): MS m/e 310 (m+H)$^+$.

EXAMPLE 59

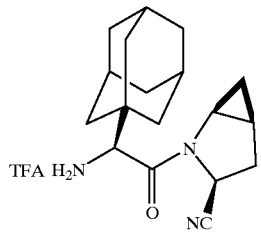

The title compound in Example 59 was prepared by the peptide coupling of the Step 7 compound in general method G followed by dehydration and deprotection as described in general method C. MS m/e 300 (m+H)$^+$.

EXAMPLE 60

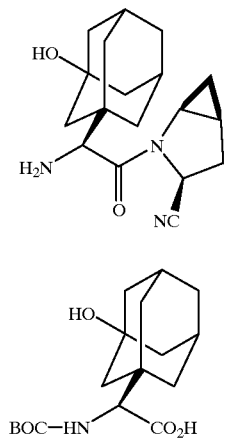

Step 1

A solution of KMnO$_4$ (337 mg, 2.13 mmol, 1.1 equiv) in 2% aq KOH (6 mL) was heated to 60° C. and Step 7 compound in general method G (600 mg, 1.94 mmol, 1 equiv) was added in portions, and heating increased to 90° C. After 1.5 h, the reaction was cooled to 0° C., EtOAc (50 mL) was added, and the mixture was carefully acidified to pH 3 with 1N HCl. The layers were separated and the aqueous was extracted with EtOAc (50 mL). The combined organic extracts were washed with brine, dried over Na$_2$SO$_4$, filtered and concentrated. The residue was purified by flash column chromatography on silica gel (3.8×15 cm) with 2% (200 mL), 3% (200 mL), 4% (200 mL), and 5% (500 mL) MeOH/CH$_2$Cl$_2$+0.5% HOAc. After isolation of the product, the material was chased with hexanes to afford a white solid (324 mg, 51%): MS m/e 326 (m+H)$^+$.

Step 2

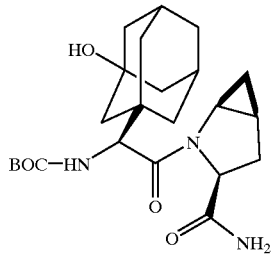

The Step 1 compound (404 mg, 1.24 mmol, 1 equiv) was dissolved in anhydrous DMF (10 mL) under argon and cooled to 0° C. The following were added in order: Example 6 Step 3 salt (328 mg, 1.37 mmol, 1.1 equiv), HOBT (520 mg, 3.85 mmol, 3.1 equiv), EDAC (510 mg, 2.61 mmol, 2.1 equiv), and TEA (0.54 mL, 3.85 mmol, 3.1 equiv). The reaction mixture was allowed to warm to rt overnight and the DMF removed by rotary evaporation (pump). The remainder was dried further under vacuum. The residue was dissolved in EtOAc (100 mL), washed with satd aq NaHCO$_3$ (50 mL) and satd aq NaCl (25 mL), dried over anhydrous Na$_2$SO$_4$, filtered and concentrated by rotary evaporation. The product was purified flash column chromatography on silica gel (3.8×15 cm) with a gradient of 6% (200 mL), 7% (200 mL), and 8% (500 mL) MeOH/CH$_2$Cl$_2$ to give the product as a white solid (460 mg, 1.06 mmol, 85%): MS m/e 434 (m+H)$^+$.

Step 3

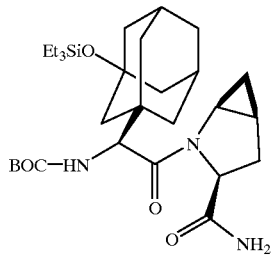

The Step 2 compound (95 mg, 0.22 mmol, 1 equiv) was dissolved in anhydrous CH$_2$Cl$_2$ (2.5 mL) under argon and cooled to −78° C. The mixture was treated with diisopropylethylamine (65 μL, 0.37 mmol, 1.7 equiv), and triethylsilyl triflate (75 μL, 0.33 mmol, 1.5 equiv), and stirred at 0° C. for 1.5 h. The reaction was mixed with MeOH (0.5 mL), silica gel (200 mg) and H$_2$O (2 drops) and stirred at rt for 18 h. The solvent was removed by rotary evaporation and the residue purified flash column chromatography on silica gel (2.5×10 cm) with 4% MeOH/CH$_2$Cl$_2$ to afford the product (92 mg, 0.17 mmol, 77%): Ms m/e 549 (m+H)$^+$.

Step 4

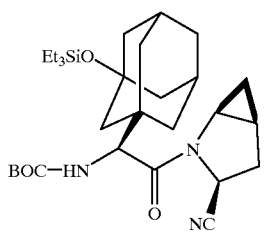

The Step 3 compound (90 mg, 0.16 mmol, 1 equiv) was dissolved in anhydrous pyridine (2 mL) under argon and cooled to −30° C. Treatment with imidazole (24 mg, 0.35 mmol, 2.1 equiv) and phosphorous oxychloride (66 μL, 0.67 mmol, 4.1 equiv), and continued stirring at −30° C. for 45 min gave a thick slurry. Volatiles were by rotary evaporation and the cake dried further under reduced pressure. The product was purified by flash column chromatography on silica gel (2.5×10 cm) with 7% EtOAc/CH$_2$Cl$_2$ to afford the product as a white foam (76 mg, 87%): MS m/e 530 (m+H)$^+$ Step 5

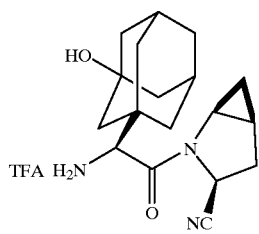

The Step 4 compound (76 mg, 0.14 mmol) was dissolved in anhydrous CH$_2$Cl$_2$ (1 mL) and cooled to 0° C. and treated with TFA (1 mL) and H$_2$O (2 drops) and stirred for 1.5 hr at 0° C. The solvents were removed by rotary evaporation and the residue was chased with toluene (5 mL) and dried under reduced pressure. Trituration with Et$_2$O afforded the title compound as a white solid (54 mg, 88%): MS m/e 316 (m+H)$^+$.

EXAMPLE 61

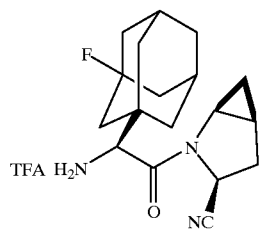

Step 1

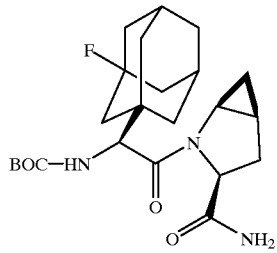

An oven-dried flask purged with argon was charged with anhydrous CH$_2$Cl$_2$ (3 mL) and cooled to −78° C. Treatment with diethylaminosulfur trifluoride (DAST, 60 μL, 0.45 mmol, 1.5 equiv), followed by a solution of the Example 60 Step 2 compound (131 mg, 0.30 mmol, 1 equiv) in dry CH$_2$Cl$_2$ (3 mL). After 15 min, the reaction was poured into a separatory funnel containing satd aq NaHCO$_3$ (25 mL) and the layers were separated. The aqueous fraction was extracted with CH$_2$Cl$_2$ (25 mL), then the combined organic extracts were washed with brine (10 mL), dried (Na$_2$SO$_4$), filtered and concentrated. The product was purified by flash column chromatography on silica gel (2.5×10 cm) with 5% MeOH/CH$_2$Cl$_2$ to give Step 1 compound (124 mg, 0.29 mmol, 94%): MS m/e 436 (m+H)$^+$.

Step 2

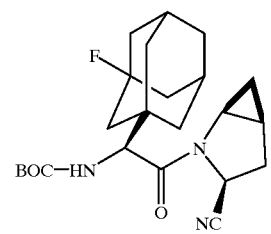

The fluorinated amide from Step 1 (161 mg, 0.37 mmol, 1 equiv) was dissolved in anhydrous pyridine (4 mL) under argon and cooled to −30° C. The mixture was treated with imidazole (54 mg, 0.77 mmol, 2.1 equiv) and phosphorous oxychloride (143 μL, 1.52 mmol, 4.1 equiv) and stirred at −30° C. for 40 min. The solvent was removed by rotary evaporation and dried further under reduced pressure. The product was purified by flash column chromatography on silica gel (2.5×10 cm) with 5% EtOAc/CH$_2$Cl$_2$ to give the Step 2 compound as a white foam (126 mg, 82%): MS m/e 418 (m+H)$^+$.

Step 3

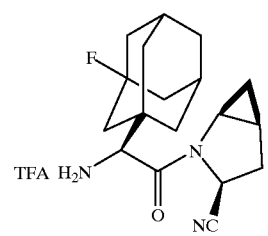

The Step 2 compound (125 mg, 0.30 mmol) was dissolved in TFA/CH$_2$Cl$_2$ (1:1 v/v, 2 mL), and stirred at rt. After 30 min, the solvents were removed by rotary evaporation, the remainder was chased with toluene (2×5 mL), and the solid dried under reduced pressure. Trituration with Et₂O afforded the title compound as a white solid (93 mg, 0.21 mmol, 72%): MS m/e 318 (m+H)⁺.

EXAMPLE 62

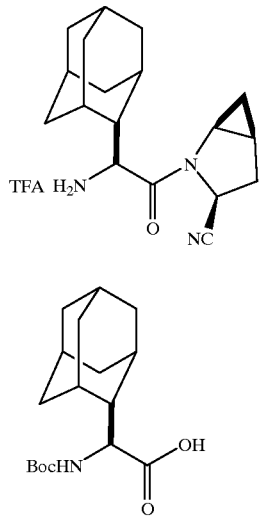

Step 1

The Step 1 compound was prepared beginning with 2-adamantanal and elaborated to the homochiral Boc-amino acid by an asymmetric Strecker synthesis according to general method G.

Step 2

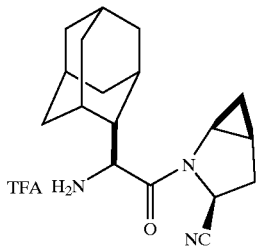

The title compound in Example 62 was prepared by the peptide coupling of the 2-adamantyl amino acid described in Step 1 followed by dehydration and deprotection as described in general method C.MS (M+H) 300.

EXAMPLE 63

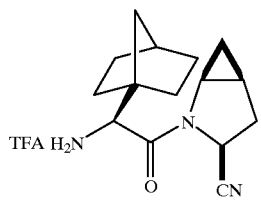

Step 1

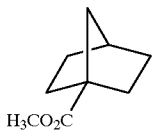

An oven-dried flask equipped with a condenser and drying tube was charged with norbornane-2-carboxylic acid (4.92 g, 35 mmol, 1 equiv) and treated with bromine (2.1 mL, 41 mmol, 1.15 equiv) and phosphorous trichloride (0.153 mL, 1.8 mmol, 0.05 equiv). The mixture was heated at 85° C. for 7 h protected from light. Additional bromine (0.4 mL, 7.8 mmol, 0.22 equiv) was added with continued heating for 1 h. The mixture was cooled to rt, and Et₂O (100 mL) was added. The mixture was washed with 10% aq NaHSO₃ (50 mL), H₂O (2×50 mL), and brine (25 mL). The ether fraction was dried (Na₂SO₄), filtered and concentrated by rotary evaporation. The product was purified by flash column chromatography on silica gel (5×15 cm) with 2% to 4% MeOH/CH2Cl₂+0.5% HOAc. The product was chased with hexanes to remove residual HOAc. The isolated material consists of two inseparable materials (4.7 g), which was used without further purification in the next step.

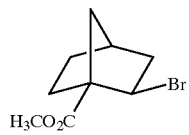

The crude product from above, exo-2-bromonorbornane-1-carboxylic acid (4.7 g, impure) in Et₂O (80 mL) and MeOH (20 mL), was mixed with trimethylsilyldiazomethane (2.0 M in hexane, 11.8 mL, 23.6 mol), and stirred at rt for 1 h. Solvent was removed by rotary evaporation, and purification of the oil by flash column chromatography on silica gel (5×18 cm) with a gradient of CH₂Cl₂/hexanes (600 mL each of 20% and 30%) followed by CH₂Cl₂ afforded the product as a white solid (3.97 g, 0.017 mol, 79% for 2 steps): MS m/e 233/235 (m+H)⁺.

Methyl exo-2-bromonorbornane-1-carboxylate (2.0 g, 8.58 mmol, 1 equiv) was dissolved in anhydrous THF (50 mL) in an oven-dried 3-neck flask equipped with a condenser, and purged with argon. The mixture was treated with AIBN (288 mg, 1.71 mmol, 0.2 equiv) and tributyltin hydride (3.6 mL, 12.87 mmol, 1.5 equiv), and then heated to reflux for 2 h. The flask was cooled to rt, and the THF was removed by rotary evaporation to give the crude product. The product was purified by flash column chromatography on silica gel(5×10 cm) with 5% EtOAc/hexanes. The resulting material was used in the next step without further purification.

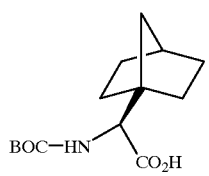

The Step 1 compound was prepared beginning with 1-norbonyl methyl carboxylate and elaborated to the homochiral Boc amino acid by an asymmetric Strecker synthesis according to general method G.

Step 3

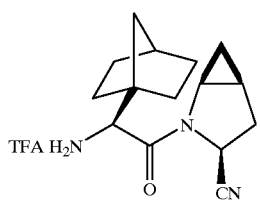

The title compound in Example 63 was prepared by the peptide coupling of the 1-norbonyl amino acid described in Step 2, followed by dehydration and deprotection as described in general method C. MS (M+H) 260.

EXAMPLE 64

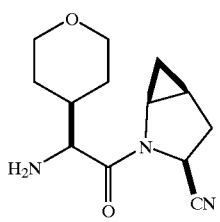

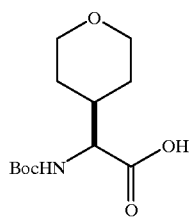

The Step 1 compound was prepared beginning with 4-formylpyran and elaborated to the homochiral Boc amino acid by an asymmetric Strecker synthesis according to general method G.

Step 2

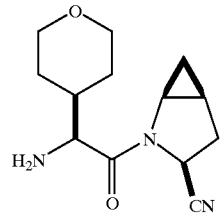

The title compound in Example 64 was prepared by the peptide coupling of the 4-pyranyl amino acid described in Step 2, followed by dehydration and deprotection as described in general method C. MS (M+H) 250.

General Method H: Strecker Synthesis of Racemic Amino Acids.

Scheme 10
General Method H, Examples 65–66

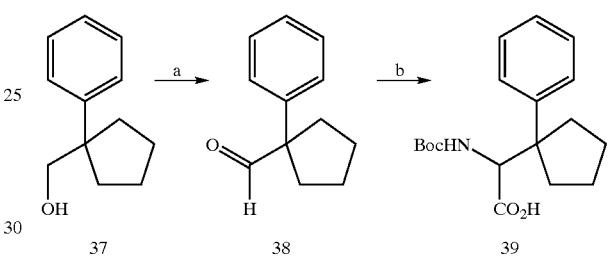

a. celite, PCC, CH$_2$Cl$_2$, RT, 91% b. NH$_4$Cl, NaCN, MeOH; 12M HCl, HOAc; (Boc)$_2$O, TEA, DMF.

Step 1

To a stirred solution of 1-phenylcyclo-1-pentane-carboxylic acid (5.00 g, 26.3 mmol) in 25 mL of THF at 0° C. was added LAH (52 mL, 52 mmol, 1M) in THF. The reaction mixture was slowly warmed to rt and then refluxed for 18 h. The reaction was quenched according to the Fieser procedure: careful addition of 2 mL of water; 6 mL of 15% NaOH in water; and 2 mL of water. The biphasic mixture was diluted with 100 mL of ether and the granular white solid filtered off. The ether fraction was dried over Na$_2$SO$_4$ and evaporated to give 4.30 g (93%) of the Step 1 compound.

Step 2

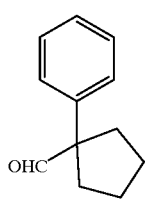

To a stirred solution of Step 1 compound (0.80 g, 4.50 mmol) in 15 mL of CH$_2$Cl$_2$ at rt was added celite (5 g)

followed by PCC (1.95 g, 5.00 mmol). After stirring for 3 h the reaction mixture was diluted with 40 mL of $CH_2Cl_2$ and filtered through celite. The filtrate was filtered an additional time through silica gel resulting in a colorless filtrate. The $CH_2Cl_2$ fraction was evaporated to give 0.72 g (91%) of the aldehyde as a colorless oil.

Step 3

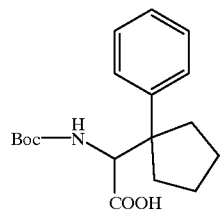

To a 50-mL round-bottomed flask containing Step 2 compound (0.72 g, 4.20 mmol) in 9 mL of water at rt was added NaCN (0.20 g, 4.20 mmol) followed by $NH_4Cl$ (0.20 g, 5.00 mmol). To this reaction mixture was then added methanol (8 mL) and the mixture was allowed to stir overnight. The reaction mixture was then extracted with ether (2×15 mL), dried ($MgSO_4$) and concentrated under reduced pressure to give the crude Strecker product.

To a 100-mL round-bottomed flask containing the crude Strecker product was added 10 mL of HOAc and 10 mL of conc. Hbl. The mixture was refluxed overnight. The mixture was concentrated under reduced pressure to give a yellow solid. The solid was triturated with 5 mL of 1:1 mixture of ether and hexanes. The white solid was treated with triethylamine (1.4 mL, 9.99 mmol) and di-tert-butyldicarbonate (1.00 g, 4.60 mmol) in 50 mL DMF. After 4 h the pH of the mixture was adjusted to 9 with saturated $Na_2CO_3$ soln. After an additional 3 h of stirring the mixture was extracted with 1:1 ether and hexanes and the aqueous fraction acidified to pH 2 with 5% $KHSO_4$ solution. The aqueous phase was washed with ether (2×40 mL), the organics dried ($MgSO_4$), and evaporated to an oil that was purified by silica gel flash chromatography with 8:92 methanol:$CH_2Cl_2$ to give 0.3 g (23%) of the Boc-protected amino acid as a light oil (M-H, 318).

EXAMPLE 65

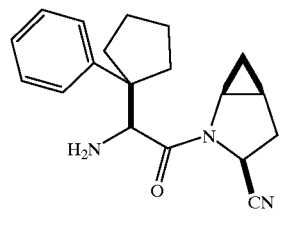

Step 1

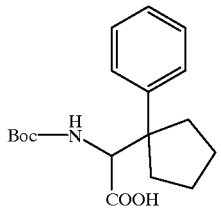

The synthesis of the Step 1 compound was described in general method H for the Strecker synthesis of racemic amino acids.

Step 2

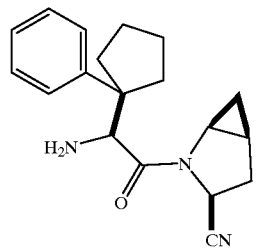

The title compound in Example 65 was prepared by the peptide coupling of the cyclopentylphenyl amino acid described in Step 1 and general method H followed by dehydration and deprotection as described in general method C. MS (M+H) 310.

EXAMPLE 66

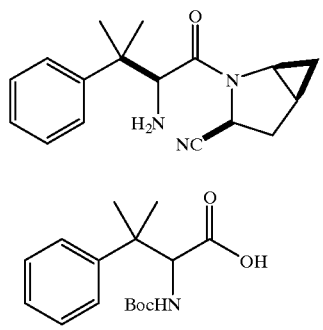

Step 1

Step 1 compound was prepared using racemic Strecker synthesis according to general method H starting from 2,2-dimethyl-phenylacetic acid.

Step 2

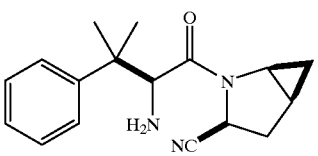

The title compound in Example 66 was prepared by the peptide coupling of the dimethylphenyl amino acid described in step 1 followed by dehydration and deprotection as described in general method C. MS (M+H) 284.

EXAMPLE 67

Step 1

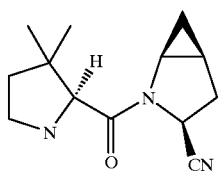

N-(Benzyloxycarbonyl)succinimide (5.6 g, 22.4 mmol) was dissolved in $CH_2Cl_2$ (25 mL) and the solution was added to a cooled (0° C.) and stirred solution of diethyl aminomalonate hydrochloride (5.0 g, 23.6 mmol) and triethylamine (13.4 mL, 95 mmol) in $CH_2Cl_2$ (125 ml). The resulting solution was stirred at 0° C. for 10 min and then at rt for 1 h. The solution was washed with 10% citric acid (2×50 mL), 10% sodium hydrogen carbonate (2×50 mL), and water (50 mL) and was then dried ($Na_2SO_4$) and evaporated to afford diethyl N-benzyloxycarbonylaminomalonate as a colorless oil, which crystallized upon standing at 0° C. (6.3 g) (LC/Mass + ion): 310 (M+H).

Step 2

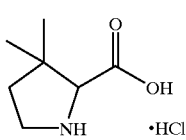

Step 1 compound (6.18 g, 20 mmol) was dissolved in dry ethanol (30 mL) and added to a solution of sodium ethoxide (2.85 g, 8.8 m mol; 21% w/w solution in ethanol (6 mL). A solution of 3-methyl-2-butenal (1.68 g, 20 mmol) in ethanol (12 mL) was added, and the solution stirred at 25° C. for 24 h. Acetic acid (0.56 mL) was then added the solution hydrogenated at 50 psi for 24 h using 10% Pd/C (2.0 g) as catalyst. The solution was filtered, evaporated and the residue chromatographed on silica with $CH_2Cl_2$/EtOAc (9:1) to give 2,2-dicarboethoxy-3,3-dimethyl-pyrrolidine (1.6 g) (LC/Mass, +ion): 244 (M+H).

This diester (850 mg) was refluxed in 5 M hydrochloric acid (10 mL)/TFA (1 mL) for 8 h to give, after evaporation, a powdery white solid. Crystallization from methanol/ether gave 3,3-dimethyl-dl-proline hydrochloride (190 mg) as white crystals mp 110–112° C.

Step 3

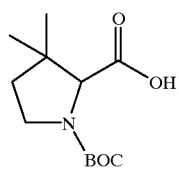

Step 2 compound (173 mg, 0.97 mmol) was dissolved in DMF (3 mL)/water (3 mL). To this clear solution was added triethylamine (0.46 mL, 3.18 mmol) and di-t-butyl dicarbonate (0.23 g, 1.06 mmol), and the reaction mixture was stirred at rt for 5 h. The solution was evaporated and the residue chromatographed on silica column using $CH_2Cl_2$/methanol (9:1) as eluent to yield t-butyloxy-carbonyl-3,3-dimethyl-dl-proline (200 mg) as an oil (LC/Mass, + ion): 244 (M+H).

Step 4

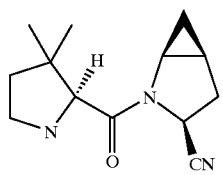

The title compound in Example 67 was prepared by the peptide coupling of the t-butyloxycarbonyl-3,3-dimethyl-dl-proline amino acid described in Step 3 followed by dehydration and deprotection as described in general method C. MS (M+H) 220.

EXAMPLE 68

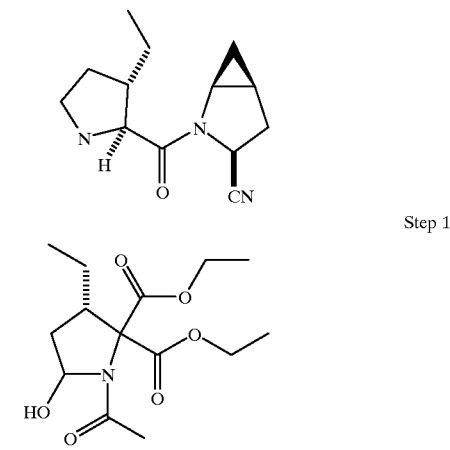

Step 1

Sodium ethoxide (940 mg of 21 wt % solution in ethanol, 2.9 mmol) in ethanol (2 mL) was added to a stirred solution of diethyl acetamidomalonate (4.31 g, 19,8 mmol) in EtOH (23 mL) at rt under argon. The reaction mixture was cooled to 0° C.; and trans-2-pentenal (1.51 g, 18.0 mmol) was added dropwise maintaining the reaction temperature at <50° C. After the addition, the reaction was allowed to warm to rt, stirred for 4 h, then quenched with acetic acid (460 µl). The solution was concentrated in vacuo, and the residue dissolved in EtOAc (25 mL), washed with 10% $NaHCO_3$ solution (2×5 mL), brine and dried ($MgSO_4$). The solution was filtered and concentrated to a 10 mL volume, then heated to reflux and diluted with hexane (20 mL). Upon cooling to rt, the title compound precipitated and was collected to give 3.0 g (50%) of the Step 1 compound (mp 106–109° C.; LC/Mass: + ions, 324 M+Na).

Step 2

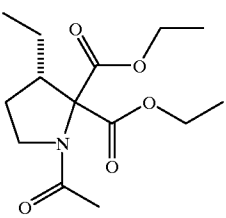

To a solution of Step 1 compound (2.87 g, 9.5 mmol) and triethylsilane (2.2(mL, 14.3 mmol) in $CH_2Cl_2$ (30 mL2 under argon was added TFA (7.35 mL, 95.3 mmol) dropwise with stirring while maintaining the internal temperature at 25° C. by means of an ice bath. After stirring for 4 h at rt, the solution was concentrated. The residue was diluted with CH₂Cl₂ (100 mL), then treated with H₂O (50 mL) and solid Na₂CO₃ with vigorous stirring until the mixture was basic. The organic layer was separated, dried (Na₂SO₄), filtered, then concentrated to give the Step 2 compound as a yellow oil which was used without further purification (LC/Mass: + ions, 308 M+Na).

Step 3

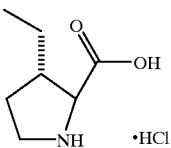

Step 2 compound (3.73 g, 9.5 mmol) was suspended in 6 N HCl (20 mL) and HOAc (5 mL) and heated at reflux for 20 h. The reaction mixture was then cooled, washed with EtOAc (20 mL), the n concentrated to give an oil which crystallized upon trituration with et her to give the title compound (1.2 g, 70.6%) (LC/Mass, + ion): 144 (M+H).

Step 4

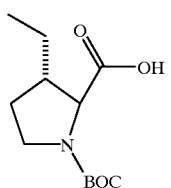

Step 3 compound (692 mg, 3.76 mmol) was dissolved in acetone (12 mL)/ water (12 mL). To this clear solution was added triethylamine (1.9 mL, 12.8 mmol) and di-t-butyl dicarbonate (928 mg, 4.24 mmol). The reaction mixture was stirred at rt for 18 h. The solvents were evaporated and the residue chromatographed on silica with 1:9 methanol:CH₂Cl₂ to give the Step 4 compound as an oil (LC/Mass: + ions, 266 M+Na).

Step 5

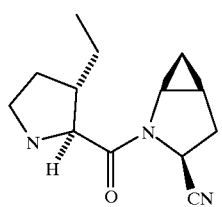

Example 68 compound was prepared by peptide coupling of Step 4 amino acid followed by dehydration and deprotection as described in general method C (MS (M+H) 234).

EXAMPLE 69

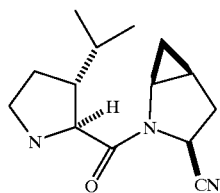

Step 1

Sodium ethoxide (940 mg, 2.9 mmol; 21% w/w solution in ethanol) in ethanol (2 mL) was added to a stirred solution of diethyl acetamidomalonate (4.31 g, 19.8 mmol) in EtOH (23 mL) at rt under argon. The reaction mixture was cooled to 0° C.; and 4-methyl-2-pentenal (1.77 g, 18.0 mmol)was added dropwise maintaining the reaction temperature at <50° C. After the addition, the reaction was allowed to warm to rt, stirred for 4 h, then quenched with acetic acid (460 μl). The solution was concentrated and the remainder dissolved in EtOAc (25 mL). The organics were washed with 10% NaHCO₃ solution (2×5 mL), brine and dried (MgSO₄). The solution was filtered and concentrated to 10 mL volume, then heated to reflux and treated with hexane (20 mL). On cooling, the Step 1 compound precipitated and was collected (3.3 g) (LC/Mass, + ion): 338 (M+Na).

Step 2

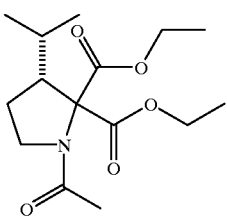

To a solution of Step 1 compound (3.0g, 9.5 mmol) and triethylsilane (2.28 mL, 14.3 mmol) in CH₂Cl₂ (30 mL) under argon was added TFA (7.35 mL, 95.3 mmol) dropwise with stirring while maintaining the internal temperature at 25° C., by means of an ice bath. After stirring for 4 h at rt, the solution was concentrated, the residue diluted with CH₂Cl₂ (100 mL), then treated with H₂O (50 mL) and solid Na₂CO₃ with vigorous stirring until the mixture was basic. The organic layer was separated, dried (Na₂SO₄), filtered, then concentrated to give the title compound as an oil which was used without further purification (LC/Mass:+ ions, 300 M+H).

Step 3

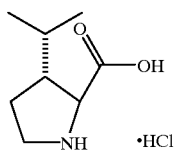

Step 2 compound (3.8 g, 9.5 mmol) was suspended in 6 N HCl (20 mL) and HOAc (5 mL) and heated at reflux for 20 h. The reaction mixture was cooled, washed with EtOAc (20 mL), then concentrated to give an oil which crystallized upon trituration with ether to give the step 3 compound (1.4 g, 76.0%). LC/Mass: + ions, 158 (M+H).

Step 4

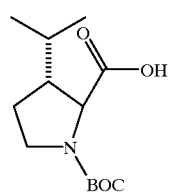

Step 3 compound (728 mg, 3.76 mmol) was dissolved in a 1:1 acetone/water solution (24 mL). To this clear solution was added triethylamine (1.9 mL, 12.8 mmol) and di-t-butyl dicarbonate (928 mg, 4.24 mmol). The reaction mixture was stirred at rt for 18 h. The solution was evaporated and the residue chromatographed on silica column using $CH_2Cl_2$/methanol (9:1) as eluent to give the title compound as an oil (LC/Mass, + ion): 258 (M+H).

Step 5

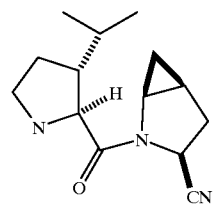

Example 69 compound was prepared by peptide coupling of Step 4 amino acid followed by dehydration and deprotection as described in general method C (MS (M+H) 248).

EXAMPLE 70

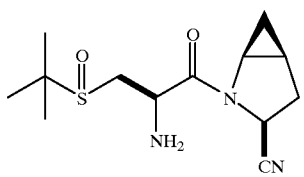

Step 1

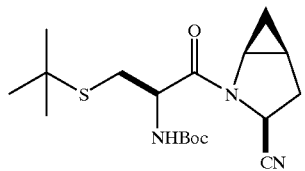

Step 1 compound was prepared by the procedure described in General Method C starting from N-Boc-S-t-butylcysteine.

Step 2

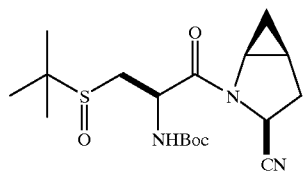

A 25-mL round-bottomed flask equipped with a magnetic stirring bar and $N_2$ inlet was charged with Step 1 compound (78 mg, 0.21 mmol) and chloroform (3 mL). The mixture was cooled to 0° C. and treated with m-chloroperoxybenzoic acid (85 mg, 0.44 mmol) in $CHCl_3$ (2 mL). After 3 h the solution was diluted with $CHCl_3$ (7 mL), washed with 5% $NaHCO_3$ (2×5 mL), $H_2O$ and dried over $Na_2SO_4$. Removal of solvent gave crude sulfoxide (100 mg), which was used without further purification (LC/Mass, + ions): 384 (M+H).

Step 3

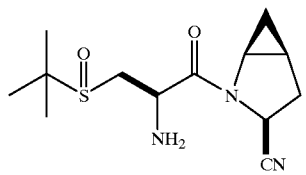

Trifluoroacetic acid (1.5 mL) was added to a cooled (0° C.) solution of Step 2 compound (100 mg, 0.26 mmol) in 5 mL $CH_2Cl_2$. The solution was then stirred at 0° C. for 1.5 h, diluted with $CH_2Cl_2$ (5 mL) and concentrated under reduced pressure to a thick oil. The product was purified by reverse phase preparative column chromatography on a YMC S5 ODS 20×100 mm column to give the title compound of Example 70, 17 mg, 16%. Purification conditions: gradient elution from 10% methanol/water/0.1 TFA to 90% methanol/water/0.1 TFA over 15 min 5 min hold at 90% methanol/water/0.1 TFA. Flow rate: 20 mL/min. Detection wavelength: 220. Retention Time 10 Min (LC/Mass, + ion): 284 (M+H).

EXAMPLE 71

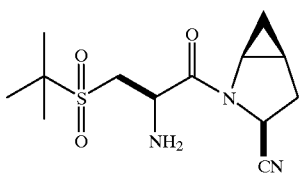

Step 1

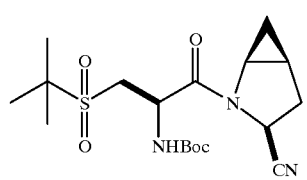

A 25-mL round-bottomed flask equipped with a magnetic stirring bar and N₂ inlet was charged with compound from Example 70, Step 1 (78 mg, 0.21 mmol) in chloroform (3 mL). The mixture was cooled to 0° C. and treated with m-chloroperoxybenzoic acid (144 mg, 0.84 mmol) in CHCl₃ (2 mL). After 30 min at rt, the solution was diluted with CHCl₃ (7 mL), washed with 5% NaHCO₃ (2×10 mL), H₂O and dried over Na₂SO₄. Removal of solvent gave the crude sulfone (100 mg), which was used without further purification (LC/Mass, + ion): 344 (M+H−Bu).

Step 2

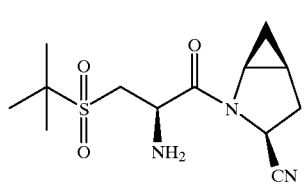

Trifluoroacetic acid (1.5 mL) was added to a cooled (0° C.) and stirred solution of Step 1 compound (100 mg, 0.26 mmol) in 5 mL CH₂Cl₂. The solution was stirred at 0° C. for 30 min, diluted with CH₂Cl₂ (5 mL) and concentrated under reduced pressure to a thick oil. The product was purified by reverse phase preparative column chromatography on a YMC S5 ODS 20×100 mm column to give the title compound, 14 mg, 17%. Purification conditions: gradient elution from 10% methanol/water/0.1 TFA to 90% methanol/water/0.1 TFA over 15 min. 5 min hold at 90% methanol/water/0.1 TFA. Flow rate: 20 mL/min. Detection wavelength: 220. Retention Time 10 Min. (LC/Mass, + ion): 300 (M+H).

EXAMPLE 72

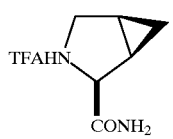

The title compound was prepared following a published procedure (Sasaki et al, Tetrahedron Lett. 1995, 36, 3149, Sasaki et al. Tetrahedron 1994, 50, 7093) used to synthesize (2S,3R,4S)-N-Boc-3,4-methano-L-proline carboxylate. The corresponding amide was prepared by general method A and deprotected with TFA to give the TFA salt also as described in general method A.

EXAMPLE 73

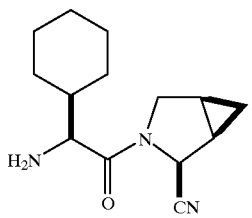

The title compound was prepared by coupling (2S,3R,4S)-3,4-methano-L-proline carboxamide-N-trifluoroacetate described in Example 72 with L-cyclohexylglycine and then dehydrated to the amide with POCl₃/imidazole and deprotected (N-terminal nitrogen) with TFA using general C (FAB MH+248).

EXAMPLE 74

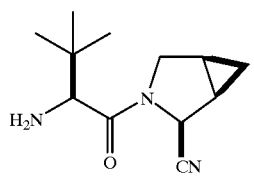

The title compound was prepared by coupling (2S,3R,4S)-3,4-methano-L-proline carboxamide-N-trifluoroacetate described in Example 72 with L-tert-butylglycine and then dehydrated to the amide with POCl₃/imidazole and deprotected (N-terminal nitrogen) with TFA using general C (FAB MH+222).

EXAMPLE 75

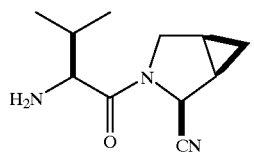

The title compound was prepared by coupling (2S,3R,4S)-3,4-methano-L-proline carboxamide-N-trifluoroacetate described in Example 72 with L-valine and then dehydrated to the amide with POCl₃/imidazole and deprotected (N-terminal nitrogen) with TFA using general C (FAB MH+207).

EXAMPLE 76

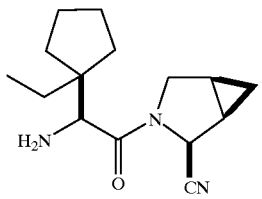

The title compound was prepared by coupling (2S,3R, 4S)-3,4-methano-L-proline carboxamide-N-trifluoroacetate described in Example 72 with N-(tert-butyloxycarbonyl)-(1'ethylcyclopentyl)glycine described in General Method B and then dehydrated to the amide with POCl$_3$/imidazole and deprotected (N-terminal nitrogen) with TFA using general C (FAB MH+262).

EXAMPLE 77

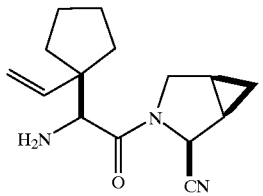

The title compound was prepared by coupling (2S,3R, 4S)-3,4-methano-L-proline carboxamide-N-trifluoroacetate described in Example 72 with N-(tert-butyloxycarbonyl)-(1'vinylcyclopentyl)glycine described in General Method B and then dehydrated to the amide with POCl$_3$/imidazole and deprotected (N-terminal nitrogen) with TFA using General Method C (FAB MH+260).

EXAMPLE 78

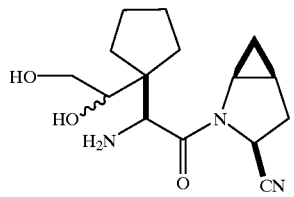

N-[((S)-cyclopentylvinyl)-N-tert-butoxycarbonylglycinyl]-(2S,4S,5S)-2-cyano-4,5-methano-L-prolylamide (70 mg, 0.19 mmol) described in General Method C, Step 2 was dissolved in a mixture of 2 mL t-BuOH/3 mL THF and N-methylmorpholine-N-oxide (33mg, 0.28 mmol) was added followed by osmium tetroxide (0.1 mmol, 50 mol %). The reaction was quenched with 1 mL of 100 aqueous Na$_2$SO$_3$ and was taken up in EtOAc and washed with H$_2$O 5 mL, dried (Na$_2$SO$_4$), filtered, evaporated and purified by silica gel flash chromatography (5% MeOH/CH$_2$Cl$_2$) to give 41 mg (55%) of the protected diol as an oil. The title compound was obtained by deprotection of the amine functionality with TFA according to General Method C (FAB MH+294).

EXAMPLE 79

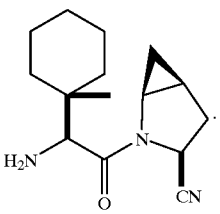

General Procedure I: Synthesis of Quaternary Amino Acids Via Michael Addition to Malonates followed by Selective Hydrolysis and Curtius Rearrangement. Examples 79–84.

Cyclohexanone and diethylmalonate underwent Knoevenagel condensation mediated by titanium tetrachloride in THF and CCl$_4$ to give 40. Copper (I) mediated Grignard addition of methylmagnesium bromide gave 41 which was selectively saponified to 42. Curtius rearrangement with trapping by benzyl alcohol gave 43 which was converted to 44 by a standard deprotection-protection protocol. Ester 44 was saponified to give the quaternary amino acid 45.

Scheme 11
General Method I

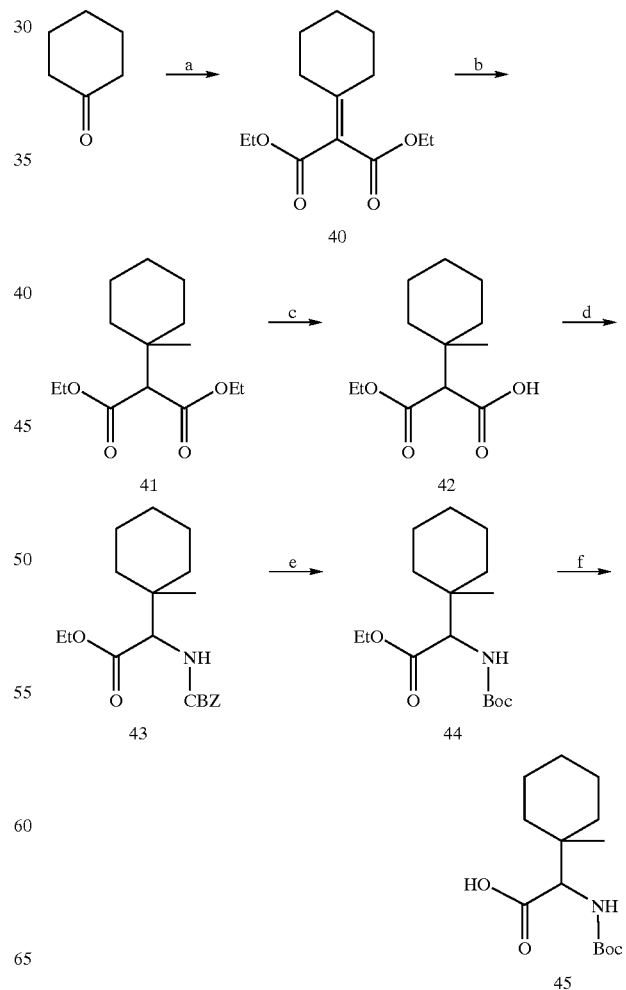

-continued
a. THF, CCl₄, TiCl₄, diethylmalonate, 0 C; pyridine, THF, 0 to RT 72 h b. MeMgBr, CuI, Et₂O, 0 C c. 1N NaOH, EtOH, RT 6 days d. Ph₂PON₃, TEA, RT to reflux to RT, BnOH e. 10% Pd(OH)₂/C, EtOAc; (Boc)₂O, K₂CO₃, THF f. 1N NaOH, dioxane Step 1

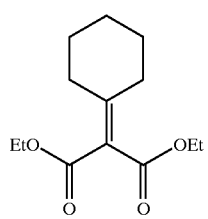

According to literature procedure (Tetrahedron 1973, 29, 435), a mixture of dry tetrahydrofuran (400 mL) and dry carbon tetrachloride (50 mL) was cooled to 0° C. (ice-salt bath) and treated with titanium tetrachloride (22.0 mL, 0.2 mole). The resulting yellow suspension was stirred at 0° C. for 5 min, treated sequentially with cyclohexanone (10.3 mL, 0.1 mole) and distilled diethylmalonate (15.2 mL, 0.1 mole) then stirred at 0° C. for 30 min. The reaction mixture was then treated with a solution of dry pyridine (32 mL, 0.40 mole) in dry THF (60 mL), stirred at 0° C. for 1.0 h, then at rt for 72 h. The reaction mixture was quenched with water (100 mL), stirred for 5 min then extracted with ether (2×200 mL). The combined organic extracts were washed with saturated sodium chloride (100 mL), saturated sodium bicarbonate (100 mL) and brine (100 mL), dried over anhydrous magnesium sulfate, filtered and concentrated. Flash chromatography using 5% EtOAc in hexane gave step 1 compound as a light yellow oil. Yield: 5.25 g (22%). MS (M+Na) 263.

Step 2

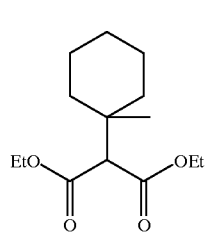

According to literature (Org. Syn. VI, 442, 1988; Liebigs Ann. Chem. 1981, 748) a mixture of 3.0 M methylmagnesium iodide (3.1 mL, 9.36 mmol) and cuprous chloride (9.0 mg) was stirred at 0° C. (ice-salt water bath), treated with a solution of Step 1 compound (1.5 g, 6.24 mmol) in dry ether (1.8 mL) over 5 min and stirred at 0° C. for 1 h, then at rt for 40 min. The mixture was slowly added to a slurry of ice and water (15 mL), treated dropwise with 10% HCl (3.7 mL) then extracted with EtOAc (3×25 mL). The combined organic extracts were washed with 1% sodium thiosulfate (2.0 mL) and saturated sodium chloride (2.0 mL), dried over anhydrous magnesium sulfate, filtered, and concentrated. Flash chromatography on a silica gel column using 5% ether in hexane (1.0 L) gave step 2 compound as a clear syrup. Yield: 1.09 g,(68%). MS (M+H)257.

Step 3

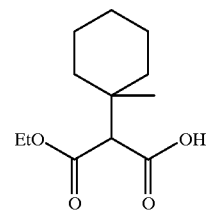

A solution of Step 2 compound (1.09 g, 4.03 mmol) in a mixture of methanol (5.4 mL) and water (2.7 mL) was treated with 1N sodium hydroxide (4.84 mL, 4.84 mmol or 1.2 equiv) and stirred at rt for 6 days. The reaction mixture still showed the presence of starting material, so THF (4.0 mL) was added and the entire mixture stirred for another 2 days. The solution was evaporated to dryness and the resulting syrup partitioned between water (8.0 mL) and ether (15 mL). The aqueous phase was acidified with 1N hydrochloric acid (4.8 mL) to pH 2–3 and extracted with EtOAc (3 ×25 mL). The combined organic extracts were washed with brine (10.0 mL), dried over anhydrous magnesium sulfate, filtered, and concentrated to give step 3 compound as a thick syrup. Yield: 875 mg, (95.1%). MS (M+H) 229.

Or alternately: solutions of the diester in a mixture of ethanol, THF, dioxane and water or mixtures thereof may be hydrolyzed with sodium hydroxide.

Step 4

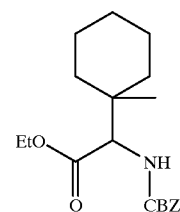

According to literature (J. Org. Chem 1994, 59, 8215), a solution of Step 3 compound (0.875 g, 3.83 mmol) in dry benzene (4.0 mL) was treated with triethylamine (0.52 mL, 3.83 mmol) and diphenylphosphoryl azide (0.85 mL, 3.83 mmol), refluxed under nitrogen for 1 h and cooled to rt. The solution was treated with benzyl alcohol (0.60 mL, 5.75 mmol or 1.5 equiv), refluxed for 17 h, cooled then diluted with ether (40 mL). The solution was washed with 10% aqueous citric acid (2×3 mL), back-extracting the citric acid wash with ether (40 mL). The combined organic extracts were washed with 5% sodium bicarbonate (2×3 mL), dried (MgSO₄), filtered, and concentrated. Flash chromatography on silica gel of the crude product with 10EtOAc in hexane (1.0 L) gave step 4 compound as a clear thick syrup. Yield: 1.15 g (90%). MS(M+H) 334.

Step 5

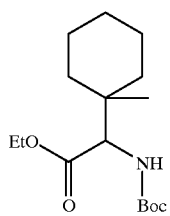

A solution of Step 4 compound (1.15 g, 3.46 mmol) in EtOAc (60 mL) was treated with palladium hydroxide on carbon (298 mg) and hydrogenated at rt for 20 h. The mixture was filtered through a celite pad and then washing the pad well with EtOAc (3×25 mL) then the filtrate was concentrated to give the free amine. A solution of the amine in tetrahydrofuran (12 mL) and water (12 mL) was treated with di-t-butyl dicarbonate (1.0 g, 4.58 mmol or 1.48 equiv) and potassium carbonate (854 mg, 6.18 mmol or 2.0 equiv), then stirred at rt for 20 h. The reaction mixture was partitioned between water (8 mL) and diethyl ether (3×40 mL) and the combined organic extracts were washed with brine (8 mL), dried (MgSO$_4$), filtered, and concentrated. Flash chromatography of the crude product with 10% EtOAc in hexane (1 L) gave step 5 compound as a clear thick syrup. Yield: 1.18 g (100%). MS:(M+H) 300.

Other methods can also be employed, for example:

According to Tetrahedron Lett. 1988, 29, 2983, where a solution of the benzylcarbamate in ethanol may be treated with triethylsilane (2 equiv), di-t-butyldicarbonate (1.1 equiv), catalytic palladium acetate and triethylamine (0.3 equiv) to give the BOC-protected amine in a "one-pot" manner.

Or alternately: Solutions of the benzylcarbamate in methanol may be subjected to hydrogenolysis in the present of di-t-butyldicarbonate to give the BOC-protected amine in a "one-pot" manner.

Step 6

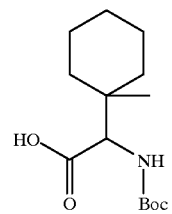

A solution of Step 5 compound (1.18 g, 3.09 mmol) in dioxane (8.0 mL) was treated with 1N sodium hydroxide (9.1 mL, 9.1 mmol or 3.0 equiv) and stirred at 60° C. (oil bath) for 28 h. The reaction mixture was concentrated to a syrup which was dissolved in water (15 mL) and extracted with ether (25 mL). The aqueous phase was acidified to pH 2–3 with 1N hydrochloric acid (9.2 mL) then extracted with EtOAc (3×50 mL). The combined organic extracts were washed with saturated sodium chloride (10 mL), dried (MgSO$_4$), filtered, and concentrated to give Step 6 compound as an off-white solid. Yield: 808 mg (96%). MS (M+H) 272.

Step 7

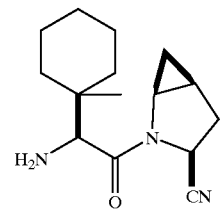

The title compound was prepared from Step 6 compound according to the procedure in General Method C where the amino acid was coupled, the amide was dehydrated, and the protecting group removed to give the title compound. MS (M+H) 262.

Compounds 90–100 were prepared by General Method I and General Method C starting from cyclohexanone, cyclopentanone and cyclobutanone, and employing methyl-, ethyl-, allyl- and propylmagnesium halides as Grignard reagents.

TABLE 5

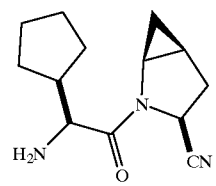

| Example # | Cycloalkane | R | NS Data M + H |
|---|---|---|---|
| 79 | cyclohexane | Methyl | 262 |
| 80 | cyclohexane | Ethyl | 276 |
| 81 | cyclopentane | Methyl | 248 |
| 82 | cyclopentane | Allyl | 274 |
| 83 | cyclopentane | Propyl | 276 |
| 84 | cyclobutane | Methyl | 234 |

EXAMPLE 85

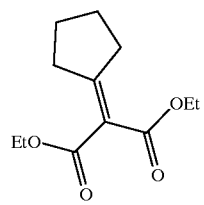

Step 1

According to Example 79: A mixture of dry carbon tetrachloride (50 mL) was cooled to 0° C. (ice-salt bath) and treated with titanium tetrachloride (11.0 mL, 0.1 mol). The resulting yellow suspension was stirred at 0° C. for 5 min, treated sequentially with cyclopentanone (4.42 mL, 0.05 mol) and distilled diethylmalonate (7.6 mL, 0.05 mol) then stirred at 0° C. for 30 min. The reaction mixture was then treated with a solution of dry pyridine (16 mL, 0.20 mol) in dry THF (30 mL), stirred at 0° C. for 1.0 h, then at rt for 20 h. The reaction mixture was quenched with water (50 mL), stirred for 5 min then extracted with ether (2×100 mL). The combined organic extracts were washed with saturated sodium chloride (50 mL), saturated sodium bicarbonate (50 mL) and brine (50 mL), dried (MgSO$_4$), filtered and concentrated. Flash chromatography using 5% EtOAc in hexane gave Step 1 compound as a light yellow oil. Yield: 7.67 g (68%). MS (M+H) 226.

Step 2

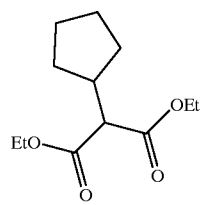

A solution of Step 1 compound (1.00 g 4.42 mmol) in methanol (50 mL) was treated with 10% Pd/C (0.20 g, 10 mol %) and hydrogenated (balloon pressure) at rt for 20 h. The mixture was diluted with methanol and filtered through a pad of celite. The filtrate was concentrated and purified by flash column chromatography on silica gel with 7% EtOAc in hexanes to give 0.84 g (91%) of Step 2 compound. MS (M+H) 229.

Step 3

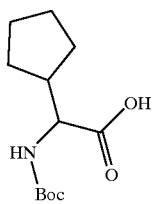

The Step 3 compound was prepared by the process outlined in General Method H, where the ester underwent hydrolysis, Curtius Rearrangement, protecting group exchange, and again final ester hydrolysis.

Step 4

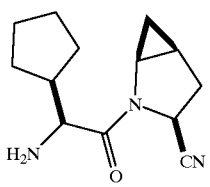

The title compound was prepared from Step 3 compound according to the procedure in General Method C where the amino acid was coupled, the amide was dehydrated, and the protecting group removed to give the title compound. MS (M+H) 234.

Examples 86 and 87 were prepared by the procedures used for Example 85 starting from cyclohexanone and cyclobutanone respectively

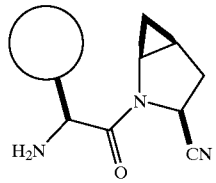

| Example # | Cycloalkane | Mass Spec M + H |
|---|---|---|
| 85 | cyclopentyl | 234 |
| 86 | cyclohexyl | 248 |
| 87 | cyclobutyl | 220 |

EXAMPLE 89

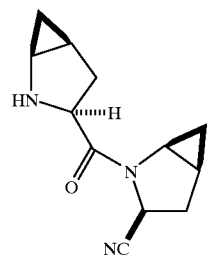

Step 1

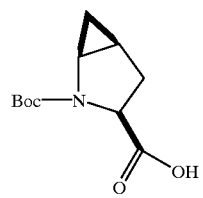

Step 1 compound was prepared in Example 6 Step 1.

Step 2

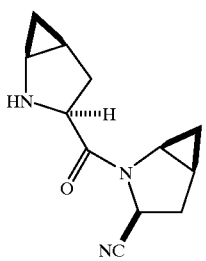

The title compound was prepared from Step 1 compound according to General Method C, where the carboxylic acid underwent a peptide coupling, the amide dehydration and protecting group removal. MS (M+H) 218.

EXAMPLES 90 TO 99

Examples of compounds where X=H include the following compounds which may be prepared employing procedures as described hereinbefore.

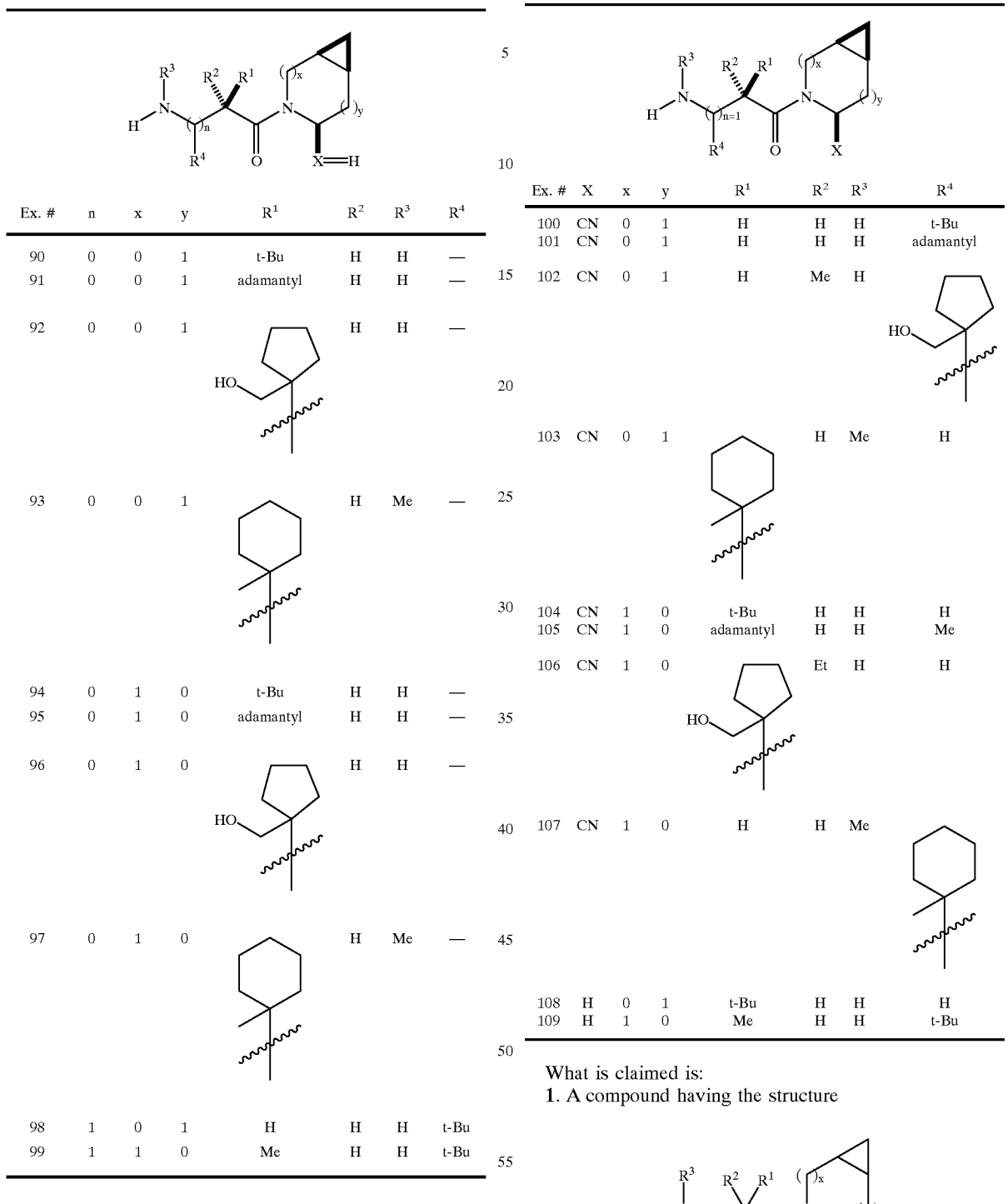

R¹, R², R³ and R⁴ are the same or different and are independently selected from hydrogen, alkyl, alkenyl, alkynyl, cycloalkyl, cycloalkylalkyl, bicycloalkyl, tricycloalkyl, alkylcycloalkyl, hydroxyalkyl, hydroxyalkylcycloalkyl, hydroxycycloalkyl, hydroxybicycloalkyl, hydroxytricycloalkyl, bicycloalkylalkyl, alkylthioalkyl, arylalkylthioalkyl, cycloalkenyl, aryl, aralkyl, heteroaryl, heteroarylalkyl, cycloheteroalkyl or cycloheteroalkylalkyl; all optionally substituted through available carbon atoms with 1, 2, 3, 4 or 5 groups selected from hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfinyl, aminosulfonyl, alkylsulfinyl, sulfonamido or sulfonyl;

and R¹ and R³ may optionally be taken together to form —(CR⁵R⁶)$_m$— where m is 2 to 6, and R⁵ and R⁶ are the same or different and are independently selected from hydroxy, alkoxy, H, alkyl, alkenyl, alkynyl, cycloalkyl, halo, amino, substituted amino, cycloalkylalkyl, cycloalkenyl, aryl, arylalkyl, heteroaryl, heteroarylalkyl, cycloheteroalkyl, cycloheteroalkylalkyl, alkylcarbonylamino, arylcarbonylamino, alkoxycarbonylamino, aryloxycarbonylamino, alkoxycarbonyl, aryloxycarbonyl, or alkylaminocarbonylamino, or R¹ and R4 may optionally be taken together to form —(CR⁷R⁸)$_p$— wherein p is 2 to 6, and R⁷ and R⁸ are the same or different and are independently selected from hydroxy, alkoxy, cyano, H, alkyl, alkenyl, alkynyl, cycloalkyl, cycloalkylalkyl, cycloalkenyl, halo, amino, substituted amino, aryl, arylalkyl, heteroaryl, heteroarylalkyl, cycloheteroalkyl, cycloheteroalkylalkyl, alkylcarbonylamino, arylcarbonylamino, alkoxycarbonylamino, aryloxycarbonylamino, alkoxycarbonyl, aryloxycarbonyl, or alkylaminocarbonylamino, or optionally R¹ and R³ together with

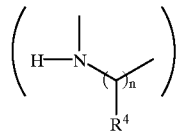

form a 5 to 7 membered ring containing a total of 2 to 4 heteroatoms selected from N, O, S, SO, or SO₂;
or optionally R¹ and R³ together with

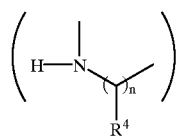

form a 4 to 8 membered cycloheteroalkyl ring wherein the cycloheteroalkyl ring has an optional aryl ring fused thereto or an optional 3 to 7 membered cycloalkyl ring fused thereto;

with the proviso that where x is 1 and y is 0, X is H, n is o, and one of R¹ and R² is H and the other is alkyl, then R³ is other than pyridyl or substituted pyridyl;

including all stereoisomers thereof;

and a pharmaceutically acceptable salt thereof, or a prodrug ester thereof, and all stereoisomers thereof.

2. The compound as defined in claim 1 having the structure:

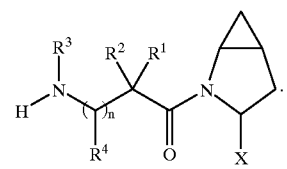

3. The compound as defined in claim 1 having the structure:

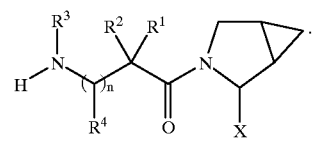

4. The compound as defined in claim 1 having the structure:

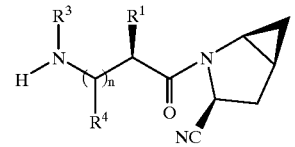

5. The compound as defined in claim 1 having the structure:

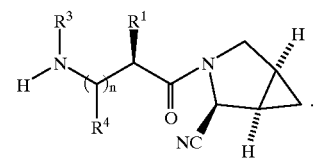

6. The compound as defined in claim 1 wherein:

R³ is H, R¹ is H, alkyl, cycloalkyl, bicycloalkyl, tricycloalkyl, alkylcycloalkyl, hydroxyalkyl, hydroxyalkylcycloalkyl, hydroxycycloalkyl hydroxybicycloalkyl, or hydroxytricycloalkyl, R² is H or alkyl, n is 0, X is CN.

7. The compound as defined in claim 1 wherein the cyclopropyl fused to the pyrrolidine has the configuration:

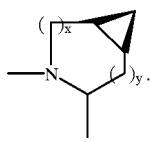

8. The compound as defined in claim 1 having the structure:

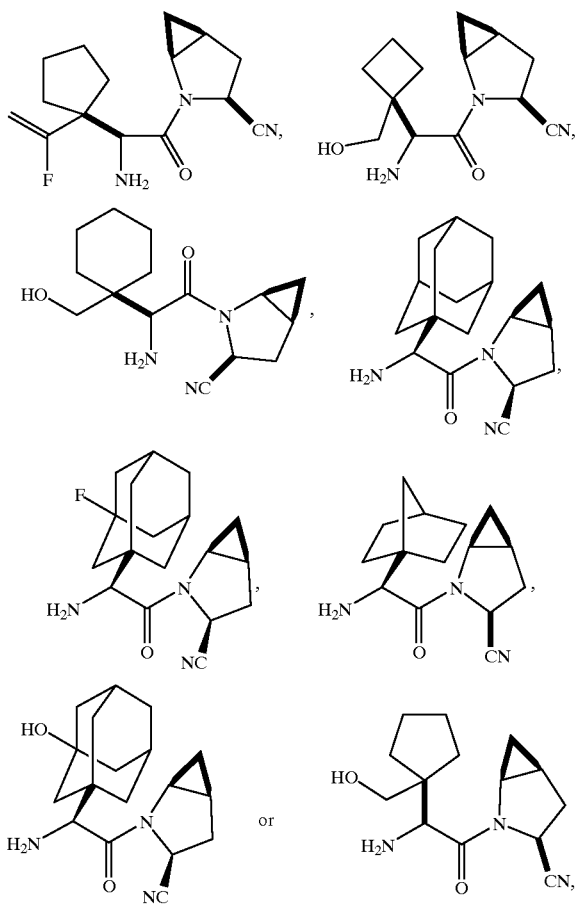

or a pharmaceutically acceptable salt thereof.

9. The compound as defined in claim 8 wherein the pharmaceutically acceptable salt is the hydrochloride salt or the trifluoroacetic acid salt.

10. The compound as defined in claim 1 which is

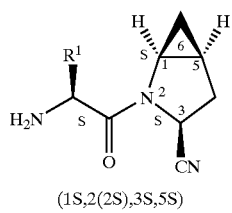

wherein $R^1$ is alkyl, cycloalkyl, bicycloalkyl, tricycloalkyl, alkylcycloalkyl, hydroxyalkyl, hydroxycycloalkyl, hydroxyalkylcycloalkyl, hydroxybicycloalkyl, or hydroxytricycloalkyl, or

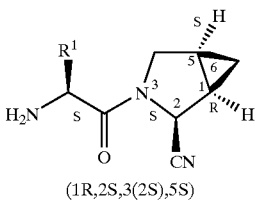

wherein $R^1$ is alkyl, cycloalkyl, bicycloalkyl, tricycloalkyl, alkylcycloalkyl, hydroxyalkyl, hydroxycycloalkyl, hydroxyalkylcycloalkyl, hydroxybicycloalkyl, or hydroxytricycloalkyl.

11. A pharmaceutical composition comprising a compound as defined in claim 1 and a pharmaceutically acceptable carrier therefor.

12. A pharmaceutical combination comprising a DP4 inhibitor compound as defined in claim 1 and an antidiabetic agent other than a DP4 inhibitor for treating diabetes and related diseases, an anti-obesity agent and/or a lipid-modulating agent.

13. The pharmaceutical combination as defined in claim 12 comprising said DP4 inhibitor compound and an antidiabetic agent.

14. The combination as defined in claim 13 wherein the antidiabetic agent is 1, 2, 3 or more of a biguanide, a sulfonyl urea, a glucosidase inhibitor, a PPAR γ agonist, a PPAR α/γ dual agonist, an SGLT2 inhibitor, an aP2 inhibitor, a glycogen phosphorylase inhibitor, an AGE inhibitor, an insulin sensitizer, a glucagon-like peptide-1 (GLP-1) or mimetic thereof, insulin and/or a meglitinide.

15. The combination as defined in claim 14 wherein the antidiabetic agent is 1, 2, 3 or more of metformin, glyburide, glimepiride, glipyride, glipizide, chlorpropamide, gliclazide, acarbose, miglitol, pioglitazone, troglitazone, rosiglitazone, insulin, Gl -262570, isaglitazone, JTT-501, NN-2344, L895645, YM-440, R-119702, AJ9677, repaglinide, nateglinide, KAD1129, APR-HO39242, GW-409544, KRP297, AC2993, Exendin-4, LY307161, NN2211, and/or LY315902.

16. The combination as defined in claim 13 wherein the compound is present in a weight ratio to the antidiabetic agent within the range from about 0.01 to about 100:1.

17. The combination as defined in claim 12 wherein the anti-obesity agent is a beta 3 adrenergic agonist, a lipase inhibitor, a serotonin (and dopamine) reuptake inhibitor, a thyroid receptor beta compound, an anorectic agent, and/or a fatty acid oxidation upregulator.

18. The combination as defined in claim 17 wherein the anti-obesity agent is orlistat, ATL-962, AJ9677, L750355, CP331648, sibutramine, topiramate, axokine, dexamphetamine, phentermine, phenylpropanolamine, famoxin, and/or mazindol.

19. The combination as defined in claim 12 wherein the lipid modulating agent is an MTP inhibitor, an HMG CoA reductase inhibitor, a squalene synthetase inhibitor, a fibric acid derivative, an upregulator of LDL receptor activity, a lipoxygenase inhibitor, an ACAT inhibitor, a cholesteryl ester transfer protein inhibitor, or an ATP citrate lyase inhibitor.

20. The combination as defined in claim 19 wherein the lipid modulating agent is pravastatin, lovastatin, simvastatin, atorvastatin, cerivastatin, fluvastatin, nisvastatin, visastatin, fenofibrate, gemfibrozil, clofibrate, implitapide, CP-529,414, avasimibe, TS-962, MD-700, and/or LY295427.

21. The combination as defined in claim 19 wherein the DP4 inhibitor is present in a weight ratio to the lipid-modulating agent within the range from about 0.01 to about 100:1.

22. A pharmaceutical combination comprising a DP4 inhibitor compound as defined in claim 1 and an agent for treating infertility, an agent for treating polycystic ovary syndrome, an agent for treating a growth disorder and/or frailty, an anti-arthritis agent, an agent for preventing inhibiting allograft rejection in transplantation, an agent for treating autoimmune disease, an anti-AIDS agent, an agent for treating inflammatory bowel disease/syndrome, an agent for treating anorexia nervosa, an anti-osteoporosis agent and/or an anti-obesity agent.

23. A method for treating diabetes, insulin resistance, hyperglycemia, hyperisulinemia, or elevated blood levels of free fatty acids or glycerol, obesity, Syndrome X, dysmetabolic syndrome, diabetic complications, hypertriglyceridemia, hyperinsulinemia, atherosclerosis, impaired glucose homeostasis, impaired glucose tolerance, infertility, polycystic ovary syndrome, growth disorders, frailty, arthritis, allograft rejection in transplantation, autoimmune diseases, AIDS, intestinal diseases, inflammatory bowel syndrome, nervosa, osteoporosis, or an immunomodulatory disease or a chronic inflammatory bowel disease, which comprises administering to a mammalian species in need of treatment a therapeutically effective amount of a compound as defined in claim 1.

24. The method as defined in claim 23 for treating type II diabetes and/or obesity.

\* \* \* \* \*

UNITED STATES PATENT AND TRADEMARK OFFICE
CERTIFICATE OF CORRECTION

PATENT NO. : 6,395,767 B2　　　　　　　　　　　　　　　　　　　　　　Page 1 of 1
DATED : May 28, 2002
INVENTOR(S) : Jeffrey A. Robl et al.

It is certified that error appears in the above-identified patent and that said Letters Patent is hereby corrected as shown below:

Column 91,
Lines 9-10, should read -- A compound having the structure: --
Line 54, should read -- A compound which is --.

Signed and Sealed this

Twenty-seventh Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO.    : 6,395,767 B2
DATED         : May 28, 2002
INVENTOR(S)   : Jeffrey A. Robl et al.

It is certified that error appears in the above-identified patent and that said Letters Patent is hereby corrected as shown below:

Column 7,
Line 6, change "PGI" to -- $PG_1$ --.

Column 14,
Line 50, insert -- 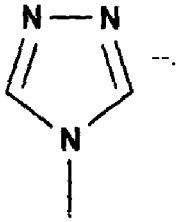 --.

Line 56, between "refers" and "cycloheteroakyl", insert -- to --.
Line 57, between "a" and "atom", insert -- C --.

Column 15,
Line 54, change "γ" to -- β --.

Column 20,
Line 59, "2,1" should be -- 2,3 --.

Column 29,
Line 23, change "w" to -- % --.

Column 30,
Line 2, after "(M+H)⁺" and before "197", insert -- = --.

Column 32,
Line 62, after "(M+H)⁺" and before "222", insert -- = --.

Column 33,
Line 3, change "HO" to read -- $H_2O$ --.
Line 7, change "CH2cl₂" to read -- $CH_2Cl_2$ --.
Line 11, after "METHOD", insert -- A --.

Column 34,
Line 62, delete "15".

Column 41,
Line 43, after "was", delete "a".
Line 44, after "over", delete "a".

UNITED STATES PATENT AND TRADEMARK OFFICE
CERTIFICATE OF CORRECTION

PATENT NO. : 6,395,767 B2
DATED : May 28, 2002
INVENTOR(S) : Jeffrey A. Robl et al.

It is certified that error appears in the above-identified patent and that said Letters Patent is hereby corrected as shown below:

Column 43,
Line 36, delete "E".
Line 55, change "48.61" to -- 8.61 --.

Column 44,
Line 39, change "200" to -- 300 --.

Column 46,
Line 58, change "ter" to -- water --.
Line 58, after "20" and before "Detection", insert -- mL/min. --.
Line 65, change "dimethylcylopentanone" to -- dimethylcyclopentanone --.

Column 52,
Line 64, change "25" to -- 28 --.

Column 53,
Line 31, change "OSO$_4$" to -- OsO4 --.
Line 65, after "100%" and before "Solvent A", insert -- B, --.
Line 66, after "vent B =" and before "MeOH", insert -- 90% --.

Column 62,
Line 67, change "549" to -- 540 --.

Column 66,
Line 24, change "CH2Cl$_2$" to read -- CH$_2$Cl$_2$ --.

Column 69,
Line 21, change "9" to -- 8 --.
Line 30, change "Hbl" to -- HCl --.

Column 70,
Line 56, move "Step 1" to line 65.

Column 72,
Line 36, change "50º" to -- 5º --.
Line 65, change "2.2(" to -- 2.28 --.
Line 65, change "30mL2" to -- 30 mL --.

Column 73,
Line 25, change "the n" to -- then --.
Line 26, change "et her" to -- ether --.

UNITED STATES PATENT AND TRADEMARK OFFICE
CERTIFICATE OF CORRECTION

PATENT NO. : 6,395,767 B2
DATED : May 28, 2002
INVENTOR(S) : Jeffrey A. Robl et al.

It is certified that error appears in the above-identified patent and that said Letters Patent is hereby corrected as shown below:

Column 74,
Line 32, change "50º" to -- 5º --.

Column 79,
Line 61, change "100" to -- 10% --.

Column 82,
Line 65, change "10EtOAc" to -- 10% EtOAc --.

Column 84,
Line 34, change "NS" to -- MS --.

Column 92,
Line 42, change "APR" to -- AR --.

Signed and Sealed this

Twenty-ninth Day of November, 2005

JON W. DUDAS
*Director of the United States Patent and Trademark Office*